US012116382B2

(12) United States Patent
Poon et al.

(10) Patent No.: US 12,116,382 B2
(45) Date of Patent: Oct. 15, 2024

(54) FUNCTIONALIZED N-ACETYLGALACTOSAMINE ANALOGS

(71) Applicant: Hongene Biotech Corporation, Union City, CA (US)

(72) Inventors: Wing C. Poon, Fremont, CA (US); Gang Zhao, Union City, CA (US); Gengyu Du, Union City, CA (US); Yun-Chiao Yao, Union City, CA (US); Ruiming Zou, Foster City, CA (US); Aldrich N. K. Lau, Palo Alto, CA (US); David Yu, Union City, CA (US); Guijun Yu, Union City, CA (US); Zhixia Li, Union City, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 18/520,195

(22) Filed: Nov. 27, 2023

(65) Prior Publication Data
US 2024/0247023 A1 Jul. 25, 2024

Related U.S. Application Data

(60) Provisional application No. 63/385,087, filed on Nov. 28, 2022.

(51) Int. Cl.
C07H 19/067 (2006.01)
C07K 1/04 (2006.01)

(52) U.S. Cl.
CPC ............. *C07H 19/067* (2013.01); *C07K 1/04* (2013.01)

(58) Field of Classification Search
None
See application file for complete search history.

(56) References Cited

U.S. PATENT DOCUMENTS

| 5,681,940 | A  | 10/1997 | Wang |
| 5,811,512 | A  | 9/1998 | Hirschmann |
| 6,001,823 | A  | 12/1999 | Hultgren |
| 6,174,867 | B1 | 1/2001 | Hindsgaul |
| 6,310,042 | B1 | 10/2001 | Persson |
| 6,713,448 | B2 | 3/2004 | Carter |
| 7,037,936 | B2 | 5/2006 | McKenna et al. |
| 7,291,603 | B2 | 11/2007 | Wilde |
| 7,449,570 | B2 | 11/2008 | Wilde |
| 7,488,733 | B2 | 2/2009 | Hendrix |
| 7,622,448 | B2 | 11/2009 | Dalko |
| 7,737,287 | B2 | 6/2010 | Meutermans |
| 7,989,422 | B2 | 8/2011 | Meutermans |
| 7,994,140 | B2 | 8/2011 | Meutermans |
| 8,119,779 | B2 | 2/2012 | McGuigan |
| 8,163,551 | B2 | 4/2012 | Alley |
| 8,426,345 | B2 | 4/2013 | Tometzki |
| 8,497,385 | B2 | 7/2013 | Wender |
| 8,603,998 | B2 | 12/2013 | Guzi |
| 8,686,045 | B2 | 4/2014 | Longo |
| 8,937,167 | B2 | 1/2015 | Janetka |
| 8,962,580 | B2 | 2/2015 | Manoharan et al. |
| 9,284,343 | B2 | 3/2016 | Beaucage |
| 9,445,596 | B2 | 9/2016 | Schroeder |
| 9,487,551 | B2 | 11/2016 | Choe |
| 9,504,702 | B2 | 11/2016 | Senter |
| 9,534,008 | B2 | 1/2017 | Choe |
| 9,598,454 | B2 | 3/2017 | Ramtohul |
| 9,868,754 | B2 | 1/2018 | Choe |
| 9,957,289 | B2 | 5/2018 | Janetka |
| 9,975,915 | B1 | 5/2018 | Migaud |
| 10,000,520 | B2 | 6/2018 | Migaud |
| 10,016,518 | B2 | 7/2018 | Anthony et al. |
| 10,138,265 | B2 | 11/2018 | Haydon |
| 10,167,259 | B2 | 1/2019 | Osmulski |
| 10,183,036 | B2 | 1/2019 | Dellinger |
| 10,227,290 | B2 | 3/2019 | Fischbach |
| 10,280,190 | B2 | 5/2019 | Dellinger |
| 10,294,474 | B2 | 5/2019 | Li et al. |
| 10,350,228 | B2 | 7/2019 | Benjamin |
| 10,391,068 | B2 | 8/2019 | Biasini |
| 10,428,106 | B2 | 10/2019 | Butora |
| 10,662,427 | B2 | 5/2020 | Melquist et al. |
| 10,669,301 | B2 | 6/2020 | Guzaev et al. |
| 10,682,367 | B2 | 6/2020 | Fuchs |
| 10,781,175 | B2 | 9/2020 | Guzaev et al. |

(Continued)

FOREIGN PATENT DOCUMENTS

| CN | 1188771 | 7/1998 |
| CN | 103102345 | 5/2013 |

(Continued)

OTHER PUBLICATIONS

Carey, 1992, Organic Chemistry, 2d ed., McGraw-Hill, Inc., New York, pp. 328-331.
Craig et al., 2018, Recent preclinical and clinical advances in oligonucleotide conjugates. Expert Opin. Drug. Deliv. 15(6):629-640.
Debacker et al., 2020, Delivery of Oligonucleotides to the Liver with GalNAc: From Research to Registered Therapeutic Drug. Mol. Ther., 8:1759-1771.
Greene et al., 1999, Protective Groups in Organic Synthesis, 3rd Ed., John Wiley & Sons, New York (TOC).
Huang, 2017, Preclinical and Clinical Advances of GalNAc-Decorated Nucleic Acid Therapeutics. Mol. Ther. Nucleic. Acids., 6:116-132.

(Continued)

*Primary Examiner* — Traviss C McIntosh, III
(74) *Attorney, Agent, or Firm* — Knobbe, Martens, Olson & Bear, LLP

(57) ABSTRACT

Embodiments of the present application relate to functionalized N-acetylgalactosamine analogs, methods of making, and uses of the same. In particular, polyvalent N-acetylgalactosamine analogs may be prepared by utilizing a wide variety of linkers containing functional groups. These functionalized N-acetylgalactosamine analogs may be used in the preparation of targeted delivery of oligonucleotide-based therapeutics.

49 Claims, No Drawings

Specification includes a Sequence Listing.

(56) References Cited

U.S. PATENT DOCUMENTS

| | | |
|---|---|---|
| 10,995,097 B2 | 5/2021 | Hergenrother |
| 11,052,133 B2 | 7/2021 | Mahdavi |
| 11,389,468 B2 | 7/2022 | Dellinger |
| 11,418,822 B2 | 8/2022 | Weil et al. |
| 11,649,260 B2 | 5/2023 | Guan et al. |
| 11,692,001 B2 | 7/2023 | Poon |
| 11,884,691 B2 | 1/2024 | Poon et al. |
| 2006/0276419 A1 | 12/2006 | De Luca |
| 2007/0249556 A1 | 10/2007 | Brubaker |
| 2008/0009418 A1 | 1/2008 | Tometzki |
| 2008/0176936 A1 | 7/2008 | Meutermans |
| 2008/0280837 A1 | 11/2008 | Halliday |
| 2009/0176717 A1 | 7/2009 | Magnani |
| 2009/0214439 A1 | 8/2009 | Kumar |
| 2011/0250138 A1 | 10/2011 | Fan |
| 2012/0040916 A1 | 2/2012 | Moon |
| 2012/0202877 A1 | 8/2012 | Von Itzstein |
| 2012/0276108 A1 | 11/2012 | Priebe |
| 2013/0023491 A1 | 1/2013 | Annes |
| 2016/0266133 A1 | 9/2016 | Levy |
| 2017/0022505 A1 | 1/2017 | Hadwiger et al. |
| 2018/0064819 A1 | 3/2018 | Li et al. |
| 2018/0195070 A1 | 7/2018 | Melquist et al. |
| 2018/0303861 A1 | 10/2018 | Marcotulli |
| 2019/0211368 A1 | 7/2019 | Butora et al. |
| 2019/0225644 A1 | 7/2019 | Butora et al. |
| 2019/0247468 A1 | 8/2019 | Mahdavi et al. |
| 2019/0256849 A1 | 8/2019 | Li et al. |
| 2020/0040025 A1 | 2/2020 | Haydon |
| 2020/0085849 A1 | 3/2020 | Marcotulli |
| 2020/0263179 A1 | 8/2020 | Melquist et al. |
| 2020/0270611 A1 | 8/2020 | Gryaznov et al. |
| 2020/0354399 A1 | 11/2020 | Robichaud |
| 2020/0384004 A1 | 12/2020 | Marcotulli |
| 2021/0099739 A1 | 4/2021 | Weil et al. |
| 2021/0177875 A1 | 6/2021 | Marcotulli |
| 2022/0002269 A1 | 1/2022 | Stewart |
| 2022/0160745 A1 | 5/2022 | Estrela Arigüel |
| 2023/0279051 A1 | 9/2023 | Poon et al. |
| 2024/0083934 A1* | 3/2024 | Li .................... C07H 19/10 |

FOREIGN PATENT DOCUMENTS

| | | |
|---|---|---|
| CN | 110642910 | 1/2020 |
| EP | 1 336 602 | 8/2003 |
| EP | 3 677 588 | 7/2020 |
| EP | 3 763 815 | 1/2021 |
| JP | 2007137843 | 6/2007 |
| KR | 20190076339 | 7/2019 |
| WO | WO 91/06555 | 5/1991 |
| WO | WO 92/19638 | 11/1992 |
| WO | WO 98/07433 | 2/1998 |
| WO | WO 03/039523 | 5/2003 |
| WO | WO 05/061523 | 7/2005 |
| WO | WO 06/037185 | 4/2006 |
| WO | WO 06/125554 | 11/2006 |
| WO | WO 08/029294 | 3/2008 |
| WO | WO 11/067588 | 6/2011 |
| WO | WO 2013/033230 | 3/2013 |
| WO | WO 14/206349 | 12/2014 |
| WO | WO 15/066697 | 5/2015 |
| WO | WO 15/105083 | 7/2015 |
| WO | WO 15/168618 | 11/2015 |
| WO | WO 17/062029 | 4/2017 |
| WO | WO 17/066782 | 4/2017 |
| WO | WO 17/066789 | 4/2017 |
| WO | WO 17/066791 | 4/2017 |
| WO | WO 17/177326 | 10/2017 |
| WO | WO 18/009539 | 1/2018 |
| WO | WO 18/044350 | 3/2018 |
| WO | WO 18/067900 | 4/2018 |
| WO | WO 18/200357 | 11/2018 |
| WO | WO 18/213420 | 11/2018 |
| WO | WO 19/051257 | 3/2019 |
| WO | WO 19/053661 | 3/2019 |
| WO | WO 19/075419 | 4/2019 |
| WO | WO 19/209840 | 10/2019 |
| WO | WO 19/211595 | 11/2019 |
| WO | WO 19/232554 | 12/2019 |
| WO | WO 20/093061 | 5/2020 |
| WO | WO 20/093098 | 5/2020 |
| WO | WO 21/037205 | 3/2021 |
| WO | WO 21/188586 | 9/2021 |
| WO | WO 22/053576 | 3/2022 |
| WO | WO 22/055726 | 3/2022 |
| WO | WO 22/076922 | 4/2022 |

OTHER PUBLICATIONS

IUPAC-IUB Commission on Biochemical Nomenclatures, 1972, Abbreviated nomenclature of synthetic polypeptides (polymerized amino acids), revised recommendations (1971), Biochem. 11(5):942-944.

Lepage et al., 2013, Stereoselective Synthesis of α-Glycosyl Azides, European Journal of Organic Chemistry, 2013(10): 1963-1972.

Li et al., 2012, Identification of a specific inhibitor of nOGA—a caspase-3 cleaved O-GlcNAcase variant during apoptosis, Biochemistry (Moscow), 77(2):194-200.

McMurry, 2000, Organic Chemistry, 5th ed., Brooks/Cole, Pacific Grove, CA, pp. 398 and 408.

McOmie, ed., 1973, Protective Groups in Organic Chemistry, Plenum Press (TOC).

Rao et al., Nov. 1, 2011, A sucrose-derived scaffold for multimerization of bioactive peptides, Bioorganic & Medicinal Chemistry, 19(21):6474-6482.

Roberts et al., 2020, Advances in oligonucleotide drug delivery. Nat. Rev. Drug Discov. 10,:673-694.

Saneyoshi et al., 2017, Alkyne-linked reduction-activated protecting groups for diverse functionalization on the backbone of oligonucleotides, Bioorganic & Medicinal Chemistry, 25(13):3350-3356.

Scheit, 1980, Nucleotide analogs: Synthesis and biological function. New York: John Wiley & Sons (TOC).

Streitwieser et al., 1981, Introduction to Organic Chemistry, 2d ed., Macmillan Publishing Co., Inc., New York, pp. 169-171.

Uhlman et al., Jun. 1990, Antisense oligonucleotides: a new therapeutic principle, Chemical Reviews, 90(4):543-584.

Yamada et al., 2011, Versatile site-specific conjugation of small molecules to siRNA using click chemistry, J. Org. Chem., 76:1198-1211.

Anwar et al., 2022, Combining CuAAC reaction enables sialylated Bi- and triantennary pseudo mannose N-glycans for investigating Siglec-7 interactions, Bioorganic & Medicinal Chemistry, 67:116839 and supporting information.

Matulic-Adamic et al., 2002, Synthesis of N-acetyl-D-galactosamine and folic acid conjugated ribozymes, Bioconjugate chemistry, 13(5):1071-1078.

International search report and written opinion dated Mar. 7, 2024 in international application No. PCT/US2023/081157, filed Nov. 27, 2023.

* cited by examiner

FUNCTIONALIZED N-ACETYLGALACTOSAMINE ANALOGS

BACKGROUND

Field

The present application relates to functionalized N-acetylgalactosamine analogs and their methods of preparation. The functionalized N-acetylgalactosamine analogs disclosed herein may be used for targeted in vivo delivery of oligonucleotide-based therapeutics.

REFERENCE TO SEQUENCE LISTING

The present application is being filed along with a Sequence Listing in electronic format. The Sequence Listing is provided as a file entitled "HGENE.023A_Sequence_Listing.xml" created on Nov. 17, 2023, which is 1,964 bytes in size. The information in the electronic format of the Sequence Listing is incorporated herein by reference in its entirety.

BACKGROUND

Description of the Related Art

Oligonucleotide-based drugs have become a powerful epitome having ability to treat various diseases. N-acetylgalactosamine (GalNAc) is a well-defined liver-targeted moiety benefiting from its high affinity with asialoglycoprotein receptor (ASGPR). It can facilitate uptake and clearance of circulating GalNAc-conjugated oligo via clathrin-mediated endocytosis. The strongest attribute of GalNAc conjugates, compared to other oligo conjugates, is the internalization and cellular trafficking efficiency, which enables near-complete mRNA knockdown at exceedingly low doses in preclinical species and human subjects. This differentiating factor is related to the high membrane density of the ASGPR on hepatocytes and the rapid cycle in which it internalizes and recycles back to the cell surface. Only 15 mins are required for ASGPR internalization and recycling to the cell surface.

ASGPR consists of two homologous subunits, designated H1 and H2 in the human system, which form a non-covalent heterooligomeric complex with estimated ratios of 2:1 and 5:1, respectively. Both subunits are single-spanning membrane proteins with a calcium-dependent Gal/GalNAc recognition domain (CRDs). On the native receptor on the hepatocyte surface these binding sites are 25-30 Å apart. All conjugations of mono-, di-, tri-, or tetra-GalNAc sugars can enhance the delivery efficiency of oligonucleotides to hepatocytes. Binding hierarchy of polyvalent ligands is: tetraantennary>triantennary>>diantennary>>monoantennary. Since the fourth GalNAc moiety present in the tetraantennary ligand does not markedly enhance the affinity, it was presumed that the binding requirements of the cell-surface receptor are largely saturated by the triantennary structure. Scientists have reached a consensus that triantennary GalNAc analogs with a mutual distance of 20 Å exhibit the highest affinity with ASGPR.

Polyvalent GalNAc analogs have been previously reported. Oligonucleotide therapeutics have pharmacological challenges including susceptibility to nuclease-mediated degradation, rapid elimination, poor biodistribution, insufficient membrane permeability, immune stimulation, and potentially significant off-target effects. Accordingly, a need exists for preparing novel functionalized GalNAc analogs to improve drug delivery.

SUMMARY

Some aspect of the present disclosure relates to compounds of Formula (I):

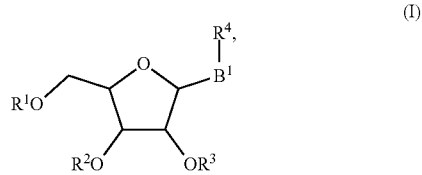

wherein:
each of $R^1$, $R^2$, and $R^3$ is independently $-L^{1a}$-Z-$L^2$-G, $-L^{1b}$-C(=O)NR$^4$R$^B$, or $-L^{1c}$-C(=O)NR$^5$R$^6$;
each of $R^A$ and $R^B$ is independently hydrogen, optionally substituted $C_{1-6}$ alkyl, or $-L^3$-Z-$L^4$-G, and at least one of $R^A$ and $R^B$ is $-L^3$-Z-$L^4$-G;
$R^4$ is hydrogen, —Z-$L^5$-G, or $-L^{1c}$-C(=O)NR$^5$R$^6$;
provided that one of $R^1$, $R^2$, $R^3$, and $R^4$ is $-L^{1c}$-C(=O)NR$^5$R$^6$ and the others of $R^1$, $R^2$, $R^3$, and $R^4$ are not $-L^{1c}$-C(=O)NR$^5$R$^6$;
each $R^5$ is independently

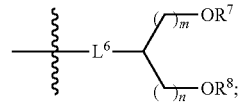

each of m and n is independently 0, 1, 2 or 3;
$R^6$ is H or $C_1$-$C_6$ alkyl;
$R^7$ is a hydroxy protecting group;
$R^8$ is hydrogen, a phosphoramidite moiety, —C(=O)CH$_2$CH$_2$C(=O)R$^{8A}$, or —P(OR$^{8B}$)NR$^{8C}$R$^{8D}$;
$R^{8A}$ is —OH, —OR$^9$ or —NR$^{10}$R$^{11}$;
each of $R^{8B}$, $R^{8C}$ and $R^{8D}$ is independently H, $C_{1-6}$ haloalkyl, or unsubstituted or substituted $C_{1-6}$ alkyl;
$R^9$ is unsubstituted or substituted $C_{1-6}$ alkyl, or a hydroxy protecting group;
each of $R^{10}$ and $R^{11}$ is independently H, unsubstituted or substituted $C_{1-6}$ alkyl, or an amino protecting group;
$L^6$ is an optionally substituted $C_{1-10}$ membered alkylene, optionally substituted $C_2$-$C_{10}$ alkenylene, or optionally substituted 2 to 15 membered heteroalkylene where one or more carbon atoms are replaced with C(=O), S, O or N;
each of $L^{1a}$, $L^{1b}$, $L^{1c}$ and $L^3$ is independently optionally substituted $C_{1-10}$ alkylene, optionally substituted $C_2$-$C_{10}$ alkenylene, or optionally substituted 2 to 15 membered heteroalkylene where one or more carbon atoms are replaced with C(=O), O, S or N;
each Z is a triazole ring, or a bi-, tri-, or tetracyclic ring system having a fused triazole ring;
each of $L^2$, $L^4$, and $L^5$ is independently optionally substituted $C_{1-10}$ alkylene, optionally substituted $C_2$-$C_{10}$ alkenylene, or optionally substituted 2 to 15 membered heteroalkylene wherein one or more carbon atoms are replaced with C(=O), O, S or N; or $C_1$-$C_{10}$ alkylene or 2 to 15 membered heteroalkylene each independently interrupted by a ring or ring system selected from the group consisting of optionally substituted $C_6$-$C_{10}$ arylene, optionally substituted $C_3$-$C_{10}$ cycloalkylene, optionally substituted five to ten membered heteroarylene, and optionally substituted three to ten membered heterocyclylene;

$B^1$ is a natural nucleobase, a modified natural nucleobase, or an unnatural nucleobase;

G is

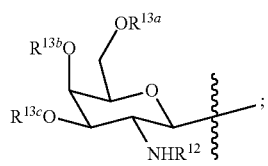

$R^{12}$ is —C(=O)$C_{1-6}$ alkyl, —C(=O)$C_{1-6}$ haloalkyl, or —C(=O)phenyl; and each of $R^{13a}$, $R^{13b}$ and $R^{13c}$ is independently hydrogen, benzyl (Bn), or —C(=O)$R^{13A}$, wherein $R^{13A}$ is $C_{1-6}$ alkyl, $C_{1-6}$ haloalkyl, or optionally substituted phenyl;

provided that the compound has three or more G groups.

In some embodiments, compounds of Formula (I) have the structure of Formula (Ia) or (Ia'):

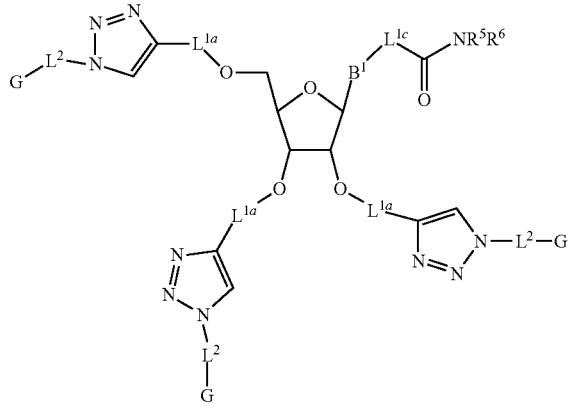

(Ia)

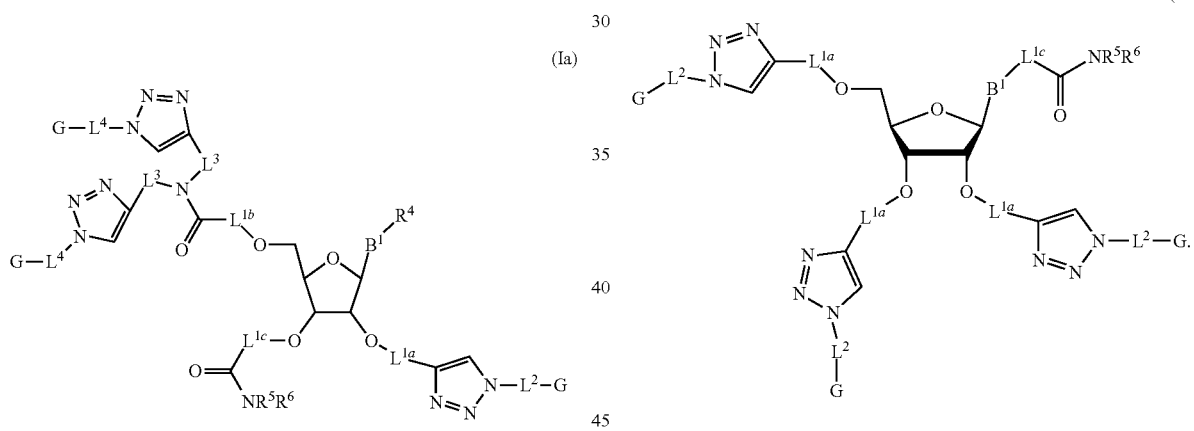

(Ia')

In some embodiments, compounds of Formula (I) have the structure of Formula (Ib) or (Ib'):

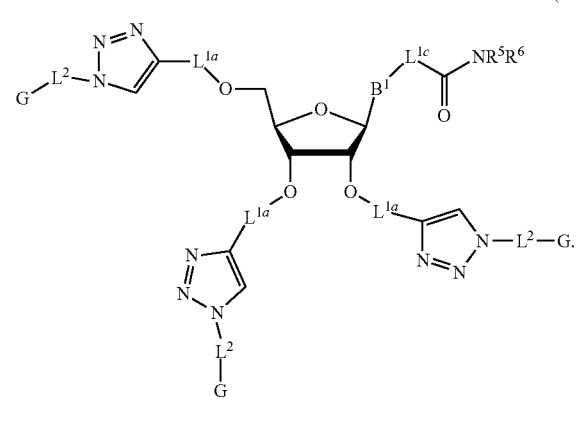

(Ib)

(Ib')

In some embodiments, compounds of Formula (I) have the structure of Formula (Ic) or (Ic'):

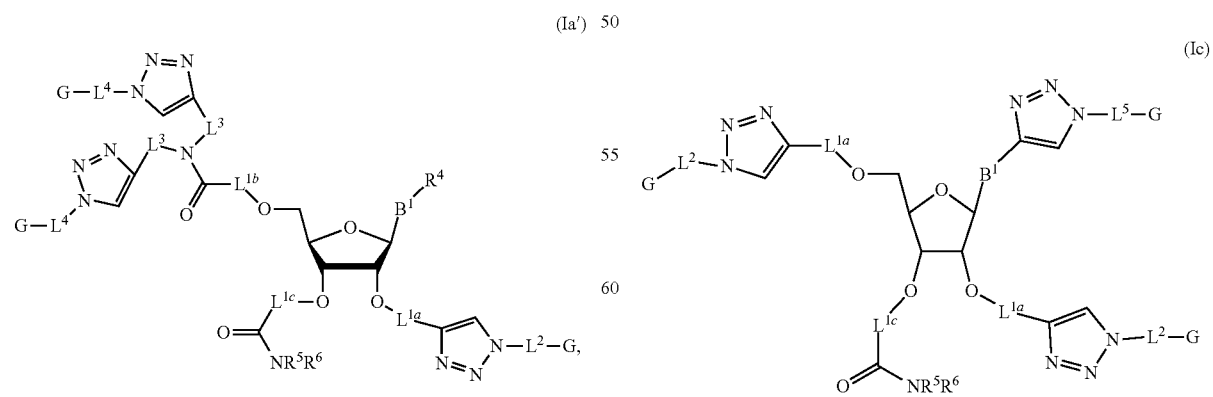

(Ic)

-continued

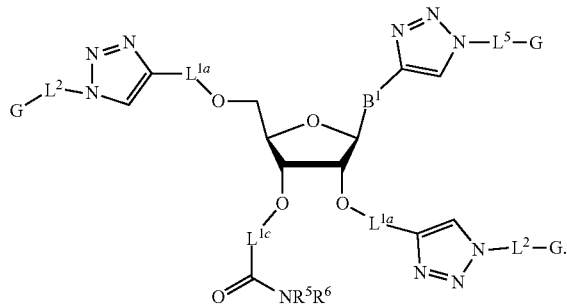
(Ic')

Some aspect of the present disclosure relates to compounds of Formula (II):

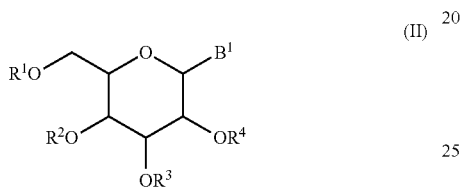
(II)

wherein:
each of $R^1$, $R^2$, $R^3$ and $R^4$ is independently -$L^{1a}$-Z-$L^2$-G, or -$L^{1b}$-C(=O)$NR^5R^6$;
wherein one of $R^1$, $R^2$, $R^3$, and $R^4$ is -$L^{1b}$-C(=O)$NR^5R^6$ and the others of $R^1$, $R^2$, $R^3$, and $R^4$ are not -$L^{1b}$-C(=O)$NR^5R^6$;
each $R^5$ is independently

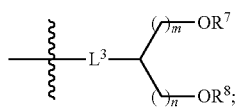

each of m and n is independently 0, 1, 2 or 3;
$R^6$ is H or $C_1$-$C_6$ alkyl;
$R^7$ is a hydroxy protecting group;
$R^8$ is hydrogen, a hydroxy protecting group, a phosphoramidite moiety, —C(=O)$CH_2CH_2$C(=O)$R^{8A}$, or —P(O$R^{8B}$)$NR^{8C}R^{8D}$;
$R^{8A}$ is —OH, —$OR^9$ or —$NR^{10}R^{11}$;
each of $R^{8B}$, $R^{8C}$ and $R^{8D}$ is independently H, $C_{1-6}$ haloalkyl, or unsubstituted or substituted $C_{1-6}$ alkyl;
$R^9$ is unsubstituted or substituted $C_{1-6}$ alkyl, or a hydroxy protecting group;
each of $R^{10}$ and $R^{11}$ is independently H, unsubstituted or substituted $C_{1-6}$ alkyl, or an amino protecting group;
each of $L^{1a}$ and $L^{1b}$ is independently optionally substituted $C_{1-10}$ alkylene, optionally substituted $C_2$-$C_{10}$ alkenylene, or optionally substituted 2 to 15 membered heteroalkylene, where one or more carbon atoms are replaced with C(=O), O, S or N;
each $L^2$ is independently optionally substituted $C_{1-10}$ alkylene, optionally substituted $C_2$-$C_{10}$ alkenylene, or optionally substituted 2 to 15 membered heteroalkylene wherein one or more carbon atoms are replaced with C(=O), O, S or N; or $C_1$-$C_{10}$ alkylene or 2 to 15 membered heteroalkylene each independently interrupted by a ring or ring system selected from the group consisting of optionally substituted $C_6$-$C_{10}$ arylene, optionally substituted $C_3$-$C_{10}$ cycloalkylene, optionally substituted five to ten membered heteroarylene, and optionally substituted three to ten membered heterocyclylene;
$L^3$ is an optionally substituted $C_{1-10}$ membered alkylene, optionally substituted $C_2$-$C_{10}$ alkenylene, or optionally substituted 2 to 15 membered heteroalkylene where one or more carbon atoms are replaced with C(=O), O, S or N;
each Z is a triazole ring, or a bi-, tri-, or tetracyclic ring system having a fused triazole ring;
$B^1$ is H, hydroxy, a protected hydroxy, a natural nucleobase, a modified natural nucleobase, or an unnatural nucleobase;
G is

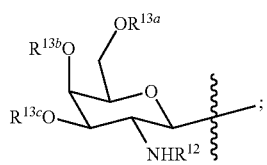

$R^{12}$ is —C(=O)$C_{1-6}$ alkyl, —C(=O)$C_{1-6}$ haloalkyl, or —C(=O)phenyl; and
each of $R^{13a}$, $R^{13b}$ and $R^{13c}$ is independently hydrogen, benzyl (Bn), or —C(=O)$R^{13A}$, wherein $R^{13A}$ is $C_{1-6}$ alkyl, $C_{1-6}$ haloalkyl, or optionally substituted phenyl;
provided that the compound has three or more G groups.

In some embodiments, compounds of Formula (II) have the structure of Formula (IIa):

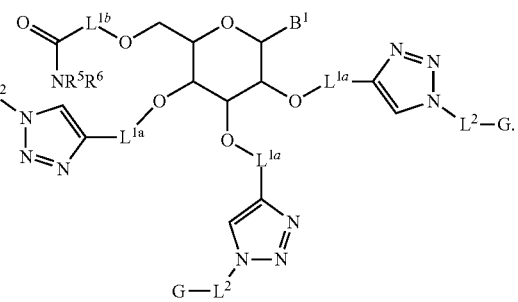
(IIa)

A further aspect of the present disclosure relates to a solid support comprising a compound described herein of Formula (I), (Ia), (Ia'), (Ib), (Ib'), (Ic), (Ic'), (II), or (IIa), covalently attached thereto via $R^8$. In some embodiments, $R^8$ is —C(=O)$CH_2CH_2$C(=O)OH. In other embodiments, $R^8$ is —C(=O)$CH_2CH_2$C(=O)$NH_2$. In further embodiments, the compound is covalently attached to the solid support via a moiety:

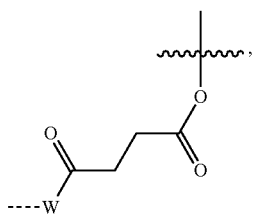

wherein W is O or NH; wherein the dashed line refers to the connection with the solid support, optionally through an additional linker, and wherein the squiggly line refers to the point of the attachment of the oxygen atom that covalently attached to $R^8$ of the compound, to the remaining portion of the compound.

Additional aspect of the present disclosure relates to a method of preparing a synthetic oligonucleotide, comprising reacting a compound described herein of Formula (I), (Ia), (Ia'), (Ib), (Ib'), (Ic), (Ic'), (II), or (IIa) with an oligonucleotide. In some embodiments, the oligonucleotide may have a 1 to 100 nucleobase length. In some embodiments, the reaction may be conducted on a solid support.

DETAILED DESCRIPTION

The compounds disclosed herein relate to novel functionalized GalNAc analogs to provide novel methods for oligonucleotide delivery. In some embodiments, the functionalized GalNAc analogs disclosed herein may contain a phosphoramidite moiety that allows for the incorporation of the GalNAc analogs to the 5' end or any internal position of an oligonucleotide. In some other embodiments, the functionalized GalNAc analogs disclosed herein may contain a succinate moiety that allows for the incorporation of the GalNAc analogs on a solid support, which can introduce GalNAc analogs described herein to the 3' end of oligonucleotide.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together" it means that they are covalently bonded to one another to form a ring:

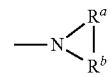

Whenever a group is described as being "optionally substituted" that group may be unsubstituted or substituted with one or more of the indicated substituents. Likewise, when a group is described as being "substituted", the substituent may be selected from one or more of the indicated substituents. If no substituents are indicated, it is meant that the indicated "optionally substituted" or "substituted" group may be one or more group(s) individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (for example, $C_3$-$C_8$cycloalkyl, $C_3$-$C_8$ cycloalkenyl, or $C_3$-$C_8$ cycloalkynyl, each may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heterocyclyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); aryl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heteroaryl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, or —O($C_1$-$C_6$ alkoxy)$C_1$-$C_6$ alkyl); (5-10 membered heteroaryl)$C_1$-$C_6$ alkyl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, iodo); cyano; hydroxy; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy such as —$OCF_3$); ($C_1$-$C_6$ alkoxy)$C_1$-$C_6$ alkyl; —O($C_1$-$C_6$ alkoxy) $C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, NH($C_1$-$C_6$ alkyl); di-substituted amino (for example, N($C_1$-$C_6$ alkyl)$_2$); oxo (=O); and thioxo (=S).

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro [3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene and propylene. When an alkylene is interrupted by a ring or ring system described herein, it means the ring or ring system is either inserted into a single covalent bond between two carbon atoms in the alkylene, or the ring or ring system is added to one terminal of the alkylene. For example, when a $C_2$ alkylene is interrupted by a phenylene, it can encompass the following structures: —$CH_2$-Ph-$CH_2$— or -Ph-$CH_2CH_2$—.

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2$-$C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom (N), oxygen atom (S) or sulfur atom (S)). For example, a —$CH_2$— may be replaced with —O—, —S—, or —NH—. Heteroalkylene groups include, but are not limited to ether, thioether, aminoalkylene, and alkylene-amino-alkylene moieties. In some embodiments, the heteroalkylene may include one, two, three, four, or five —$CH_2CH_2O$— unit(s). Alternatively and/or additionally, one or more carbon atoms can also be substituted with an oxo (═O) to become a carbonyl. For example, a —$CH_2$— may be replaced with —C(═O)—. It is understood that when a carbon atom is replaced with a carbonyl group, it refers to the replacement of —$CH_2$— with —C(═O)—. When a carbon atom is replaced with a nitrogen atom, it refers to the replacement of —CH— with —N—. When a carbon atom is replaced with an oxygen or sulfur atom, it refers to the replacement of —$CH_2$— with —O— or —S—. When a heteroalkylene is interrupted by a ring or ring system described herein, it means the ring or ring system is either inserted into a single covalent bond (e.g., between two carbon atoms, or between a carbon atom and a heteroatom) in the heteroalkylene, or the ring or ring system is added to one terminal of the heteroalkylene. For example, when a —$CH_2$—O—$CH_2$— is interrupted by a phenylene, it can encompass the following structures: —$CH_2$-Ph-$OCH_2$— or -Ph-$CH_2OCH_2$—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl group, as defined herein. A non-limiting list of alkoxy group includes methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atom is replaced by a substituent. The term "di-substituted amino group" as used herein refers to an amino (—$NH_2$) group where each of the two hydrogen atoms is replaced by a substituent. The term "optionally substituted amino," as used herein refer to a —$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "—$NR_AR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(═O)O—" group in which R can be hydrogen, alkyl, alkenyl, alkynyl, carbocyclyl, aryl, heteroaryl, heterocyclyl, aralkyl, or heterocyclyl (alkyl), as defined herein. An O-carboxy may be substituted or unsubstituted.

The terms "ester" and "C-carboxy" refer to a "—C(=O) OR" group in which R can be the same as defined with respect to O-carboxy. An ester or C-carboxy may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R)$—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—$SO_2N(R_AR_B)$" group in which $R_A$ and $R_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N ($R_AR_B$)" group in which $R_A$ and $R_B$ can be the same as defined with respect to S-sulfonamido. An O-carbamyl may be substituted or unsubstituted.

An "N-carbamyl" group refers to an "ROC(=O)N ($R_A$)—" group in which R and $R_A$ can be the same as defined with respect to N-sulfonamido. An N-carbamyl may be substituted or unsubstituted.

An "O-thiocarbamyl" group refers to a "—OC(=S)—N ($R_AR_B$)" group in which $R_A$ and $R_B$ can be the same as defined with respect to S-sulfonamido. An O-thiocarbamyl may be substituted or unsubstituted.

An "N-thiocarbamyl" group refers to an "ROC(=S)N ($R_A$)—" group in which R and $R_A$ can be the same as defined with respect to N-sulfonamido. An N-thiocarbamyl may be substituted or unsubstituted.

A "C-amido" group refers to a "—C(=O)N($R_AR_B$)" group in which $R_A$ and $R_B$ can be the same as defined with respect to S-sulfonamido. A C-amido may be substituted or unsubstituted.

An "N-amido" group refers to a "RC(=O)N($R_A$)—" group in which R and $R_A$ can be the same as defined with respect to N-sulfonamido. An N-amido may be substituted or unsubstituted.

Where the numbers of substituents are not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

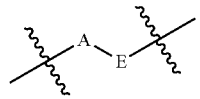

includes the substituent being oriented such that the A is attached at the leftmost attachment point of the molecule as well as the case in which A is attached at the rightmost attachment point of the molecule. In addition, if a group or substituent is depicted as

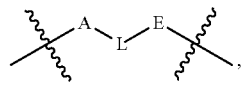

and when L is defined as a bond or absent; such group or substituent is equivalent to

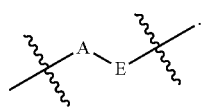

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

Examples of hydroxy protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl) xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of protecting groups commonly used to protect phosphate and phosphorus hydroxy groups include without limitation, methyl, ethyl, benzyl (Bn), phenyl, isopropyl, tert-butyl, allyl, cyclohexyl (cHex), pivaloyloxymethyl (—CH$_2$—O—C(=O)C(CH$_3$)$_3$, or POM), 4-methoxybenzyl, 4-chlorobenzyl, 4-nitrobenzyl, 4-acyloxybenzyl, 2-methylphenyl, 2,6-dimethylphenyl, 2-chlorophenyl, diphenylmethyl, 4-methylthio-1-butyl, 2-(S-Acetylthio) ethyl (SATE), 2-cyanoethyl, 2-cyano-1,1-dimethylethyl (CDM), 4-cyano-2-butenyl, 2-(trimethylsilyl)ethyl (TSE), 2-(phenylthio)ethyl, 2-(triphenylsilyl)ethyl, 2-(benzylsulfonyl)ethyl, 2,2,2-trichloroethyl, 2,2,2-tribromoethyl, 2,3-dibromopropyl, 2,2,2-trifluoroethyl, thiophenyl, 2-chloro-4-tritylphenyl, 2-bromophenyl, 2-[N-isopropyl-N-(4-methoxybenzoyl)amino]ethyl, 4-(N-trifluoroacetylamino) butyl, 4-oxopentyl, 4-tritylaminophenyl, 4-benzylaminophenyl and morpholino. Wherein more commonly used phosphate and phosphorus protecting groups include without limitation, methyl, ethyl, benzyl (Bn), phenyl, isopropyl, tert-butyl, 4-methoxybenzyl, 4-chlorobenzyl, 2-chlorophenyl, 2-cyanoethyl and POM.

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry,* 2d ed., Francis Carey (1992), pages 328-331; *Introduction to Organic Chemistry,* 2d ed., Andrew Streitwieser and Clayton Heathcock (1981), pages 169-171; and *Organic Chemistry,* 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a trifluoroacetate salt.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N—9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide is described as "comprising" or "incorporating" a nucleoside compound described herein, it means that the nucleoside described herein forms a covalent bond with the oligonucleotide. In some embodiments, the covalent bond is formed by the reaction of the 5' hydroxy group of the nucleoside of Formula (I) as described herein and the 3' phosphoramidite group of another nucleoside (which may be the terminal nucleoside of an oligonucleoside) to form a phosphodiester bond, or the reaction of the 3' phosphoramidite group of the nucleoside of Formula (I) as described herein with the 5' hydroxy group of another nucleoside (which may be the terminal nucleoside of an oligonucleoside) to form a phosphodiester bond or an equivalent thereof (e.g., thiophosphodiester).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

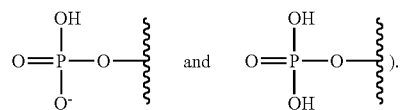 [SMILES: *OP(=O)([O-])O ; *OP(=O)(O)O]

As used herein, the terms "monophosphate," "diphosphate," and "triphosphate" are used in their ordinary sense as understood by those skilled in the art and include protonated forms.

GalNAc Analogs of Formula (I)

Some embodiments of the present disclosure provide a compound of Formula (I), or a pharmaceutically acceptable salt thereof:

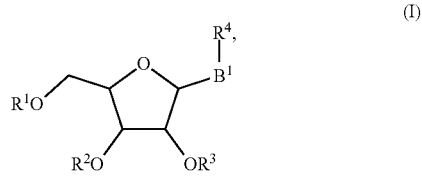

wherein:
each of $R^1$, $R^2$, $R^3$ and $R^4$ is independently -$L^{1a}$-Z-$L^2$-G, or -$L^{1b}$-C(=O)N$R^5R^6$;
wherein one of $R^1$, $R^2$, $R^3$, and $R^4$ is -$L^{1b}$-C(=O)N$R^5R^6$ and the others of $R^1$, $R^2$, $R^3$, and $R^4$ are not -$L^{1b}$-C(=O)N$R^5R^6$;
each $R^5$ is independently

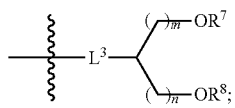

each of m and n is independently 0, 1, 2 or 3;
$R^6$ is H or $C_1$-$C_6$ alkyl;
$R^7$ is a hydroxy protecting group;
$R^8$ is hydrogen, a hydroxy protecting group, a phosphoramidite moiety, —C(=O)CH$_2$CH$_2$C(=O)$R^{8A}$, or —P(O$R^{8B}$)N$R^{8C}R^{8D}$;
$R^{8A}$ is —OH, —O$R^9$ or —N$R^{11}$;
each of $R^{8B}$, $R^{8C}$ and $R^{8D}$ is independently H, $C_{1-6}$ haloalkyl, or unsubstituted or substituted $C_{1-6}$ alkyl;
$R^9$ is unsubstituted or substituted $C_{1-6}$ alkyl, or a hydroxy protecting group;
each of $R^{10}$ and $R^{11}$ is independently H, unsubstituted or substituted $C_{1-6}$ alkyl, or an amino protecting group;
each of $L^{1a}$ and $L^{1b}$ is independently optionally substituted $C_{1-10}$ alkylene, optionally substituted $C_2$-$C_{10}$ alkenylene, or optionally substituted 2 to 15 membered heteroalkylene, where one or more carbon atoms are replaced with C(=O), O, S or N;
each $L^2$ is independently optionally substituted $C_{1-10}$ alkylene, optionally substituted $C_2$-$C_{10}$ alkenylene, or optionally substituted 2 to 15 membered heteroalkylene wherein one or more carbon atoms are replaced with C(=O), O, S or N; or $C_1$-$C_{10}$ alkylene or 2 to 15 membered heteroalkylene each independently interrupted by a ring or ring system selected from the group consisting of optionally substituted $C_6$-$C_{10}$ arylene, optionally substituted $C_3$-$C_{10}$ cycloalkylene, optionally substituted five to ten membered heteroarylene, and optionally substituted three to ten membered heterocyclylene;
$L^3$ is an optionally substituted $C_{1-10}$ membered alkylene, optionally substituted $C_2$-$C_{10}$ alkenylene, or optionally substituted 2 to 15 membered heteroalkylene where one or more carbon atoms are replaced with C(=O), O, S or N;
each Z is a triazole ring, or a bi-, tri-, or tetracyclic ring system having a fused triazole ring;
$B^1$ is H, hydroxy, a protected hydroxy, a natural nucleobase, a modified natural nucleobase, or an unnatural nucleobase;
G is

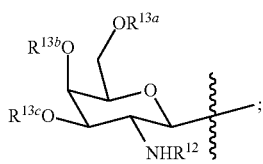

$R^{12}$ is —C(=O)$C_{1-6}$ alkyl, —C(=O)$C_{1-6}$ haloalkyl, or —C(=O)phenyl; and each of $R^{13a}$, $R^{13b}$ and $R^{13c}$ is independently hydrogen, benzyl (Bn), or —C(=O)$R^{13A}$, wherein $R^{13A}$ is $C_{1-6}$ alkyl, $C_{1-6}$ haloalkyl, or optionally substituted phenyl;
provided that the compound has at least three G groups.

In some embodiments of Formula (I), the compound has three G groups. In other embodiments of Formula (I), the compound has more than three G group. In some such embodiments, the compound has four, five, six, or seven G groups.

In some embodiments of Formula (I), each of $R^1$, $R^2$ and $R^3$ is independently -$L^{1a}$-Z-$L^2$-G, and $R^4$ is -$L^{1c}$-C(=O)N$R^5R^6$. In some embodiments, $R^1$ is -$L^{1b}$-C(=O)N$R^AR^B$, $R^2$ is -$L^{1c}$-C(=O)N$R^5R^6$, $R^3$ is -$L^{1a}$-Z-$L^2$-G, and $R^4$ is H. In other embodiments, each of $R^1$ and $R^3$ is independently -$L^{1a}$-Z-$L^2$-G, $R^2$ is -$L^{1b}$-C(=O)N$R^5R^6$, and $R^4$ is —Z-$L^5$-G. In yet other embodiments, $R^1$ is -$L^{1c}$-C(=O)N$R^5R^6$, $R^2$ is -$L^{1b}$-C(=O)N$R^AR^B$, $R^3$ is -$L^{1a}$-Z-$L^2$-G, and $R^4$ is H. In some embodiments, $R^1$ is -$L^{1a}$-Z-$L^2$-G, $R^2$ is -$L^{1c}$-C(=O)N$R^5R^6$, $R^3$ is -$L^1$b-C(=O)N$R^AR^B$, and $R^4$ is H. In other embodiments, $R^1$ is -$L^{1c}$-C(=O)N$R^5R^6$, $R^2$ is -$L^{1a}$-Z-$L^2$-G, $R^3$ is -$L^{1a}$-Z-$L^2$-G, and $R^4$ is —Z-$L^5$-G. In yet other embodiments, $R^1$ is -$L^{1a}$-Z-$L^2$-G, $R^2$ is -$L^{1c}$-C(=O)N$R^5R^6$, $R^3$ is -$L^{1a}$-Z-$L^2$-G and $R^4$ is —Z-$L^5$-G. In still yet other such embodiments, $R^1$ is -$L^{1a}$-Z-$L^2$-G, $R^2$ is -$L^{1a}$-Z-$L^2$-G, $R^3$ is -$L^{1c}$C(=O)N$R^5R^6$, and $R^4$ is —Z-$L^5$-G.

In some embodiments of the compound of Formula (I), each Z is independently

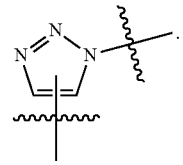

In some such embodiments, each Z is independently

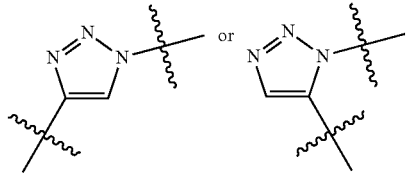 [SMILES: *c1cn(*)nn1 ; *c1cnnn1*]

In other embodiments, each Z is independently

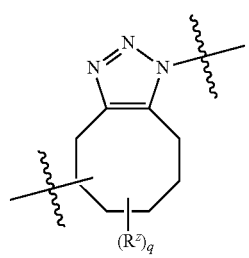

q is an integer from 0 to 6; each $R^z$ is independently halo or $C_{1-6}$ haloalkyl, or any two adjacent $R^z$ taken together with the atoms to which they are attached form an optionally substituted $C_{6-10}$ aryl, optionally substituted 5-10 membered heteroaryl, optionally substituted $C_{3-7}$ cycloalkyl, or optionally substituted 3 to 10 membered heterocyclyl. Alternatively, the cyclooctene ring fused to the triazole ring may contain one or more heteroatoms, for example, O, N or S. In some such embodiments, q is 1 or 2; and each $R^z$ is halo. In another such embodiment, each Z is independently

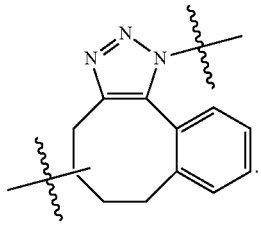

In yet another embodiment, each Z is independently

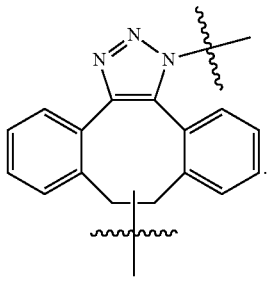

In yet another embodiment, each Z is

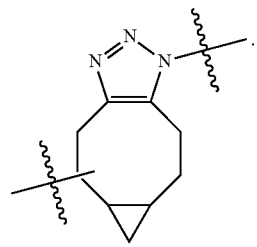

In some embodiments, the compound of Formula (I) has the Formula (Ia) or (Ia'):

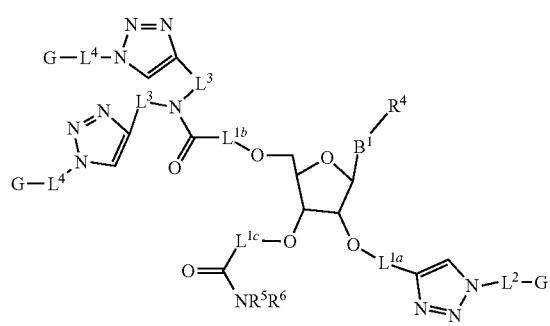

(Ia)

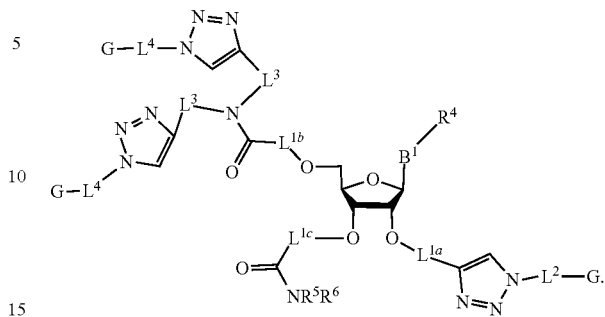

(Ia'), wherein $R^4$ is H

In some embodiments, the compound of Formula (I) has the Formula (Ib) or (Ib'):

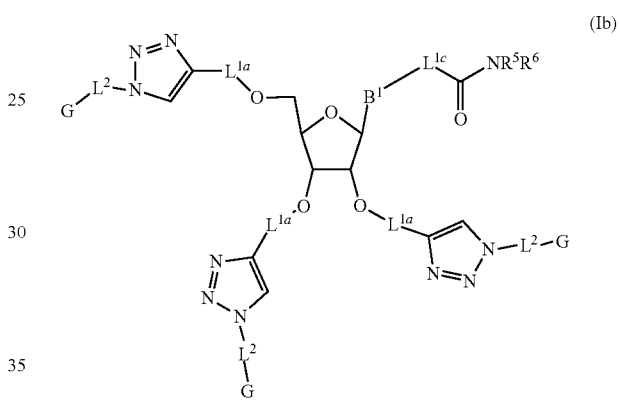

(Ib)

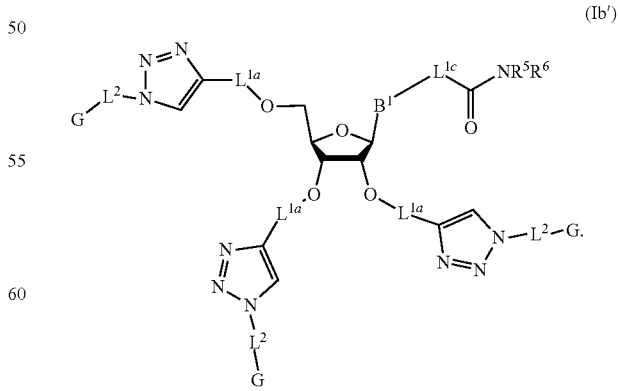

(Ib')

In some embodiments, the compound of Formula (I) has the Formula (Ic) or (Ic'):

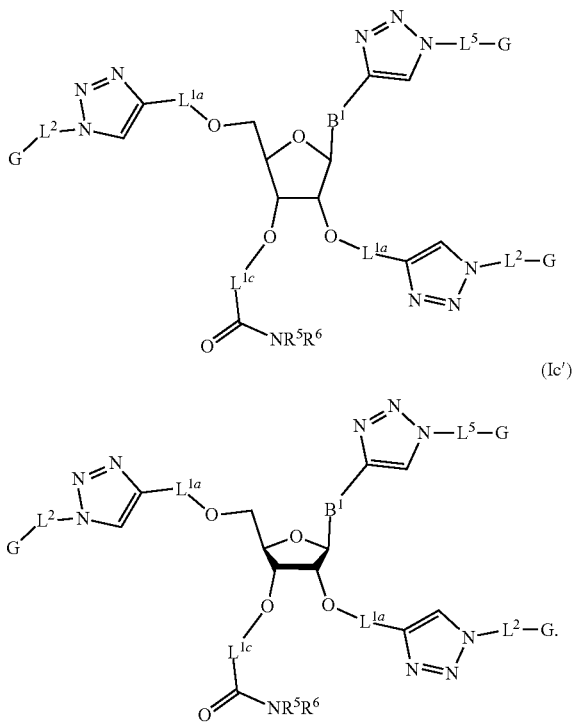

(Ic)

(Ic')

In some embodiments of Formula (I), (Ia), (Ia'), (Ib), (Ib'), (Ic), or (Ic'), each $L^{1a}$ and $L^{1b}$ is independently $C_{1-10}$ alkylene. In some such embodiments, each $L^{1a}$ and $L^{1b}$ is —CH$_2$—, —(CH$_2$)$_2$—, or —(CH$_2$)$_3$—. In some embodiments of Formula (I), (Ia), (Ia'), (Ib), (Ib'), (Ic), or (Ic'), $L^{1c}$ is $C_{1-10}$ alkylene. In some such embodiments, $L^{1c}$ is —CH$_2$—, —(CH$_2$)$_2$—, or —(CH$_2$)$_3$—. In other embodiments of Formula (I), $L^{1c}$ is $C_{2-10}$ alkenylene. In some such embodiments, $L^{1c}$ is —CH=CH— or —CH$_2$CH=CH—. In some embodiments of Formula (I), (Ia), (Ia'), (Ib), (Ib'), (Ic), or (Ic'), each $L^{1a}$ and $L^{1b}$ is independently —CH$_2$—, —(CH$_2$)$_2$—, or —(CH$_2$)$_3$— and $L^{1c}$ is —CH$_2$—. In some embodiments of Formula (I), (Ia), (Ia'), (Ib), (Ib'), (Ic), or (Ic'), each $L^{1a}$ and $L^{1b}$ is $C_{1-10}$ alkylene and $L^{1c}$ is $C_{2-10}$ alkenylene. In some such embodiments, each $L^{1a}$ and $L^{1b}$ is independently —CH$_2$—, —(CH$_2$)$_2$—, or —(CH$_2$)$_3$— and $L^{1c}$ is —CH=CH— or —CH$_2$CH=CH—. In some embodiments of Formula (I), (Ia), (Ia'), (Ib), (Ib'), (Ic), or (Ic'), $L^3$ is —C$_{1-10}$ alkylene. In some such embodiments, $L^3$ is —CH$_2$—. In some embodiments of Formula (I), (Ia), (Ia'), (Ib), (Ib'), (Ic), or (Ic'), each $L^{1a}$ and $L^{1b}$ is $C_{1-10}$ alkylene, $L^{1c}$ is $C_{2-10}$ alkenylene, and $L^3$ is $C_{1-10}$ alkylene. In some such embodiments, each $L^{1a}$ and $L^{1b}$ is independently —CH$_2$—, —(CH$_2$)$_2$—, or —(CH$_2$)$_3$—; $L^{1c}$ is —CH=CH— or —CH$_2$CH=CH—; and $L^3$ is —CH$_2$—(CH$_2$)$_2$—, or —(CH$_2$)$_3$—. In some embodiments of Formula (I), (Ia), (Ia'), (Ib), (Ib'), (Ic), or (Ic'), each $L^{1a}$ is independently 2 to 10 membered heteroalkylene, where one or more carbon atoms are replaced with C(=O), O, S or N. In some such embodiments, $L^{1a}$ is —CH$_2$—C(=O)NH—CH$_2$—.

In some embodiments of Formula (I), (Ia), (Ia'), (Ib), (Ib'), (Ic), or (Ic'), each of $L^2$, $L^4$ and $L^5$ is independently 2 to 15 membered heteroalkylene, for example heteroalkylene containing one, two, three, four, or five heteroatoms selected from O, S, N, C(=O) or C(=S). In some such embodiments, each of $L^2$, $L^4$ and $L^5$ is independently —(CH$_2$CH$_2$O)$_j$—, wherein j is 2, 3, 4, or 5.

In some embodiments of Formula (I), (Ia), (Ia'), (Ib), (Ib'), (Ic), or (Ic'), each of $R^{13a}$, $R^{13b}$, and $R^{13c}$ is —C(=O)CH$_3$. In some embodiments of Formula (I), (Ia), (Ia'), (Ib), (Ib'), (Ic), or (Ic'), $R^{12}$ is —C(=O)CH$_3$. In other embodiments, $R^{12}$ is —C(=O)CF$_3$. In some embodiments of Formula (I), each of $R^{13a}$, $R^{13b}$, and $R^{13c}$ is —C(=O)CH$_3$, and $R^{12}$ is —C(=O)CH$_3$.

In some embodiments of Formula (I), (Ia), (Ia'), (Ib), (Ib'), (Ic), or (Ic'), $L^6$ is an $C_{1-10}$ membered alkylene. In some such embodiments, $L^6$ is —CH$_2$—, —(CH$_2$)$_2$—, —(CH$_2$)$_3$—, or —(CH$_2$)$_4$—. In some embodiments, m is 0. In other embodiments, m is 1. In some embodiments, m is 2. In some embodiments, m is 3. In some embodiments of Formula (I), (Ia), (Ia'), (Ib), (Ib'), (Ic), or (Ic'), n is 0. In other embodiments, n is 1. In some embodiments, n is 2. In some embodiments, n is 3. In some embodiments of Formula (I), (Ia), (Ia'), (Ib), (Ib'), (Ic), or (Ic'), m is 0 and n is 1. In other embodiments, m is 1 and n is 0. In yet other embodiments, both m and n are 0. In still yet other embodiments, both m and n are 1.

In some embodiments of Formula (I), (Ia), (Ia'), (Ib), (Ib'), (Ic), or (Ic'), $R^7$ is a trityl type of hydroxy protecting group selected from (4-methoxyphenyl)diphenylmethyl, bis(4-methoxyphenyl)phenylmethyl (DMTr), tris(4-methoxyphenyl)methyl, 9-phenylxanthen-9-yl, or 9-(4-methoxyphenyl)xanthen-9-yl. In some specific embodiments, $R^7$ is bis(4-methoxyphenyl)phenylmethyl (DMTr).

In some embodiments of Formula (I), (Ia), (Ia'), (Ib), (Ib'), (Ic), or (Ic'), $R^8$ is —C(=O)CH$_2$CH$_2$C(=O)OH. In another embodiment, $R^8$ is —C(=O)CH$_2$CH$_2$C(=O)NH$_2$. In other embodiments, $R^8$ is or —P(OR$^{8B}$)NR$^{8C}$R$^{8D}$, wherein R$^{8B}$ is H or substituted $C_{1-6}$ alkyl, and each R$^{8C}$ and R$^{8D}$ is independently unsubstituted or substituted $C_{1-6}$ alkyl. In one embodiment, $R^8$ is

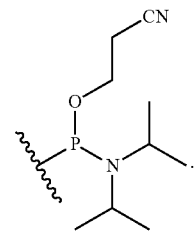 [SMILES: *P(OCCC#N)N(C(C)C)C(C)C]

In yet another embodiment, $R^8$ is H.

In some embodiments of Formula (I), $B^1$ is:

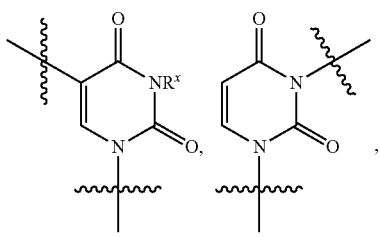

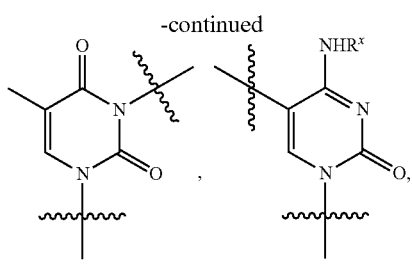
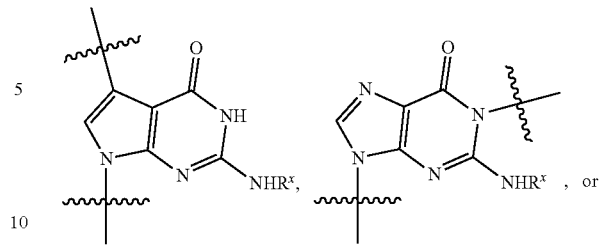
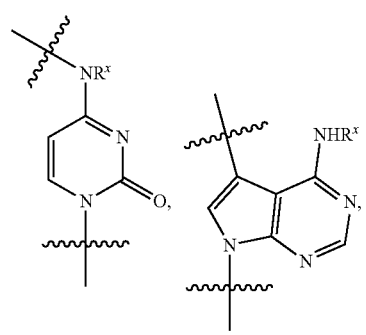
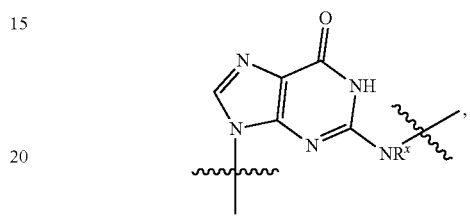
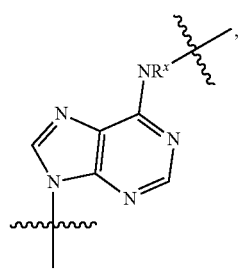
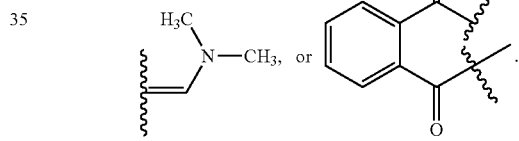
wherein $R^x$ is hydrogen or an amino protecting group, or the hydrogen in —$NHR^x$ is absent and R is a divalent amino protecting group. In some such embodiment, $R^x$ is H. In some such embodiments, $R^x$ is —C(=O)$C_{1-6}$ alkyl (e.g., —C(=O)$CH_3$). —$CH_2$-phenyl, or —C(=O)phenyl, or the hydrogen in —$NHR^x$ is absent and $R^x$ is
In some embodiments of Formula (I), the compound is:
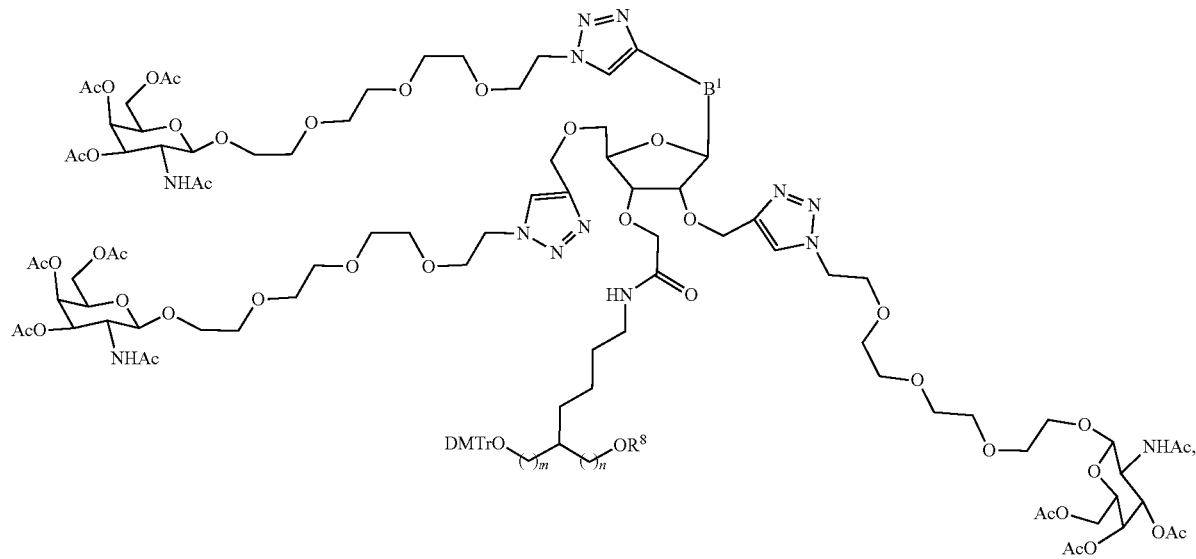

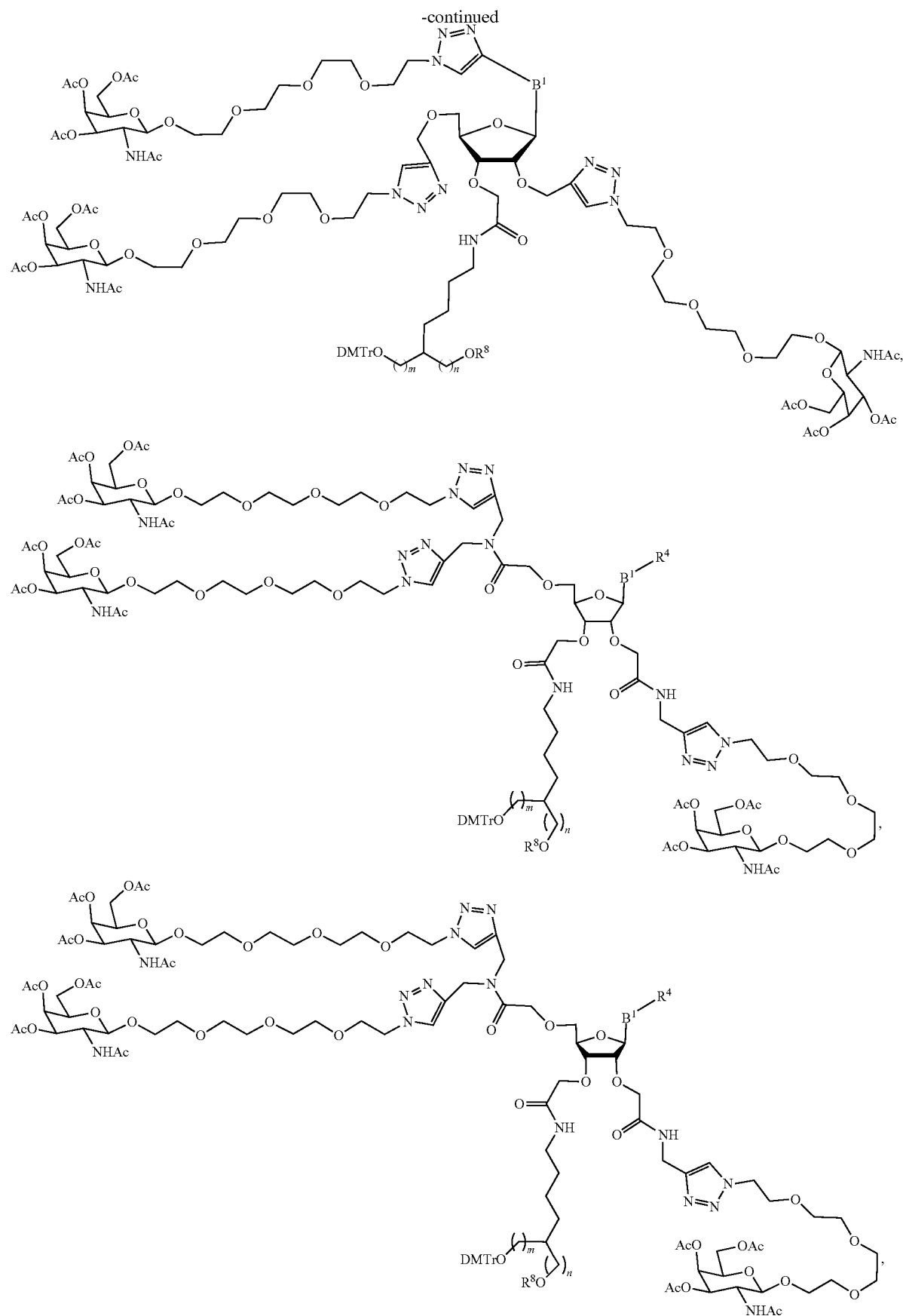

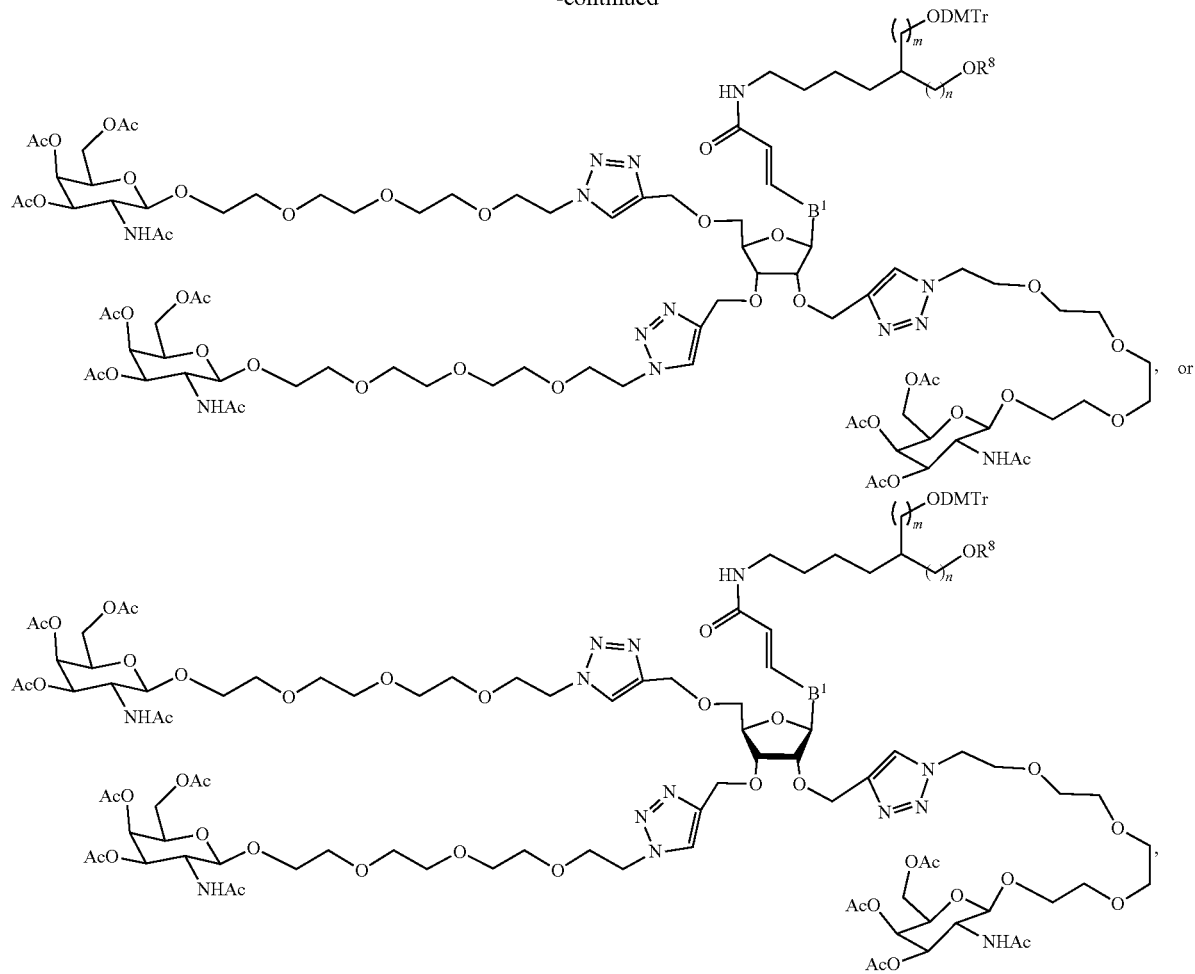
wherein $R^4$ is H. In one embodiment, m is 1 and n is 1. In another embodiment, m is 1 and n is 0. In another embodiment, m is 0 and n is 1. In some embodiments of Formula (I), B is:
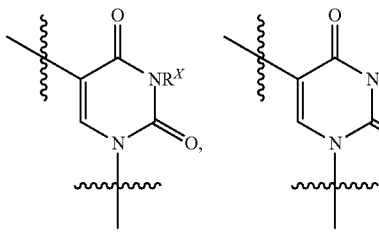
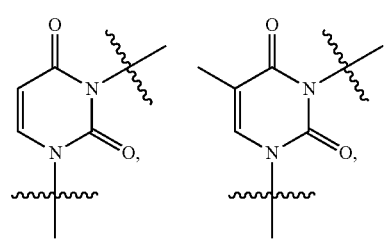
-continued
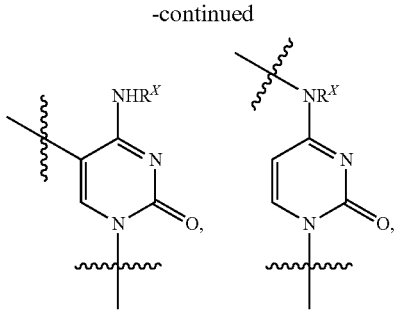
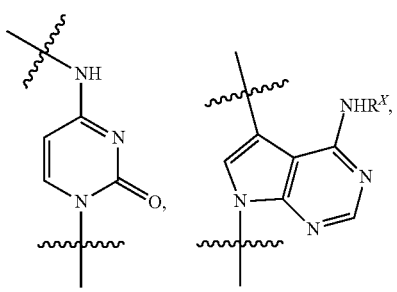

33
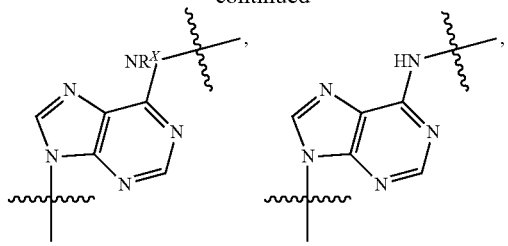
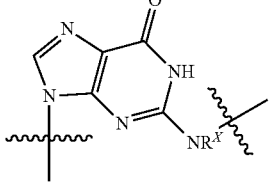
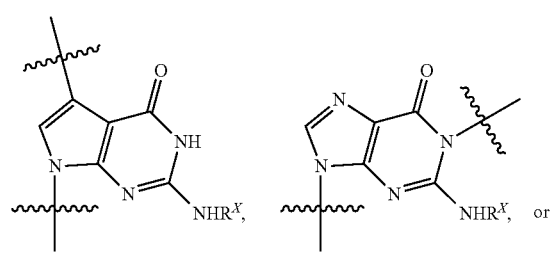
34
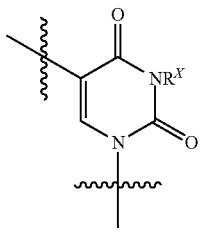
is hydrogen or an amino protecting group, or the hydrogen in —NHR$^x$ is absent and R$^x$ is a divalent amino protecting group. In further embodiments, B$^1$ is
and the compound is selected from the following structures:
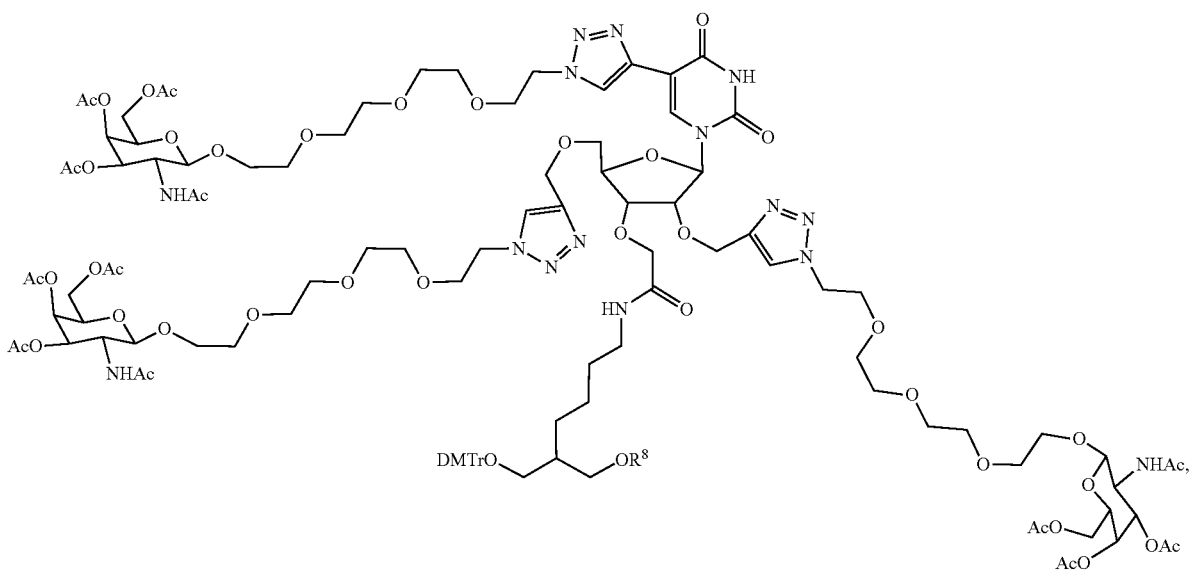

-continued
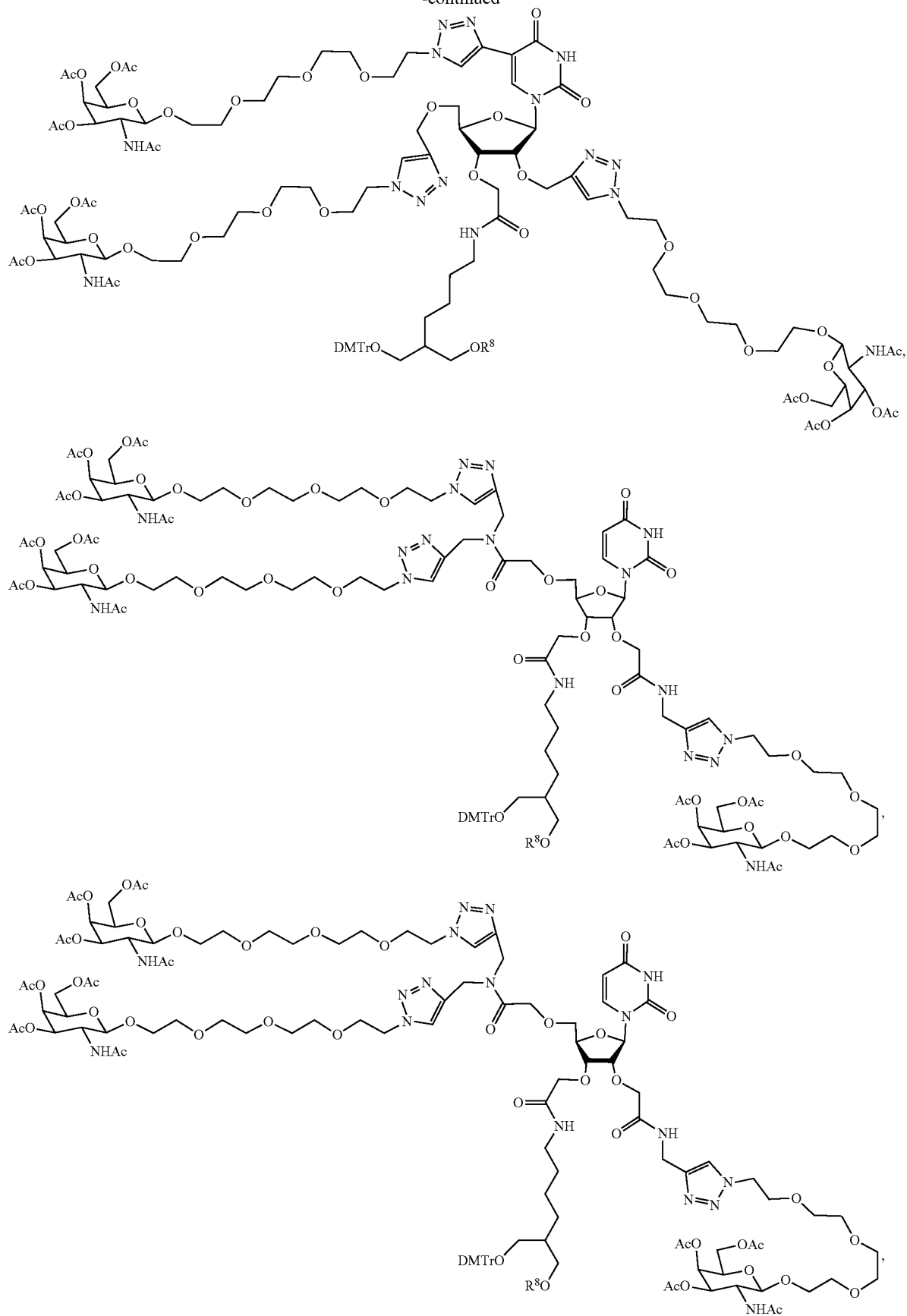

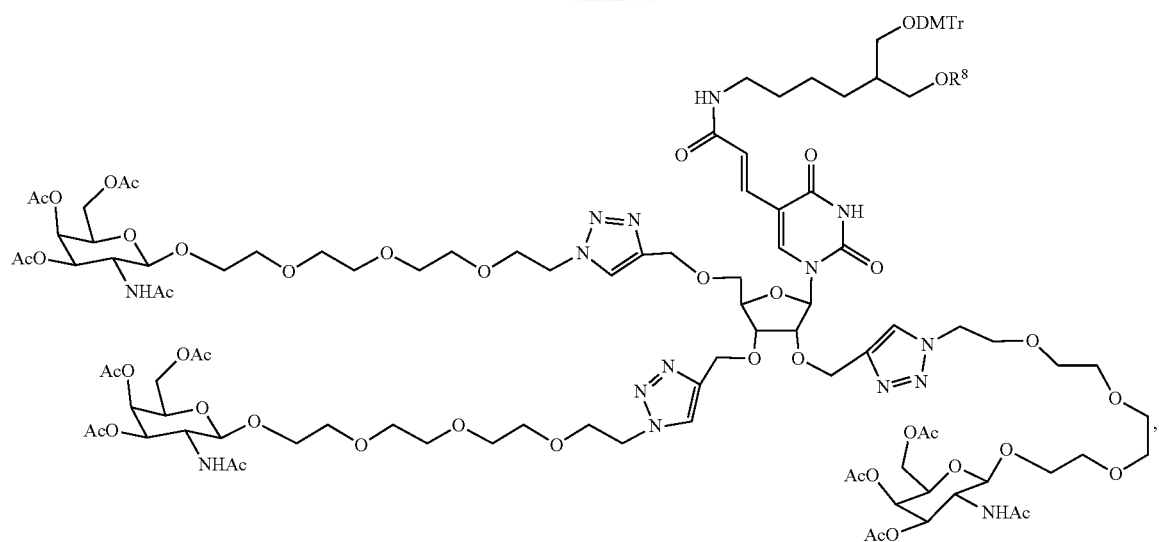
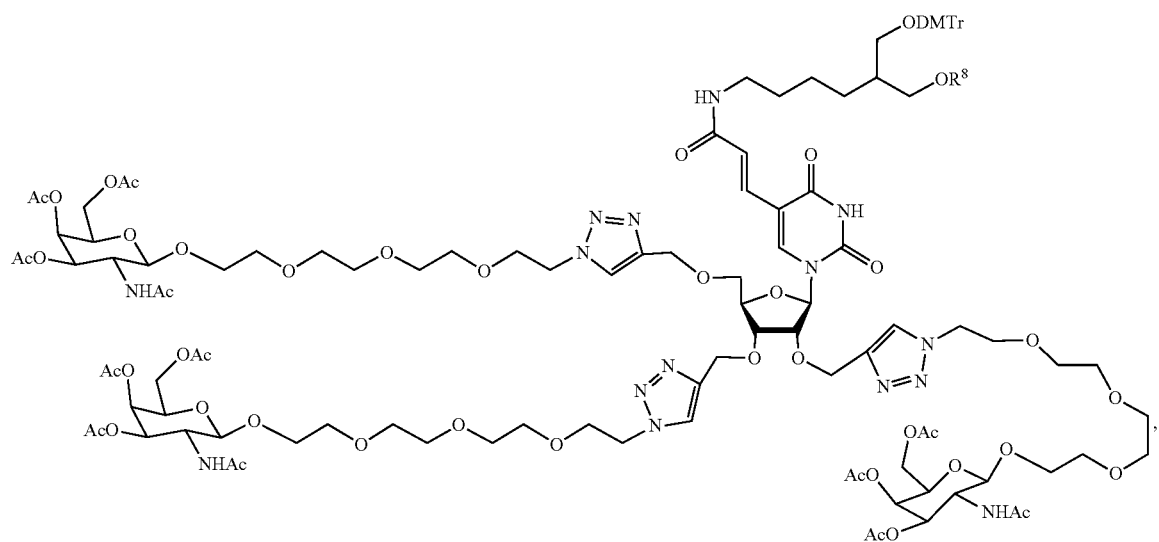
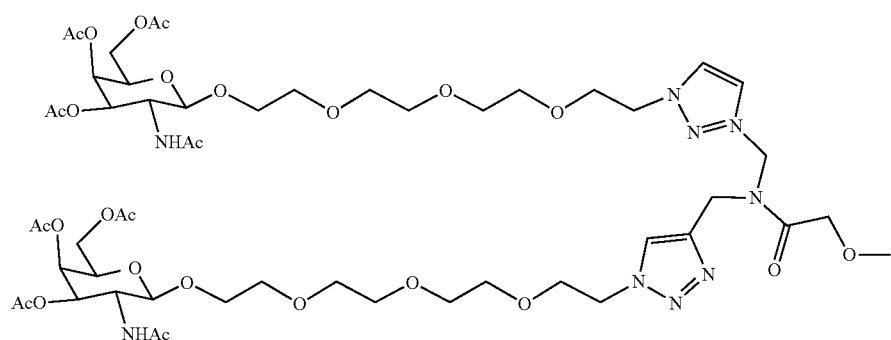

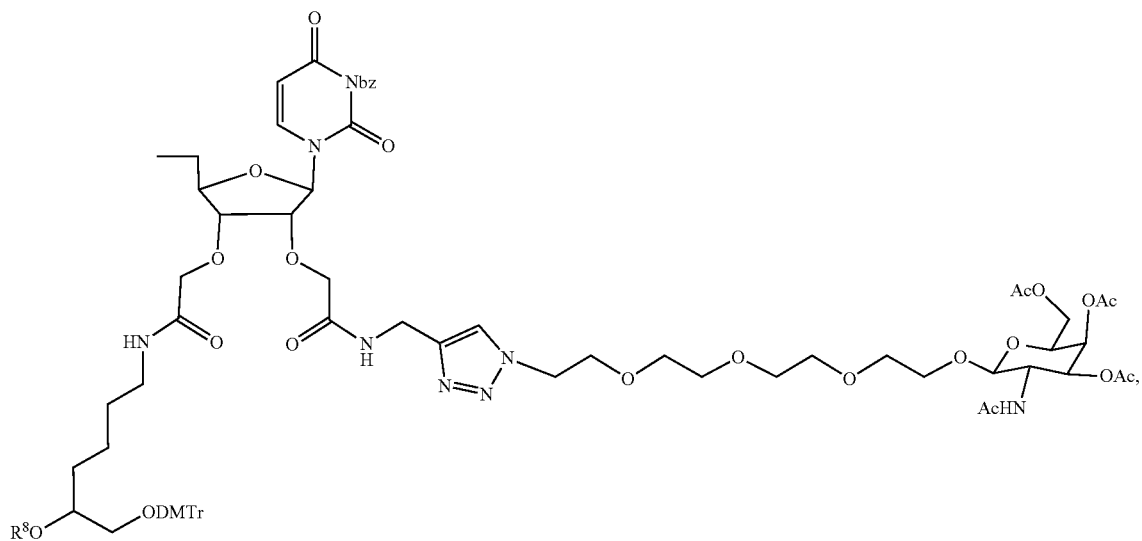
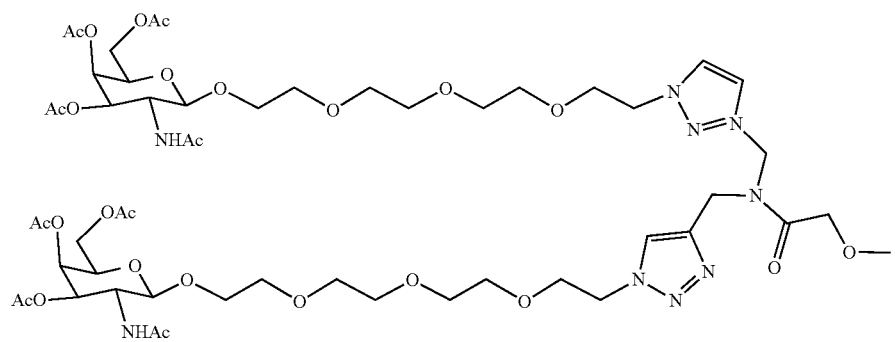
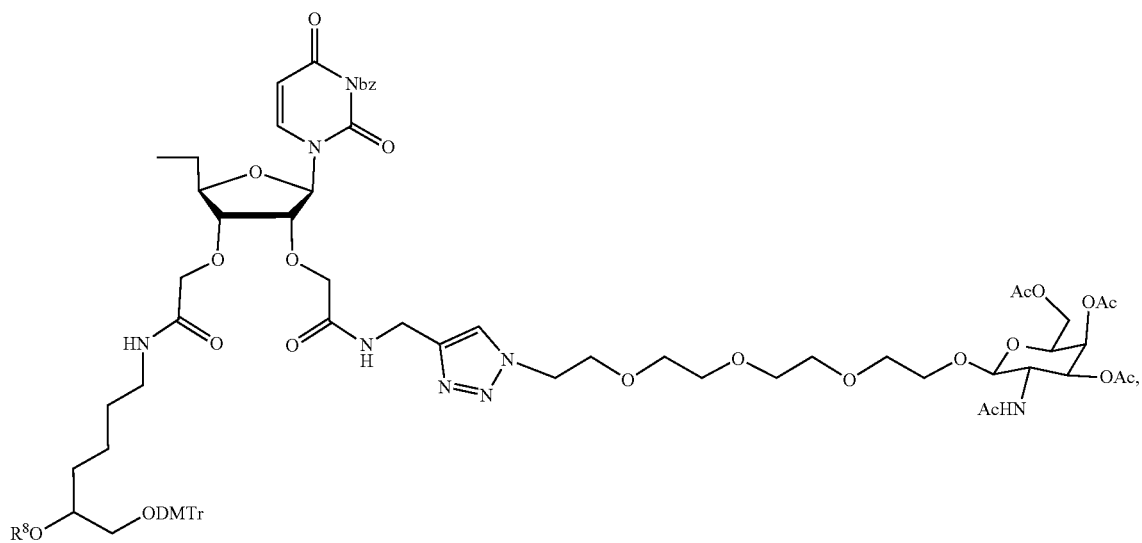

-continued
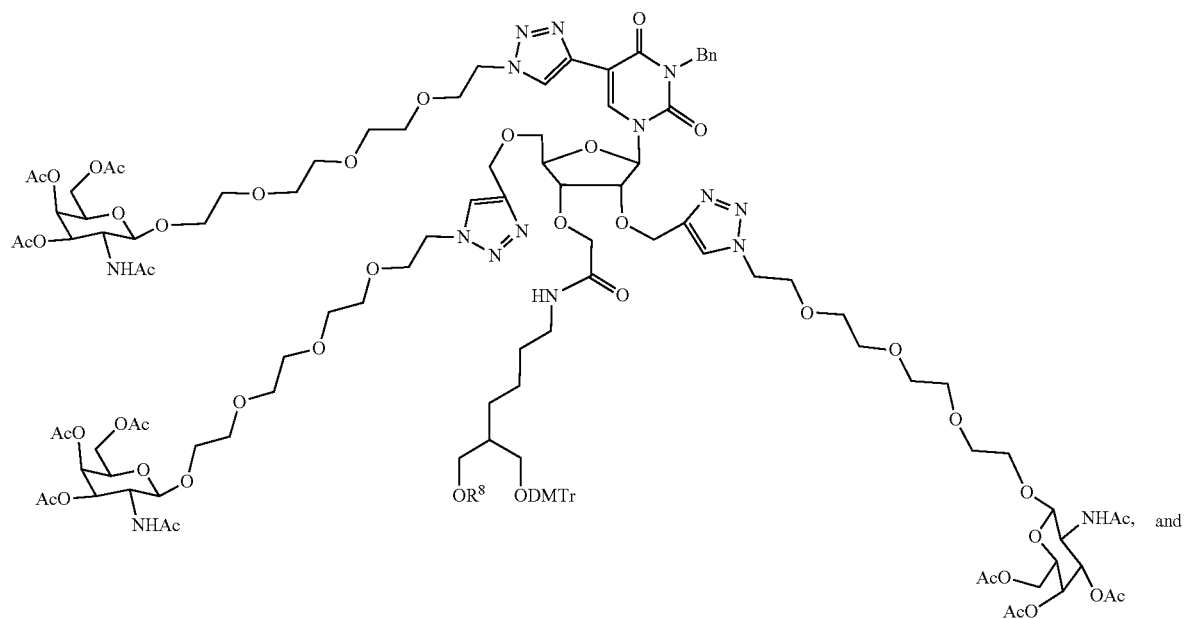
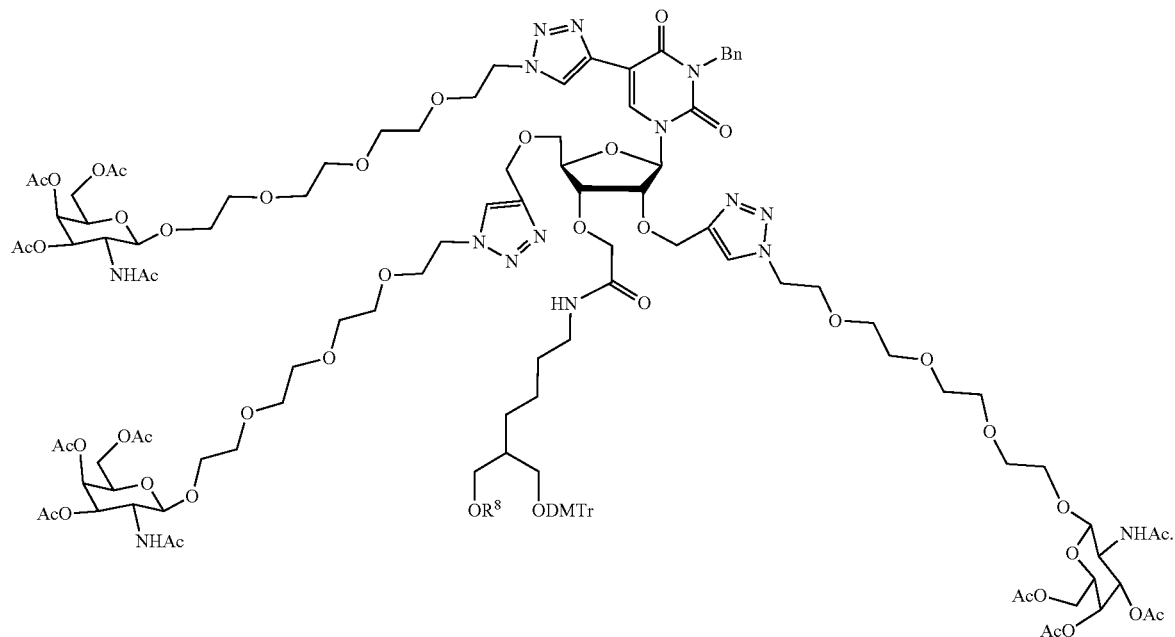

In some such embodiments, $R^8$ is —C(=O)CH$_2$CH$_2$C(=O)OH. In another such embodiment, $R^8$ is —C(=O)CH$_2$CH$_2$C(=O)NH$_2$. In other embodiments, $R^8$ is or —P(OR$^{8B}$)NR$^{8C}$R$^{8D}$, wherein R$^{8B}$ is H or substituted C$_{1-6}$ alkyl, and each R$^{8C}$ and R$^{8D}$ is independently unsubstituted or substituted C$_{1-6}$ alkyl. In one such embodiment, $R^8$ is

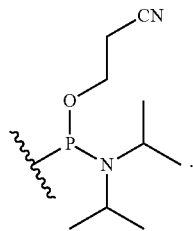

In another embodiment $R^8$ is H.

GalNAc Analogs of Formula (II)

Some embodiments of the present disclosure provide a compound of Formula (II), or a pharmaceutically acceptable salt thereof:

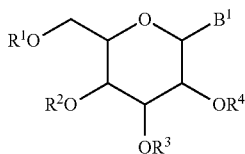

(II)

each of $R^1$, $R^2$, $R^3$ and R is independently -L$^{1a}$-Z-L -G, or -L$^{1b}$-C(=O)NR$^5$R$^6$;

wherein one of $R^1$, $R^2$, $R^3$, and $R^4$ is -L$^{1b}$-C(=O)NR$^5$R$^6$ and the others of $R^1$, $R^2$, $R^3$, and $R^4$ are not -L$^{1b}$-C(=O)NR$^5$R$^6$;

each $R^5$ is independently

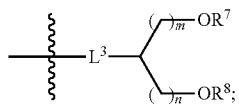

each of m and n is independently 0, 1, 2 or 3;
$R^6$ is H or C$_1$-C$_6$ alkyl;
$R^7$ is a hydroxy protecting group;
$R^8$ is hydrogen, a hydroxy protecting group, a phosphoramidite moiety, —C(=O)CH$_2$CH$_2$C(=O)R$^{8A}$, or —P(OR$^{8B}$)NR$^{8C}$R$^{8D}$;
$R^{8A}$ is —OH, —OR$^9$ or —NR$^{10}$R$^{11}$;
each of R$^{8B}$, R$^{8C}$ and R$^{8D}$ is independently H, C$_{1-6}$ haloalkyl, or unsubstituted or substituted C$_{1-6}$ alkyl;
$R^9$ is unsubstituted or substituted C$_{1-6}$ alkyl, or a hydroxy protecting group;
each of $R^{10}$ and $R^{11}$ is independently H, unsubstituted or substituted C$_{1-6}$ alkyl, or an amino protecting group;
each of L$^{1a}$ and L$^{1b}$ is independently optionally substituted C$_{1-10}$ alkylene, optionally substituted C$_2$-C$_{10}$ alkenylene, or optionally substituted 2 to 15 membered heteroalkylene, where one or more carbon atoms are replaced with C(=O), O, S or N;
each L$^2$ is independently optionally substituted C$_{1-10}$ alkylene, optionally substituted C$_2$-C$_{10}$ alkenylene, or optionally substituted 2 to 15 membered heteroalkylene wherein one or more carbon atoms are replaced with C(=O), O, S or N; or C$_1$-C$_{10}$ alkylene or 2 to 15 membered heteroalkylene each independently interrupted by a ring or ring system selected from the group consisting of optionally substituted C$_6$-C$_{10}$ arylene, optionally substituted C$_3$-C$_{10}$ cycloalkylene, optionally substituted five to ten membered heteroarylene, and optionally substituted three to ten membered heterocyclylene;
L$^3$ is an optionally substituted C$_{1-10}$ membered alkylene, optionally substituted C$_2$-C$_{10}$ alkenylene, or optionally substituted 2 to 15 membered heteroalkylene where one or more carbon atoms are replaced with C(=O), O, S or N;
each Z is a triazole ring, or a bi-, tri-, or tetracyclic ring system having a fused triazole ring;
$B^1$ is H, hydroxy, a protected hydroxy, a natural nucleobase, a modified natural nucleobase, or an unnatural nucleobase;
G is

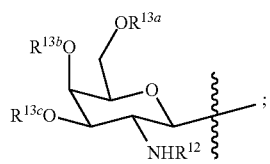

$R^{12}$ is —C(=O)C$_{1-6}$ alkyl, —C(=O)C$_{1-6}$ haloalkyl, or —C(=O)phenyl; and
each of R$^{13a}$, R$^{13b}$ and R$^{13c}$ is independently hydrogen, benzyl (Bn), or —C(=O)R$^{13A}$, wherein R$^{13A}$ is C$_{1-6}$ alkyl, C$_{1-6}$ haloalkyl, or optionally substituted phenyl;
provided that the compound has at least three G groups. In some further embodiments, the compound has three G groups.

In some embodiments of Formula (II), $R^1$ is -L$^{1b}$-C(=O)NR$^5$R$^6$, and each of $R^2$, $R^3$ and $R^4$ is -L$^{1a}$-Z-L$^2$-G. In other embodiments, $R^2$ is -L$^{1b}$-C(=O)NR$^5$R$^6$, and each of $R^1$, $R^3$ and $R^4$ is -L$^{1a}$-Z-L$^2$-G. In yet other embodiments, $R^3$ is -L$^{1b}$-C(=O)NR$^5$R$^6$, and each of $R^1$, $R^2$ and $R^4$ is -L$^{1a}$-Z-L$^2$-G. In still yet other embodiments, $R^4$ is -L$^{1b}$-C(=O)NR$^5$R$^6$, and each of $R^1$, $R^2$ and $R^3$ is -L$^{1a}$-Z-L$^2$-G.

In some embodiments of the compound of Formula (II), each Z is independently

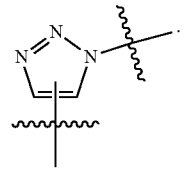

In some such embodiments, each Z is independently

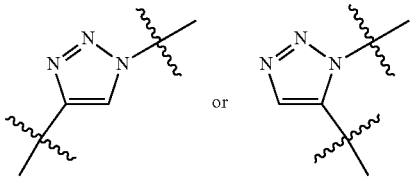 [SMILES: *c1cn(*)nn1 ; *c1cnnn1*]

In other embodiments, each Z is independently

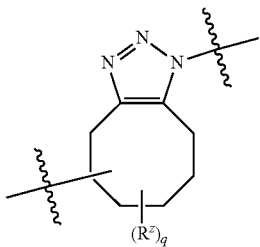

q is an integer from 0 to 6; each $R^z$ is independently halo or $C_{1-6}$ haloalkyl, or any two adjacent $R^z$ taken together with the atoms to which they are attached form an optionally substituted $C_{6-10}$ aryl, optionally substituted 5-10 membered heteroaryl, optionally substituted $C_{3-7}$ cycloalkyl, or optionally substituted 3 to 10 membered heterocyclyl. Alternatively, the cyclooctene ring fused to the triazole ring may contain one or more heteroatoms, for example, O, N or S. In some such embodiments, q is 1 or 2; and each $R^z$ is halo. In another such embodiment, each Z is independently

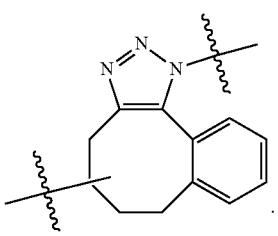

In yet another embodiment, each Z is independently

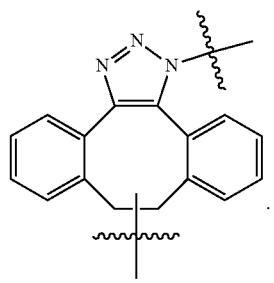

In yet another embodiment, each Z is

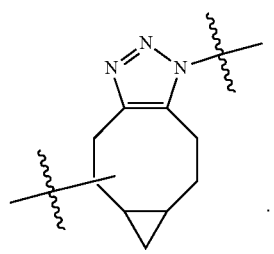

In some embodiments, the compound of Formula (II) has the Formula (IIa):

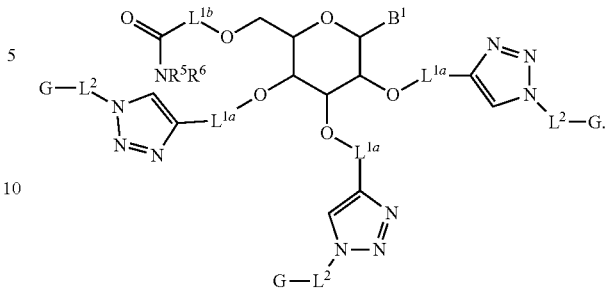

In some embodiments of Formula (II) or (IIa), each $L^{1a}$ and $L^{1b}$ is independently $C_{1-10}$ alkylene. In some such embodiments, each $L^{1a}$ and $L^{1b}$ is —$CH_2$—, —$(CH_2)_2$—, —$(CH_2)_3$—, or —$(CH_2)_4$—. In other embodiments, each $L^{1a}$ is independently 2 to 10 membered heteroalkylene, where one or more carbon atoms are replaced with C(=O), O, S or N. In some such embodiments, $L^{1a}$ is —$CH_2$—C(=O)NH—$CH_2$—.

In some embodiments of Formula (II) or (IIa), each of $L^2$ is independently 2 to 15 membered heteroalkylene, for example heteroalkylene containing one, two, three, four, or five heteroatoms selected from O, S, N, C(=O) or C(=S). In some such embodiments, each of $L^2$ is independently —$(CH_2CH_2O)_j$—, wherein j is 2, 3, 4, or 5.

In some embodiments of Formula (II) or (IIa), each of $R^{13a}$, $R^{13b}$, and $R^{13c}$ is —C(=O)$CH_3$. In some embodiments of Formula (II) or (IIa), $R^{12}$ is —C(=O)$CH_3$. In other embodiments, $R^{12}$ is —C(=O)$CF_3$. In some embodiments of Formula (II) or (IIa), each of $R^{13a}$, $R^{13b}$, and $R^{13c}$ is —C(=O)$CH_3$, and $R^{12}$ is —C(=O)$CH_3$.

In some embodiments of Formula (II) or (IIa), $L^3$ is a $C_{1-10}$ membered alkylene. In some such embodiments, $L^3$ is —$CH_2$—, —$(CH_2)_2$—, —$(CH_2)_3$—, or —$(CH_2)_4$—. In some embodiments, m is 0. In other embodiments, m is 1. In some embodiments, m is 2. In some embodiments, m is 3. In some embodiments of Formula (II) or (IIa), n is 0. In other embodiments, n is 1. In some embodiments, n is 2. In some embodiments, n is 3. In some embodiments of Formula (II) or (IIa), m is 0 and n is 1. In other embodiments, m is 1 and n is 0. In yet other embodiments, both m and n are 0. In still yet other embodiments, both m and n are 1.

In some embodiments of Formula (II) or (IIa), $R^7$ is a trityl type of hydroxy protecting group selected from (4-methoxyphenyl)diphenylmethyl, bis(4-methoxyphenyl)phenylmethyl (DMTr), tris(4-methoxyphenyl)methyl, 9-phenylxanthen-9-yl, or 9-(4-methoxyphenyl)xanthen-9-yl. In some specific embodiments, $R^7$ is bis(4-methoxyphenyl)phenylmethyl (DMTr).

In some embodiments of Formula (II) or (IIa), $R^8$ is —C(=O)$CH_2CH_2$C(=O)OH. In another embodiments, $R^8$ is —C(=O)$CH_2CH_2$C(=O)$NH_2$. In other embodiments, $R^8$ is or —P(O$R^{8B}$)N$R^{8C}R^{8D}$ wherein $R^{8B}$ is H or substituted $C_{1-6}$ alkyl, and each $R^{8C}$ and $R^{8D}$ is independently unsubstituted or substituted $C_{1-6}$ alkyl. In one embodiment, $R^8$ is

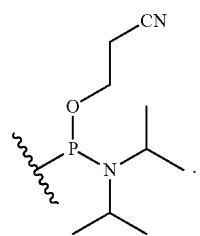

In yet another embodiment, R⁸ is H.

In some embodiments of Formula (II) or (IIa), B¹ is

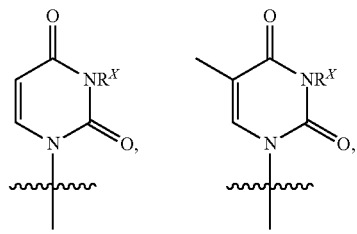

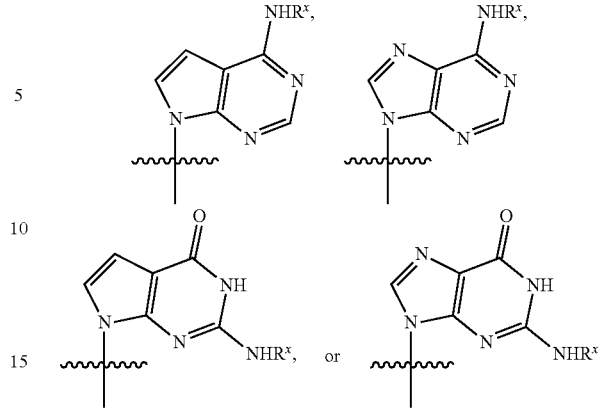

wherein $R^x$ is hydrogen or an amino protecting group, or the hydrogen in —NHR$^x$ is absent and R$^x$ is a divalent amino protecting group. In some such embodiments, R$^x$ is H. In some such embodiments, R$^x$ is —C(=O)C$_{1-6}$ alkyl, —CH$_2$-phenyl, or —C(=O)phenyl, or the hydrogen in —NHR$^x$ is absent, and R$^x$ is

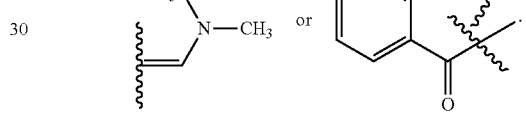

In another embodiment, B¹ is H. In yet another embodiment, B¹ is hydroxy or a protected hydroxy group (e.g., —OAc).

In some embodiments, the compound of Formula (II) is a compound having the structure:

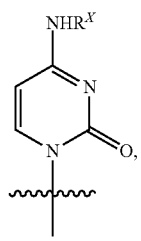

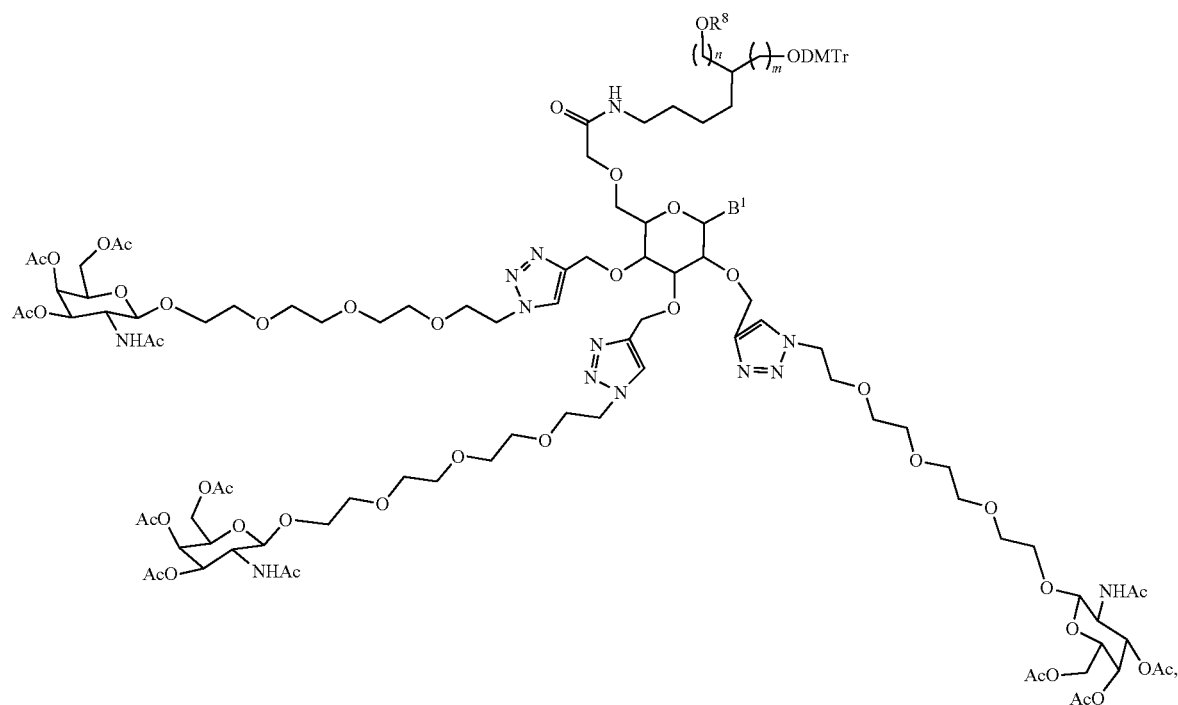

-continued
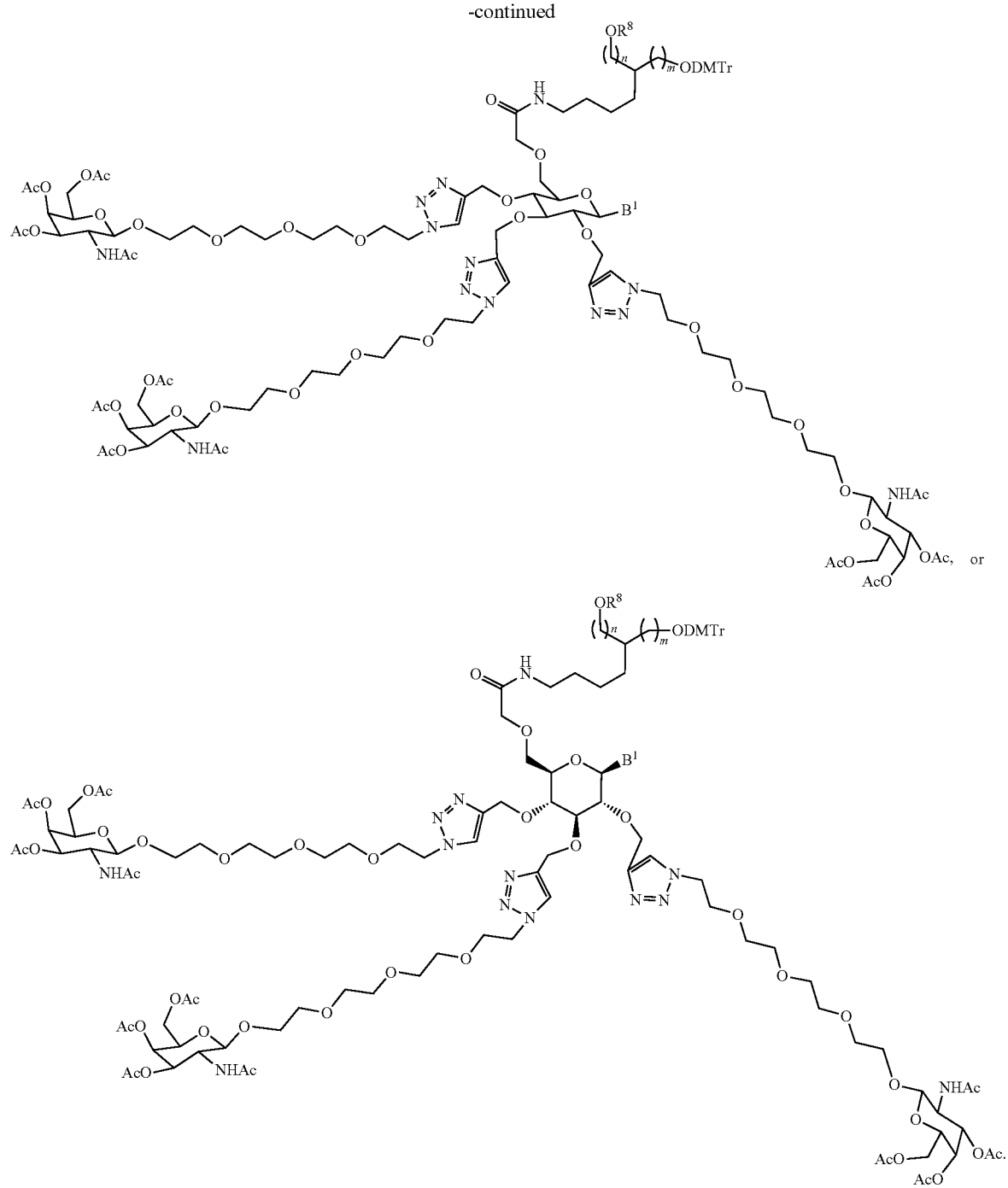
In some such embodiments, $B^1$ is
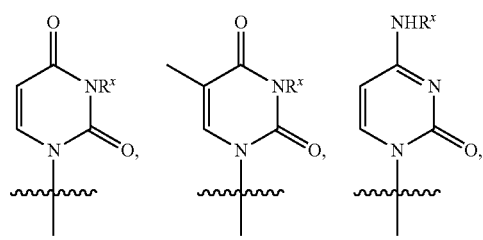

-continued

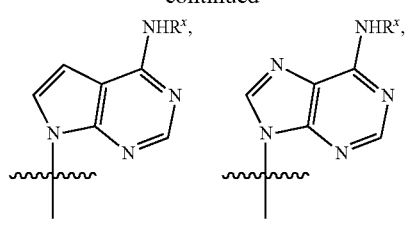

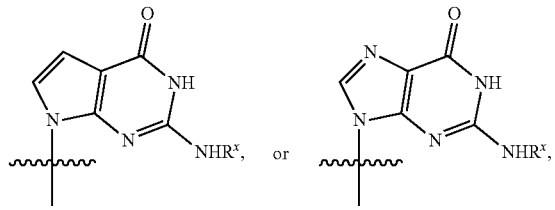

wherein $R^x$ is hydrogen or an amino protecting group, or the hydrogen in —$NHR^x$ is absent and $R^x$ is a divalent amino protecting group. In some such embodiments, $R^x$ in

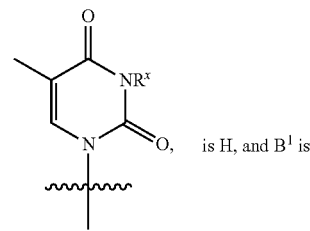

is H, and $B^1$ is

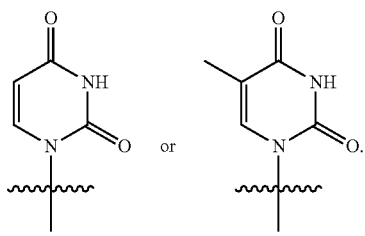

In other embodiments, $B^1$ is H or a protected hydroxy group. In one embodiment, m is 1 and n is 1. In another embodiment, m is 1 and n is 0. In another embodiment, m is 0 and n is 1. In some further embodiments, the compound has a structure selected from:

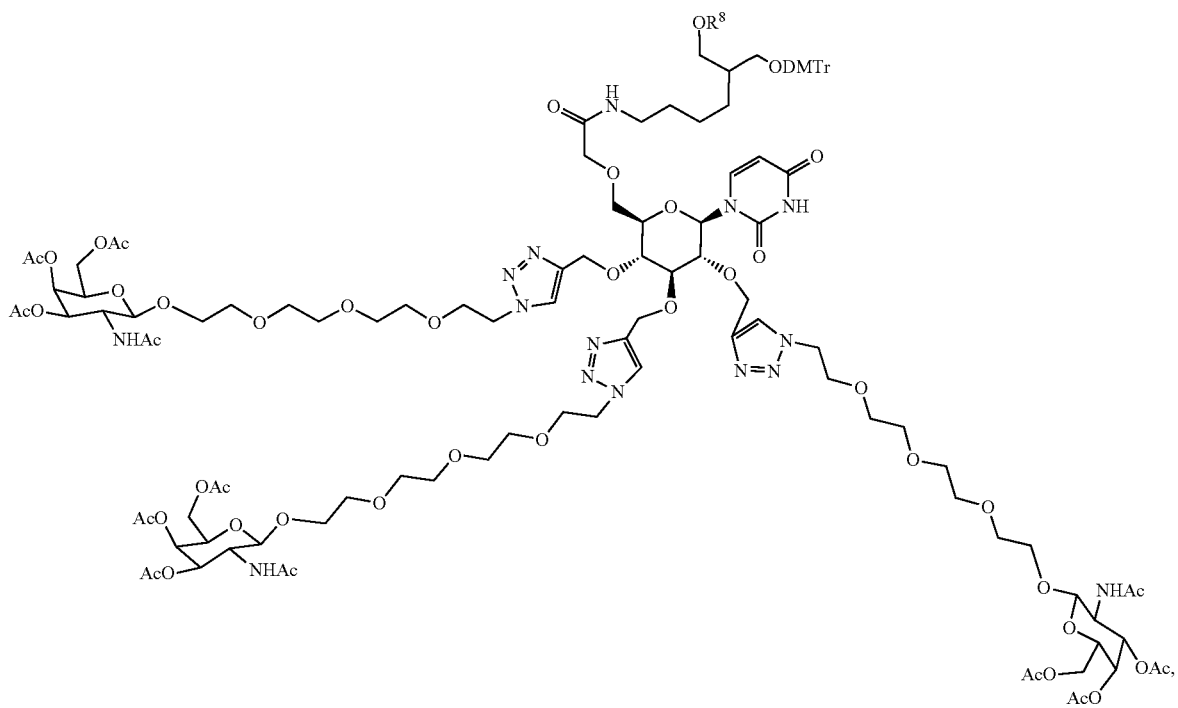

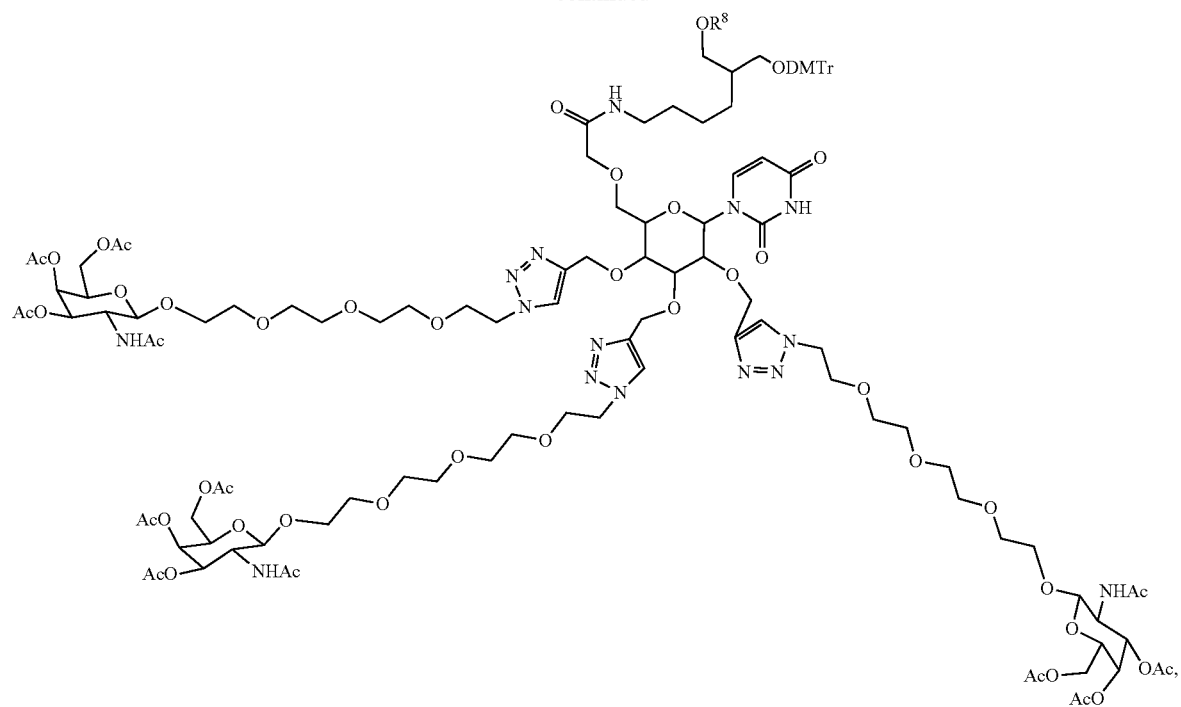
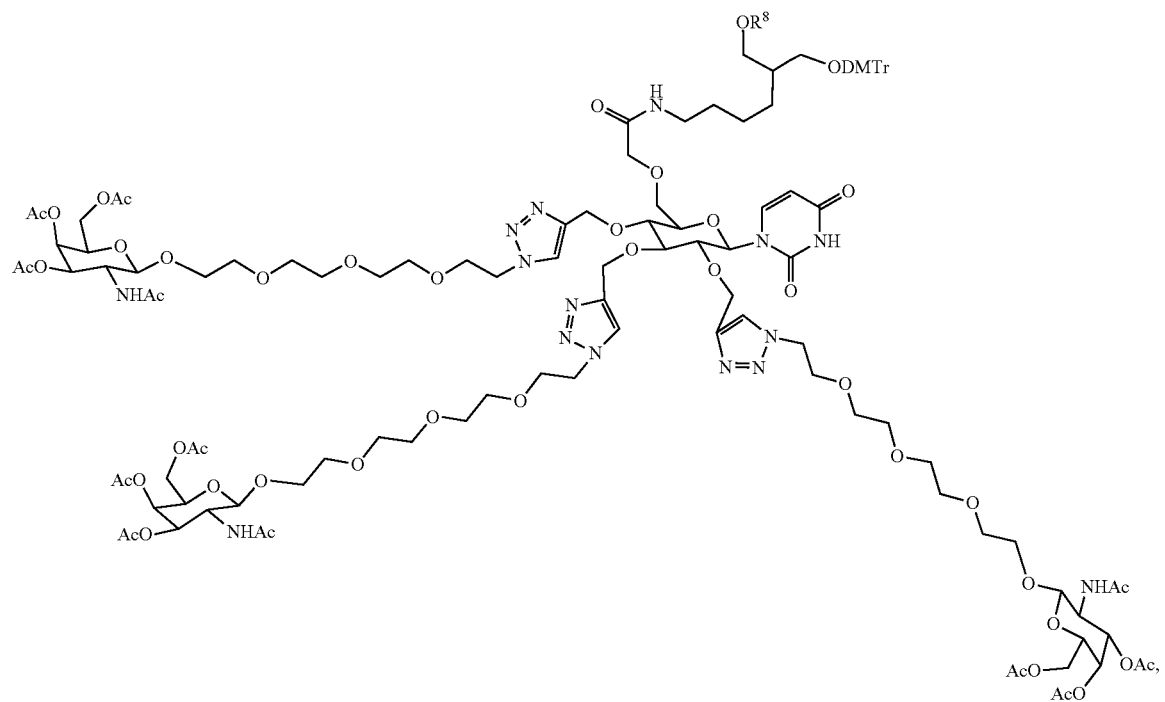

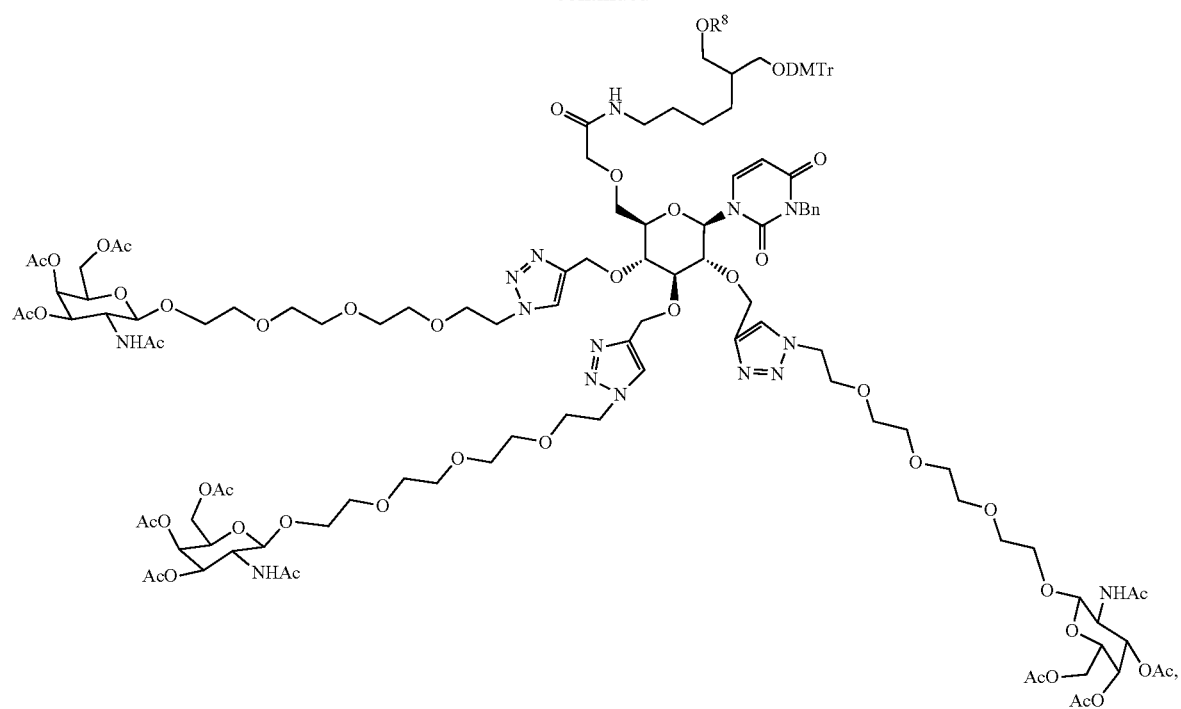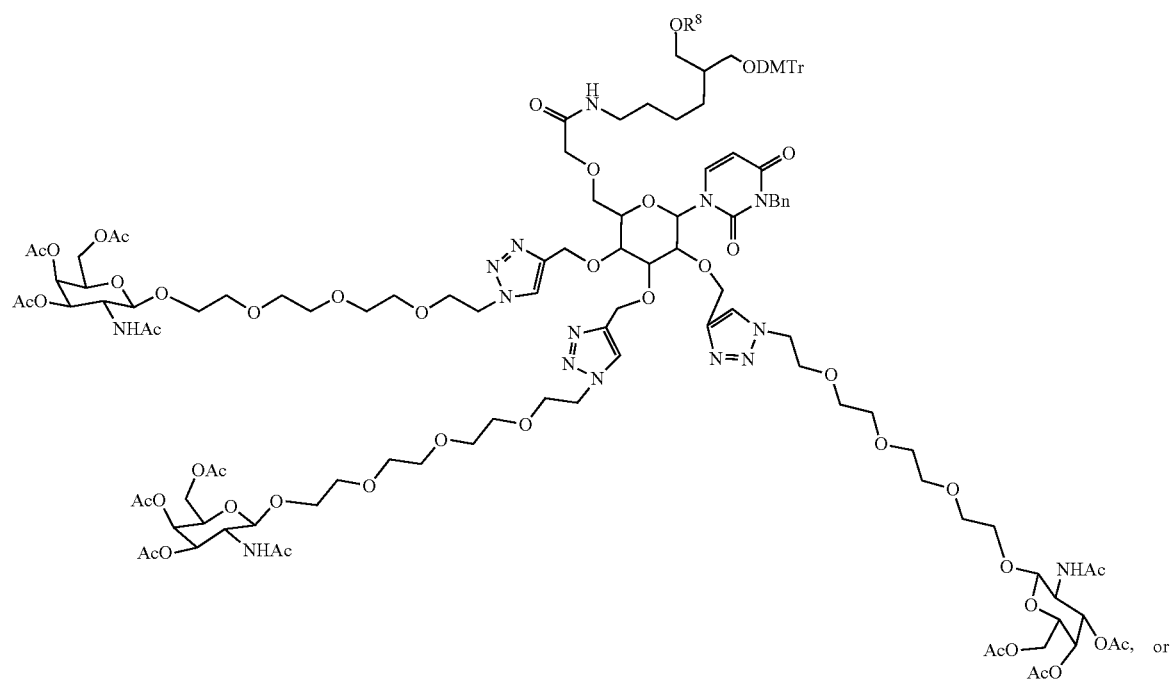

-continued

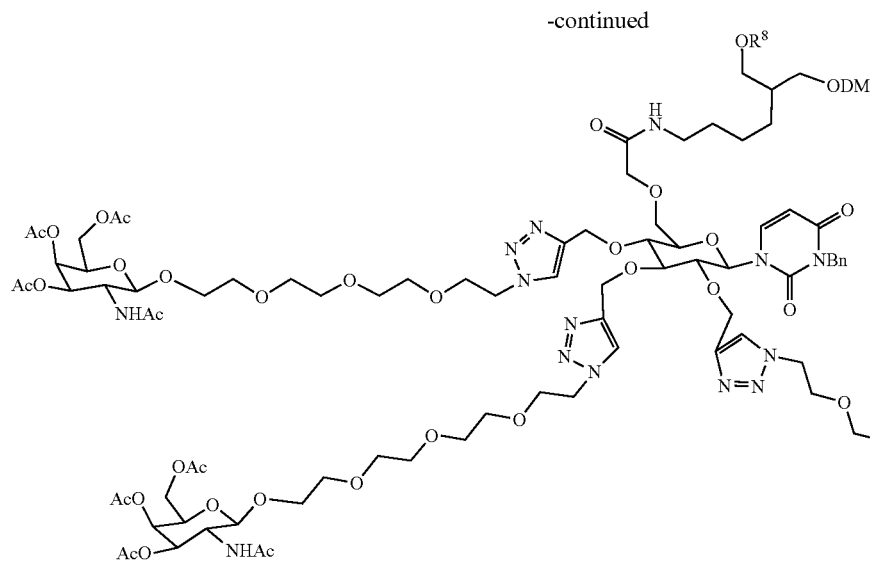

In some such embodiments, $R^8$ is —C(=O)CH$_2$CH$_2$C(=O)OH. In other such embodiments, $R^8$ is —C(=O)CH$_2$CH$_2$C(=O)NH$_2$. In other embodiments, $R^8$ is or —P(OR$^{8B}$)NR$^{8C}$R$^{8D}$, wherein $R^{8B}$ is H or substituted $C_{1-6}$ alkyl, and each $R^{8C}$ and $R^{8D}$ is independently unsubstituted or substituted $C_{1-6}$ alkyl. In one such embodiment, $R^8$ is

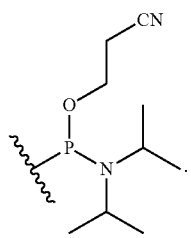 [SMILES: *P(OCCC#N)N(C(C)C)C(C)C]

In any embodiments of the compounds of Formula (I), (Ia), (Ia'), (Ib), (Ib'), (Ic), (Ic'), (II), or (IIa) described herein, when $R^8$ comprises a succinate moiety (—C(O)CH$_2$CH$_2$C(O)OH) or a succinimide moiety (—C(O)CH$_2$CH$_2$C(O)NH$_2$), the compound may be attached to a solid support through the succinate moiety, optionally via a linker.

In any embodiments of the compounds of Formula (I), (Ia), (Ia'), (Ib), (Ib'), (Ic), (Ic'), (II), or (IIa) described herein, when $R^8$ comprises a phosphoramidite moiety such as

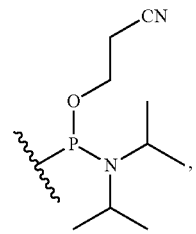 [SMILES: *P(OCCC#N)N(C(C)C)C(C)C]

the compound may be used to react with 5'-OH of another nucleoside or the 5'-OH terminal of an oligonucleotide.

Solid Support Conjugated with GalNAc Compounds

Some embodiments of the present application relate to a solid support comprising the compound of Formula (I) (including (Ia), (Ia'), (Ib), (Ib'), (Ic), and (Ic')), or Formula (II) (including (IIa)) as described herein covalently attached thereto, for example, via $R^8$ of the compound. In one embodiment, $R^8$ is —C(=O)CH$_2$CH$_2$C(=O)OH. In another embodiment, $R^8$ is —C(=O)CH$_2$CH$_2$C(=O)NH$_2$. In further embodiments, the compound is covalently attached to the solid support via a moiety

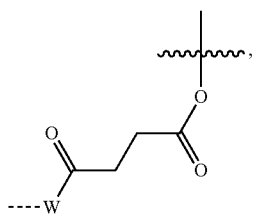

wherein W is O or NH; wherein the dashed line refers to the connection with the solid support, optionally through an additional linker, and the squiggly line refers to the point of the attachment of the oxygen atom (that is covalently attached to $R^8$ of the compound) to the remaining portion of the compound. In further embodiments, the solid support bounded nucleoside may serve as a starting point for solid phase oligo synthesis, through —$OR^7$ functionality of the compound after deprotection to expose the free hydroxy group. In non-limiting embodiments, the solid support may comprise controlled pore glass (CPG) or macroporous polystyrene (MPPS), or $SiO_2$ particles.

Functionalized GalNAc Analogs in Oligonucleotide Synthesis

Some embodiments of the present application relate to a method for preparing a synthetic oligonucleotide, comprising reacting a compound described herein, with an oligonucleotide. In some embodiments, the oligonucleotide comprises 1 to 100 base length, 5 to 50 base length, or 10 to 30 base length. In further embodiments, the reaction is conducted on a solid support.

Step 1: De-Blocking (Detritylation)

The DMTr group is removed with a solution of an acid, such as 2% trichloroacetic acid (TCA) or 3% dichloroacetic acid (DCA), in an inert solvent (dichloromethane or toluene). The orange-colored DMTr cation formed is washed out; the step results in the solid support-bound oligonucleotide precursor bearing a free 5'-terminal hydroxyl group.

Step 2: Coupling

A 0.02-0.2M solution of nucleoside phosphoramidite (or a mixture of several phosphoramidites) in acetonitrile is activated by a 0.2-0.7 M solution of an acidic azole catalyst, 1H-tetrazole, 5-ethylthio-1H-tetrazole, 2-benzylthiotetrazole, 4,5-dicyanoimidazole, or a number of similar compounds. The mixing is usually very brief and occurs in fluid lines of oligonucleotide synthesizers (see below) while the components are being delivered to the reactors containing solid support. The activated phosphoramidite in 1.5-20-fold excess over the support-bound material is then brought in contact with the starting solid support (first coupling) or a support-bound oligonucleotide precursor (following couplings) whose 5'-hydroxy group reacts with the activated phosphoramidite moiety of the incoming nucleoside phosphoramidite to form a phosphite triester linkage. The reaction is also highly sensitive to the presence of water, particularly when dilute solutions of phosphoramidites are used, and is commonly carried out in anhydrous acetonitrile. Upon the completion of the coupling, any unbound reagents and by-products are removed by washing.

Step 3: Capping

The capping step is performed by treating the solid support-bound material with a mixture of acetic anhydride and 1-methylimidazole or, less often, DMAP as catalysts and, in the phosphoramidite method, serves two purposes. After the completion of the coupling reaction, a small percentage of the solid support-bound 5'-OH groups (0.1 to 1%) remains unreacted and needs to be permanently blocked from further chain elongation to prevent the formation of oligonucleotides with an internal base deletion commonly referred to as (n–1) shortmers. The unreacted 5'-hydroxy groups are, to a large extent, acetylated by the capping mixture. It has also been reported that phosphoramidites activated with $^1$H-tetrazole react, to a small extent, with the $O^6$ position of guanosine. Upon oxidation with $I_2$/water, this side product, possibly via $O^6$—N7 migration, undergoes depurination. The apurinic sites thus formed are readily cleaved in the course of the final deprotection of the oligonucleotide under the basic conditions to give two shorter oligonucleotides thus reducing the yield of the full-length product. The $O^6$ modifications are rapidly removed by treatment with the capping reagent as long as the capping step is performed prior to oxidation with $I_2$/water.

Step 4: Oxidation

The newly formed tricoordinated phosphite triester linkage is not natural and is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or (1S)-(+)-(10-camphorsulfonyl)-oxaziridine (CSO). The step of oxidation may be substituted with a sulfurization step to obtain oligonucleotide phosphorothioates. In the latter case, the sulfurization step is best carried out prior to capping.

In solid-phase synthesis, an oligonucleotide being assembled is covalently bound, via its 3'-terminal hydroxy group, to a solid support material and remains attached to it over the entire course of the chain assembly. The solid support is contained in columns whose dimensions depend on the scale of synthesis and may vary between 0.05 mL and several liters. At the end of the chain assembly, the oligonucleotide is released from the solid support and is eluted from the column or the well. The two most often used solid-phase materials are controlled pore glass (CPG) and macroporous polystyrene (MPPS).

In contrast to organic solid-phase synthesis and peptide synthesis, the synthesis of oligonucleotides proceeds best on non-swellable or low-swellable solid supports. The two most often used solid-phase materials are controlled pore glass (CPG) and macroporous polystyrene (MPPS).

CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material is treated with (3-aminopropyl)triethoxysilane to give aminopropyl CPG. The aminopropyl arm may be further extended to result in long chain aminoalkyl (LCAA) CPG. The amino group is then used as an anchoring point for linkers suitable for oligonucleotide synthesis.

MPPS suitable for oligonucleotide synthesis is a low-swellable, highly cross-linked polystyrene obtained by polymerization of divinylbenzene, styrene, and 4-chloromethylstyrene in the presence of a porogeneous agent. The macroporous chloromethyl MPPS obtained is converted to aminomethyl MPPS.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. Preparation of GalNAc-Azide Unit for Click Chemistry

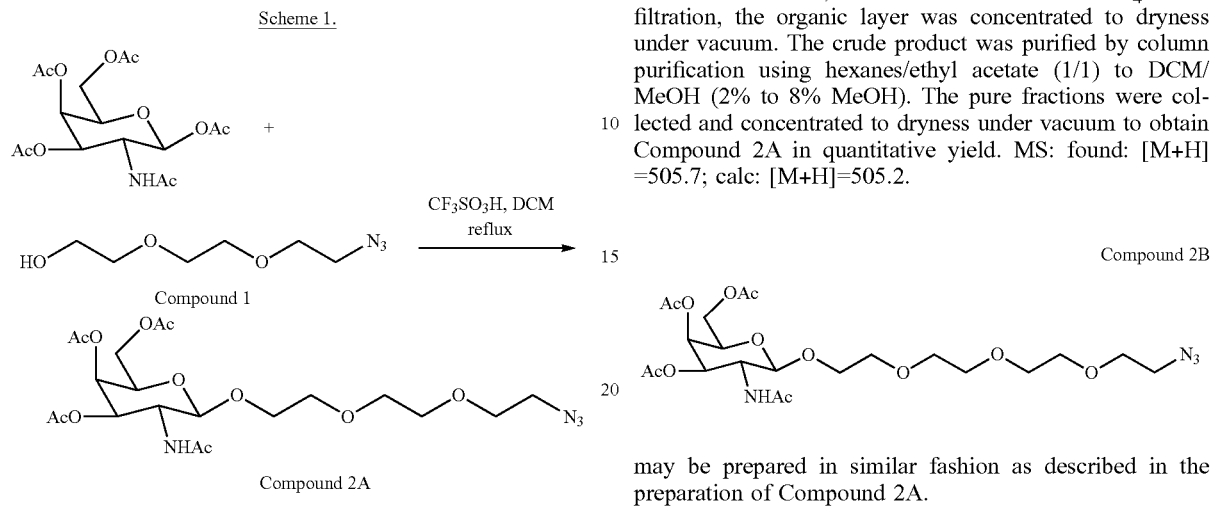

Scheme 1.

Compound 2: GalNAc (10 g, 25.7 mmol) and Compound 1 (15.4 g, 102.7 mmol) were dissolved in DCM (100 mL) and CF$_3$SO$_3$H (0.34 mL, 3.85 mmol) was then added. The reaction mixture was reflux under argon overnight and then cooled down to rt. This mixture was then poured into 1 M NaHCO$_3$ (51 mL), and the organic layer was separated, washed with water, brine and dried over Na$_2$SO$_4$. After filtration, the organic layer was concentrated to dryness under vacuum. The crude product was purified by column purification using hexanes/ethyl acetate (1/1) to DCM/MeOH (2% to 8% MeOH). The pure fractions were collected and concentrated to dryness under vacuum to obtain Compound 2A in quantitative yield. MS: found: [M+H]=505.7; calc: [M+H]=505.2.

Compound 2B may be prepared in similar fashion as described in the preparation of Compound 2A.

Example 2. General Procedure for the Preparation of Trivalent GalNAc Analog

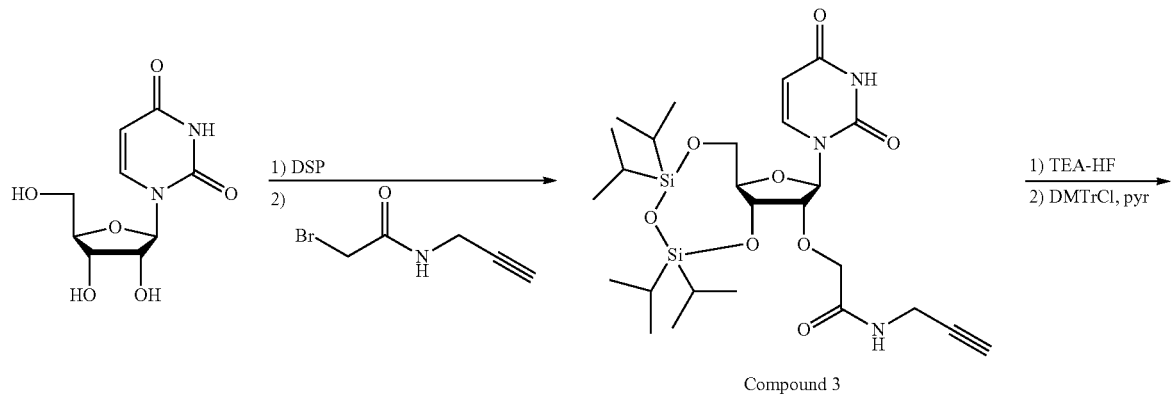

Scheme 2.

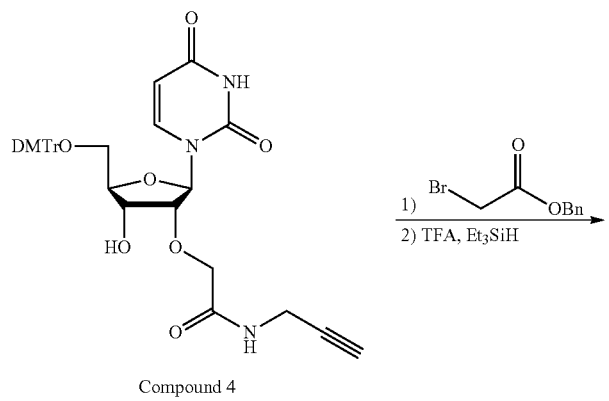

-continued
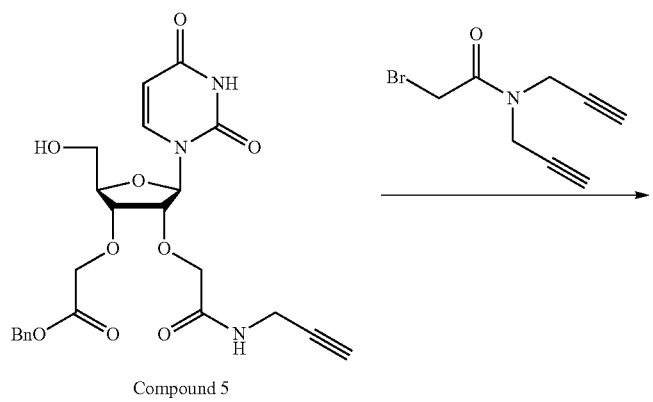
Compound 5
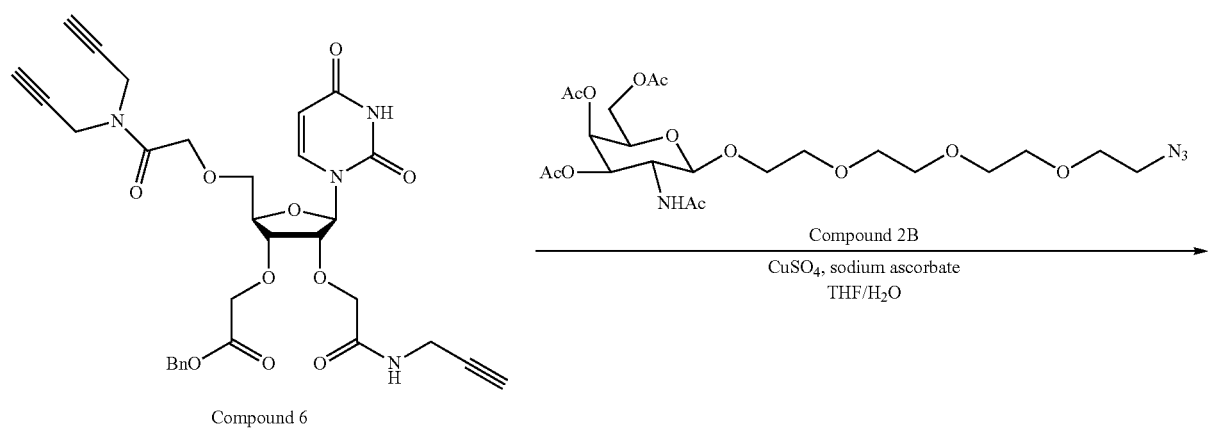
Compound 6
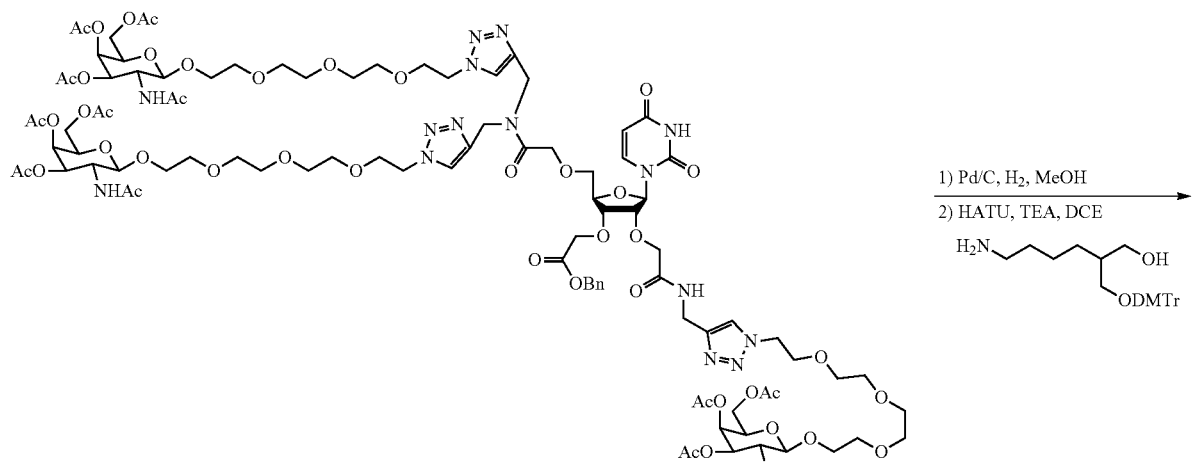
Compound 7

-continued
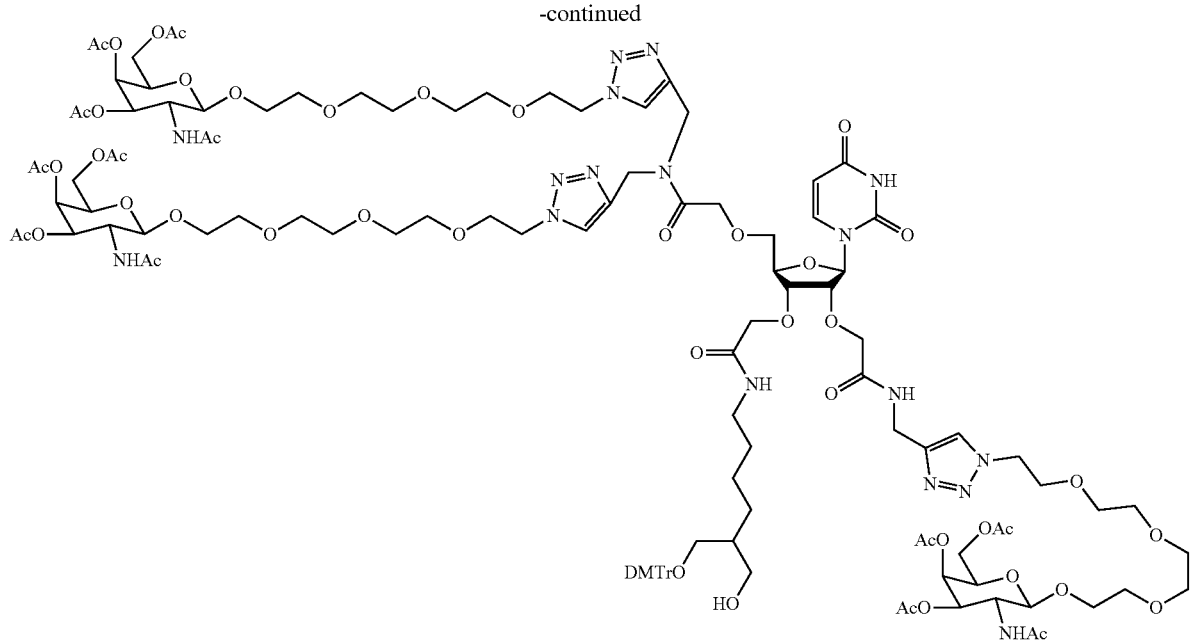
Compound 8
Trivalent GalNAc analog Compound 8 may be prepared according to Scheme 2 via click chemistry.
Example 3. General Procedure for the Preparation of Trivalent GalNAc Analog
Scheme 3.
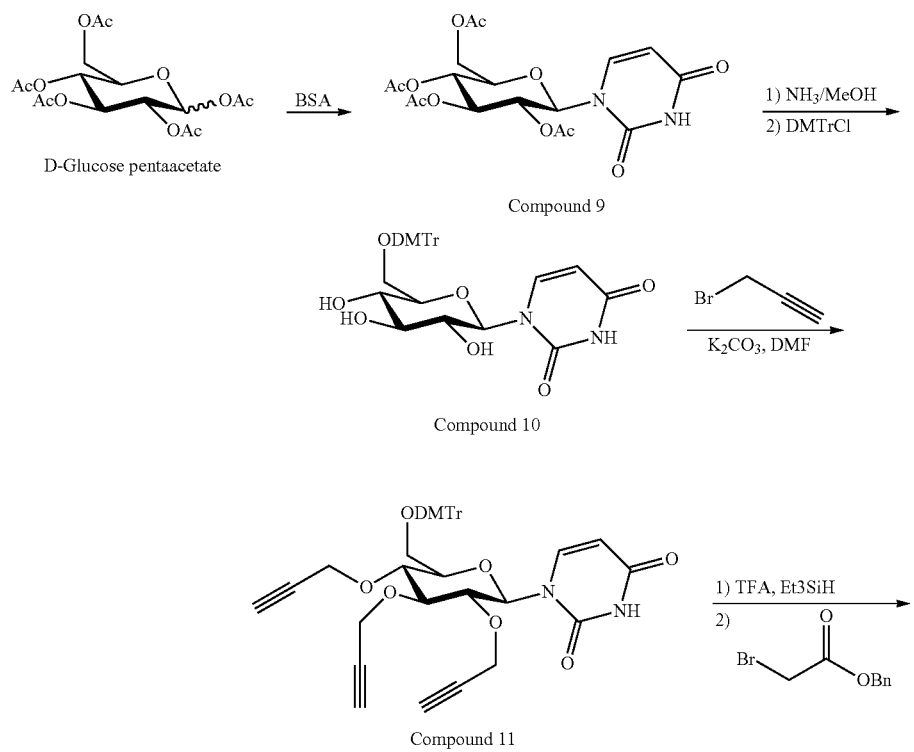

-continued
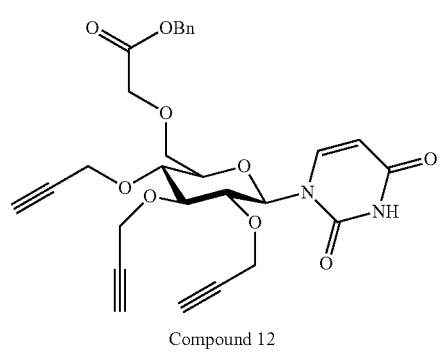
Compound 12
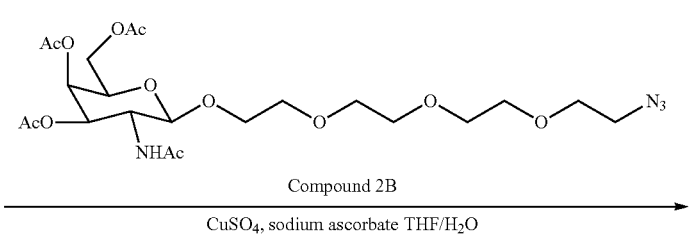
Compound 2B
CuSO₄, sodium ascorbate THF/H₂O →
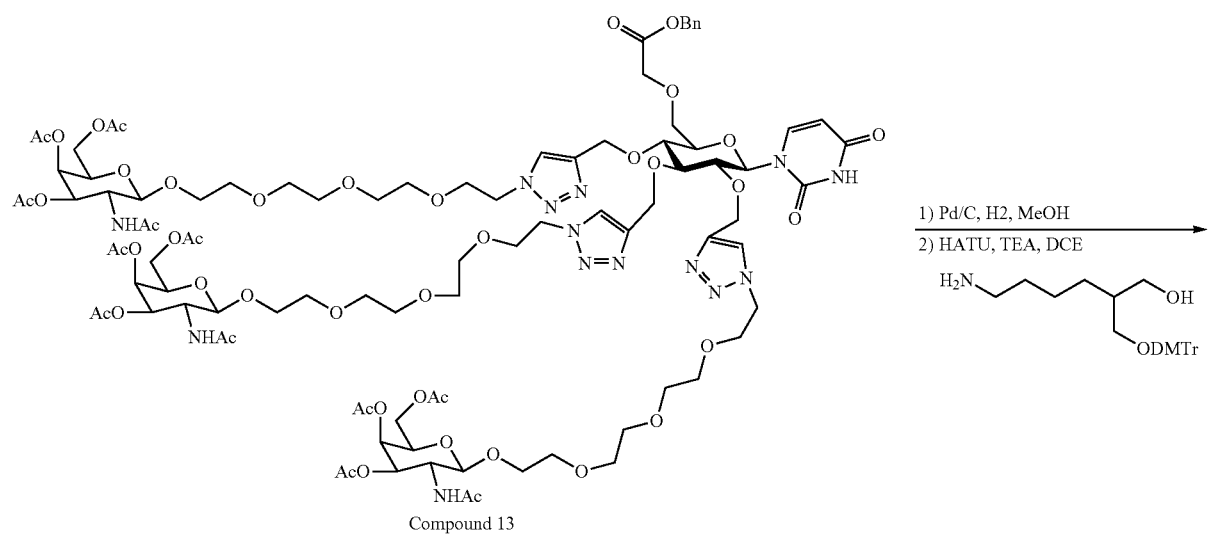
Compound 13
1) Pd/C, H2, MeOH
2) HATU, TEA, DCE
H₂N—⟨⟩—OH, ODMTr
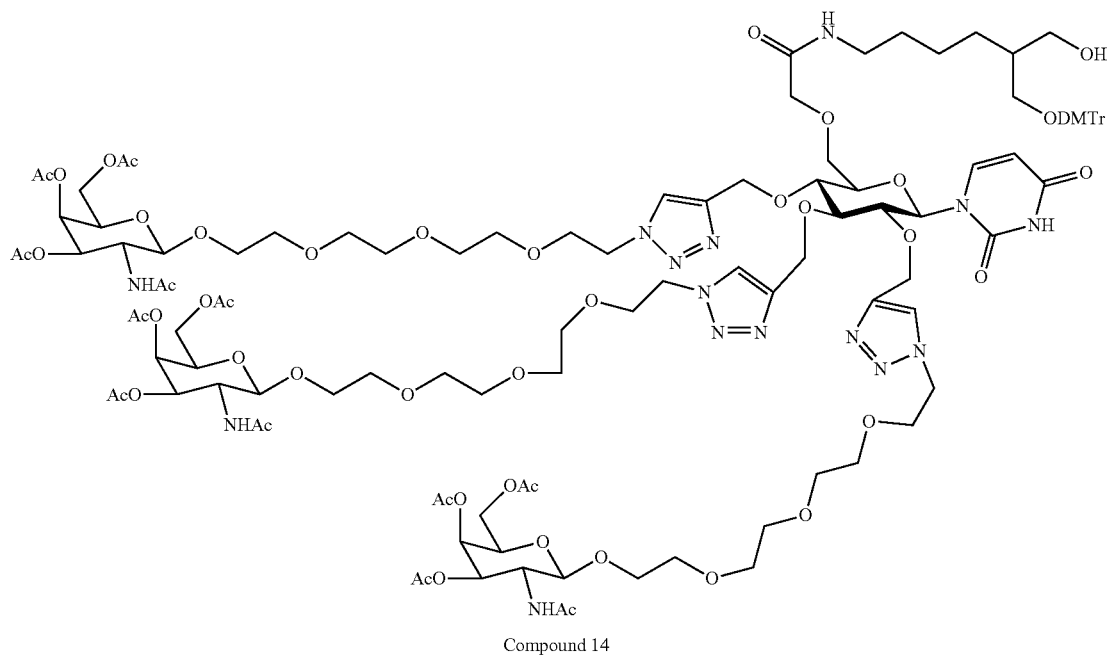
Compound 14

Trivalent GalNAc analog Compound 14 may be prepared according to Scheme 3 via click chemistry.
Example 4. General Procedure for the Preparation of Trivalent GalNAc Analog
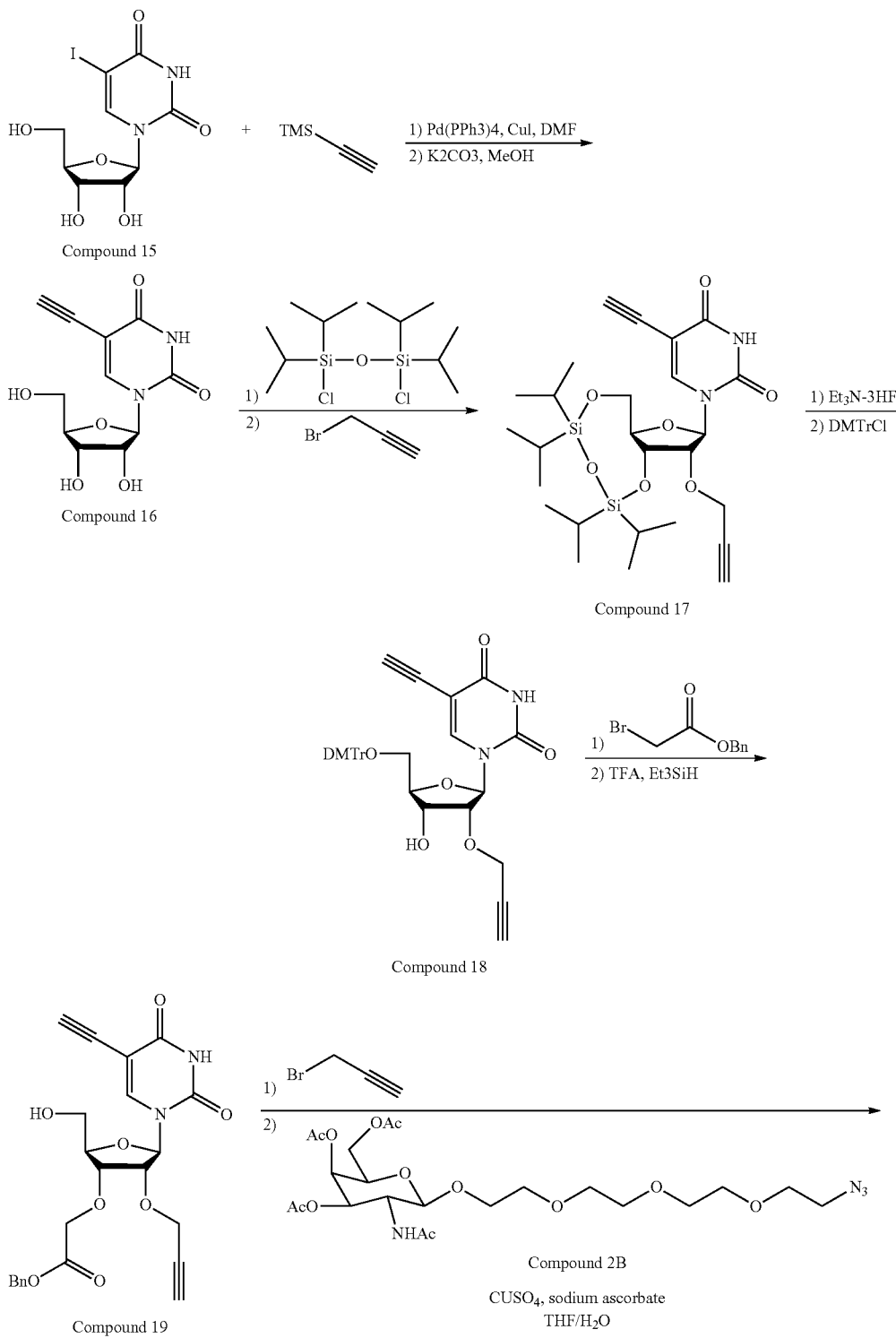
Scheme 4.

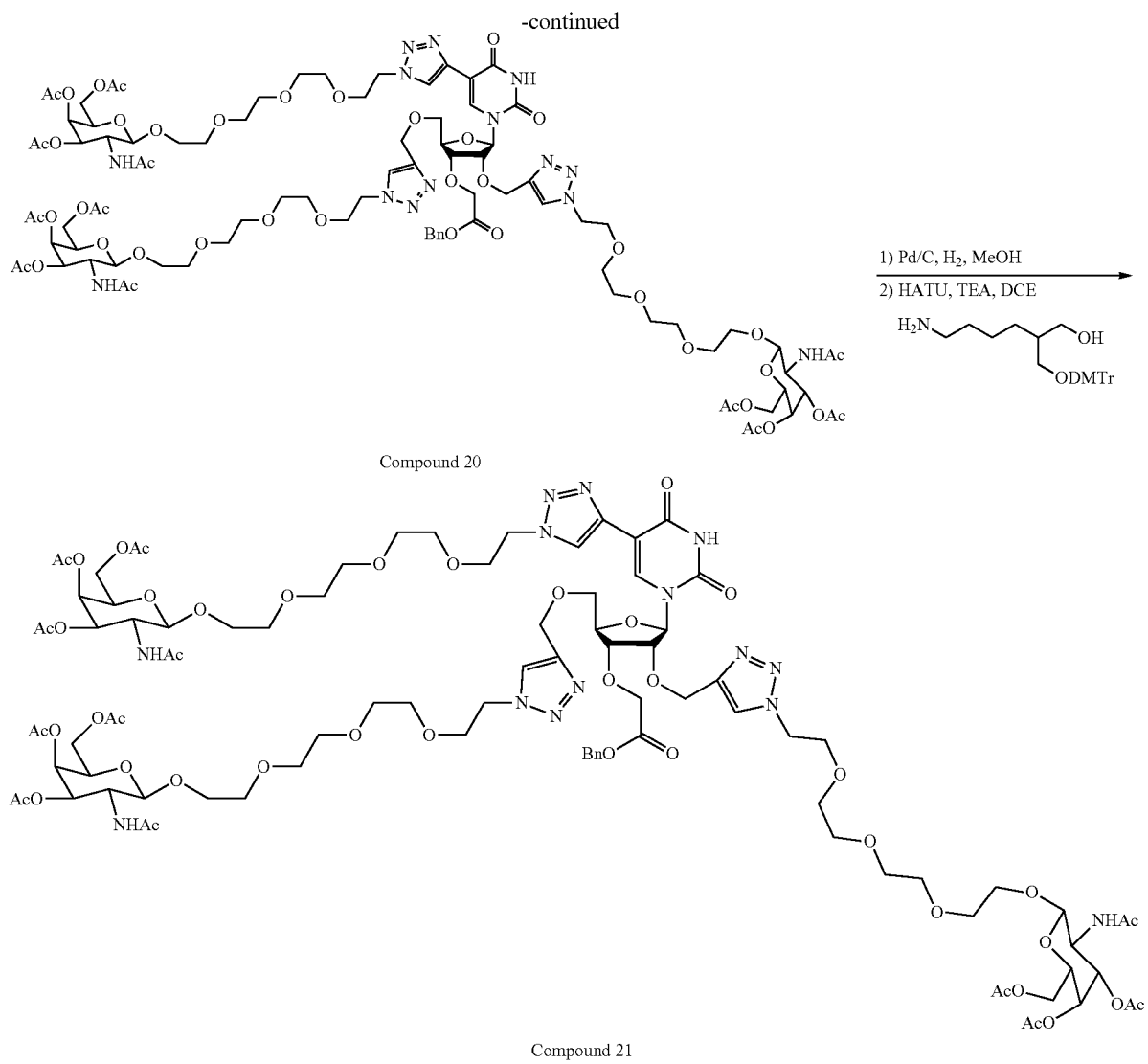
Compound 20
1) Pd/C, H₂, MeOH
2) HATU, TEA, DCE
Compound 21
Trivalent GalNAc analog Compound 21 may be prepared according to Scheme 4 via click chemistry.
Example 5. General Procedure for the Preparation of Trivalent GalNAc Analog
Scheme 5.
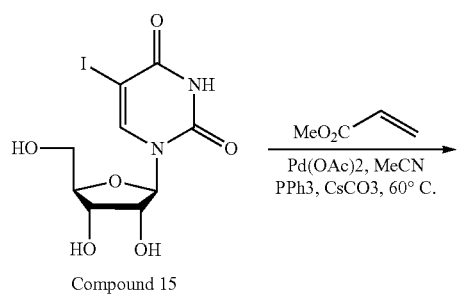
Compound 15

-continued
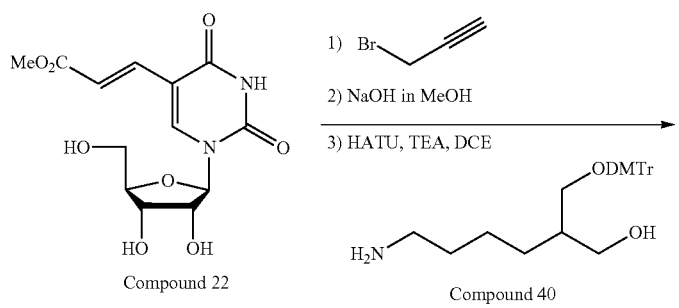
Compound 22
Compound 40
1) Br-CH2-C≡CH
2) NaOH in MeOH
3) HATU, TEA, DCE
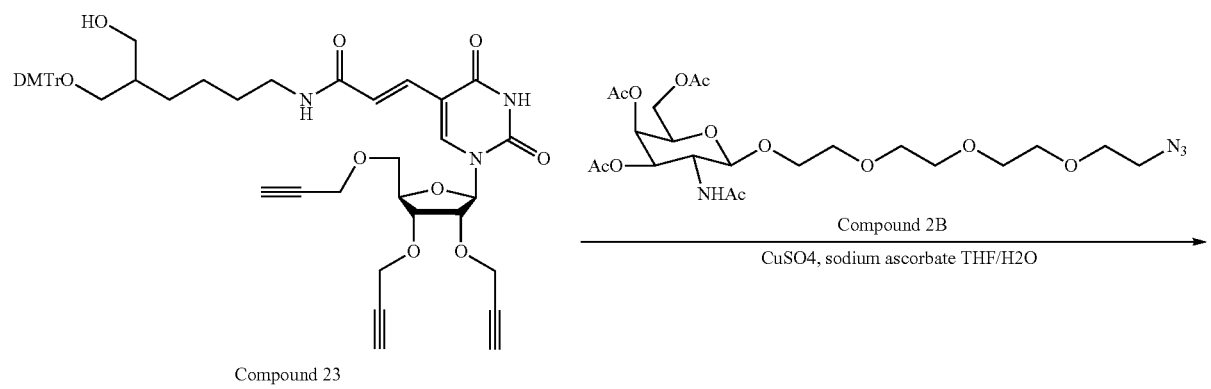
Compound 23
Compound 2B
CuSO4, sodium ascorbate THF/H2O
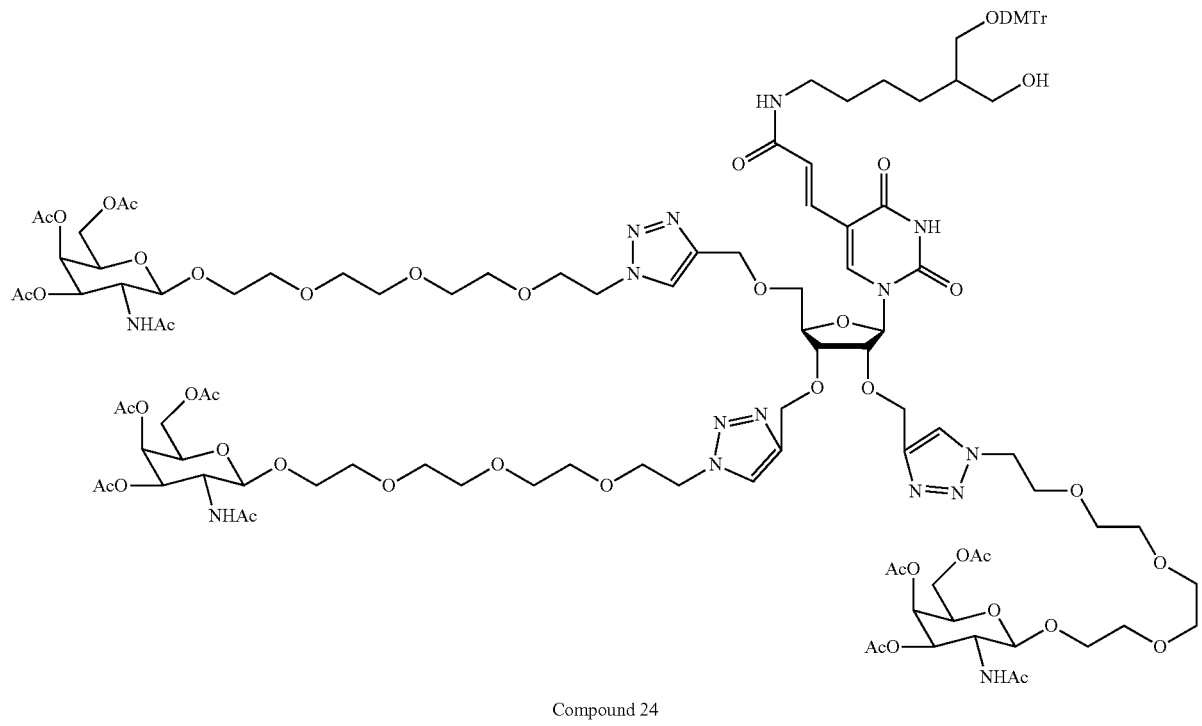
Compound 24

Trivalent GalNAc analog Compound 24 may be prepared according to Scheme 5 via click chemistry.
Example 6. Preparation of Trivalent GalNAc Analogs Compounds 25 and 27
Scheme 6A. Preparation of Compound 25
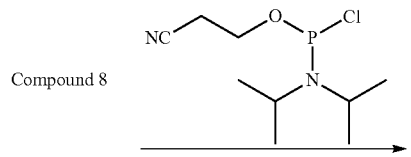
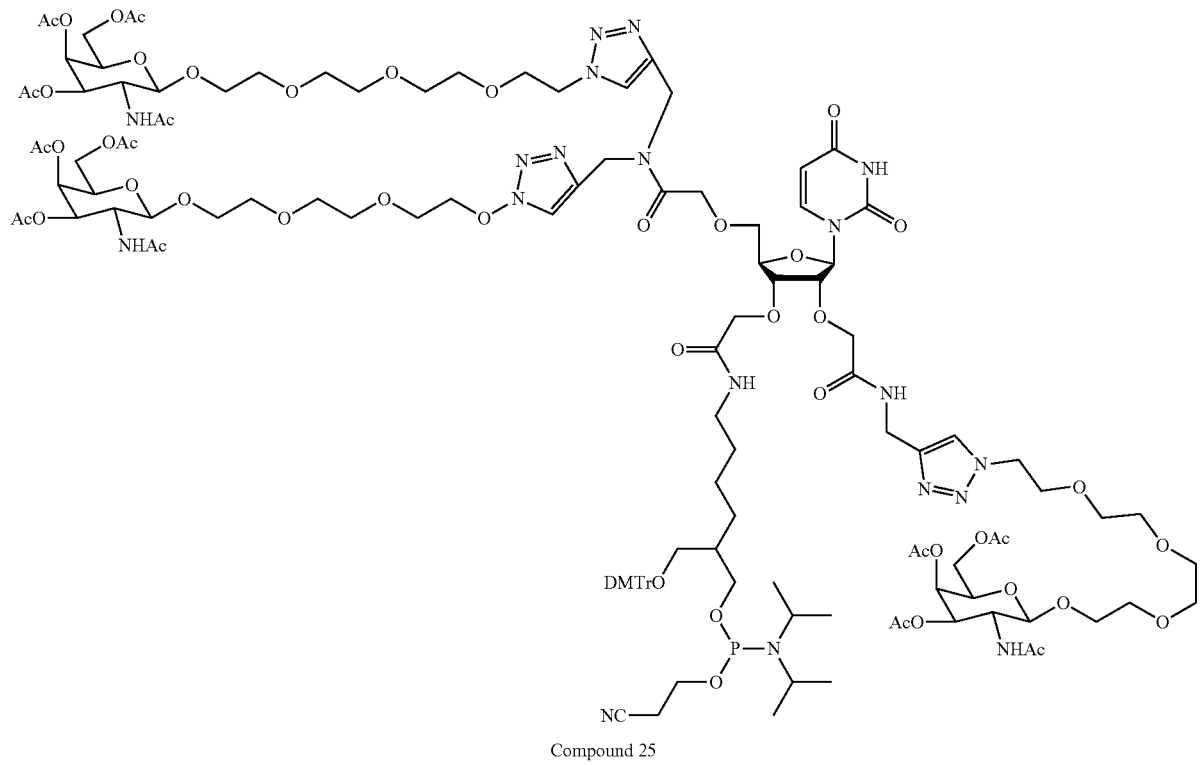
Compound 25
Compound 25 may be prepared from Compound 8 according to Scheme 6A.
Scheme 6B. Preparation of Compound 27 attached to a solid support
Compound 8
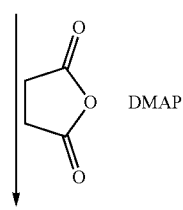

-continued
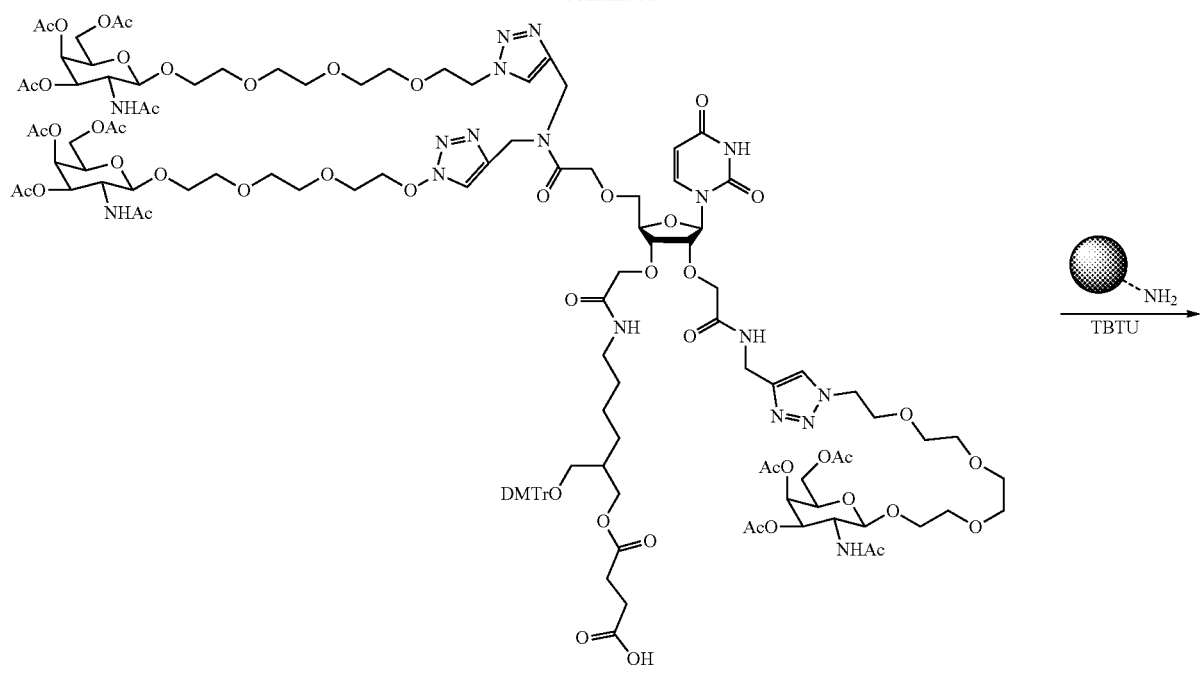
Compound 26
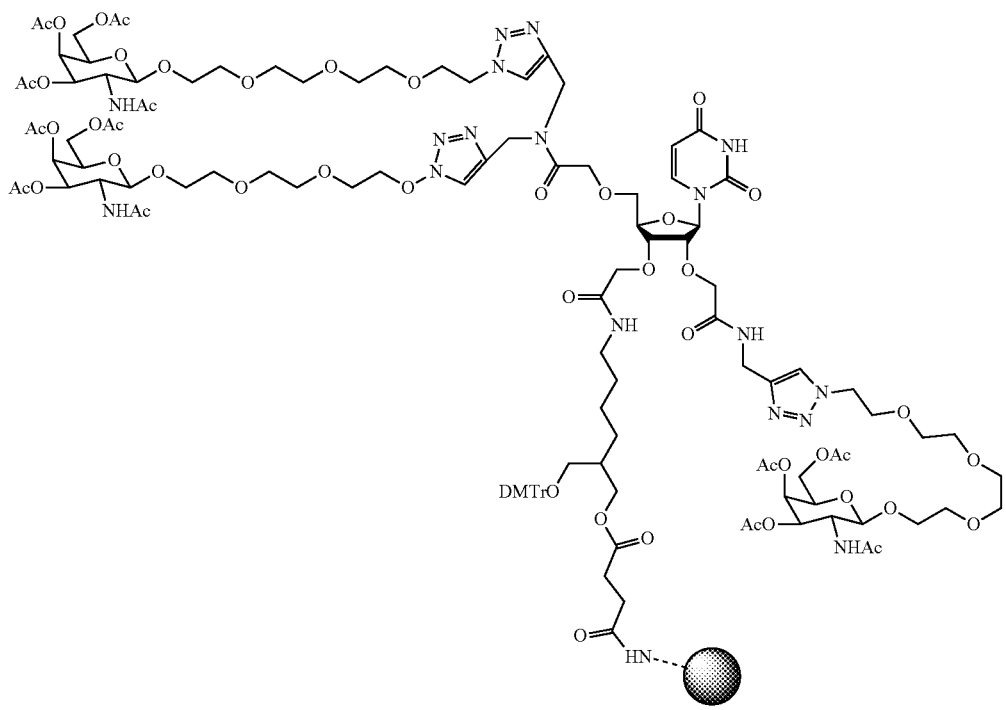
Compound 27

Compound 8 is first reacted with succinic anhydride to converted to the corresponding succinate analog Compound 26, then attached to a solid support with amino functionality to form solid support bound Compound 27.

Example 7. Preparation of Trivalent GalNAc Analogs Compounds 28 and 30

Scheme 7A. Preparation of Compound 28

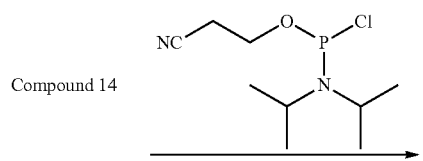

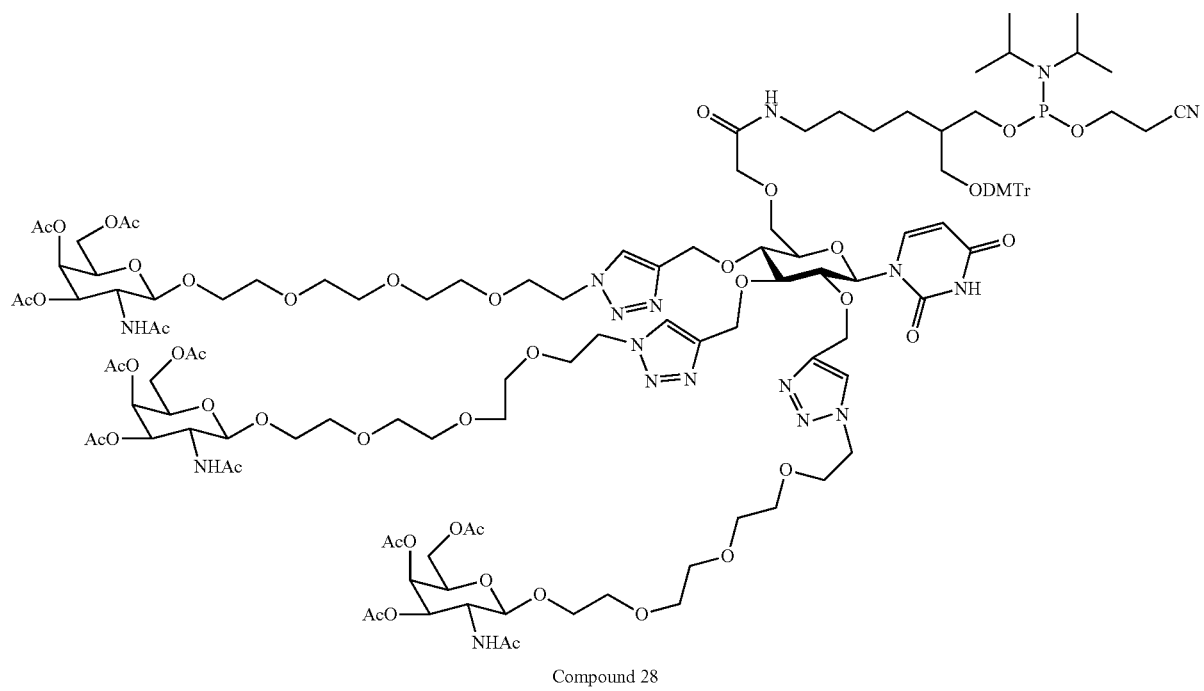

Compound 28

Compound 28 may be prepared from Compound 14 according to Scheme 7A.

Scheme 7B. Preparation of Compound 30 attached to a solid support

Compound 14

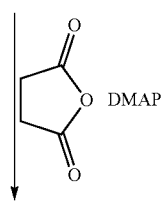

-continued
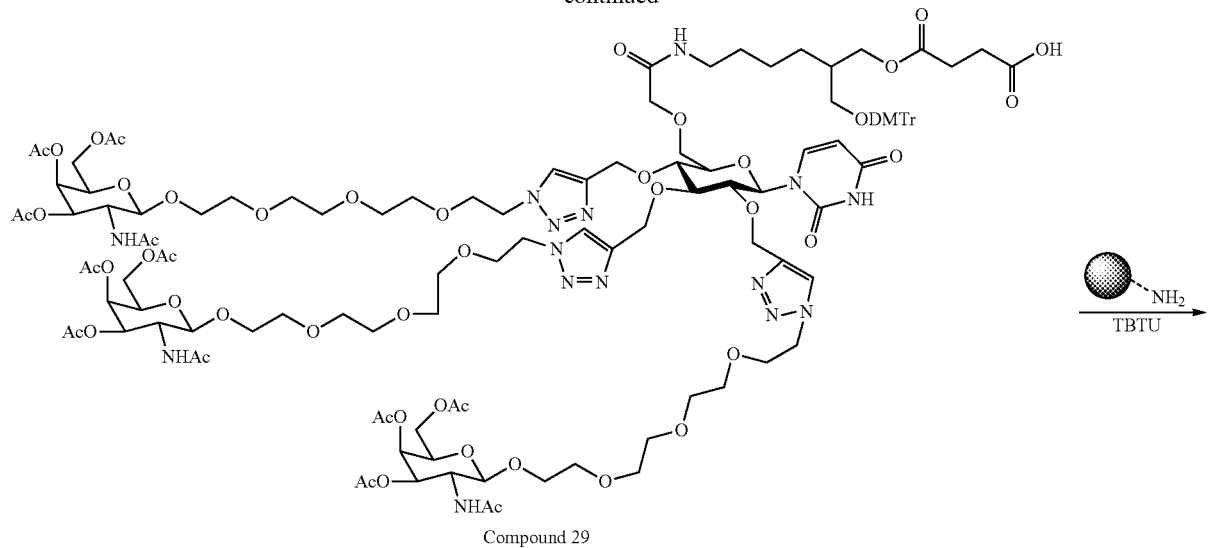
Compound 29
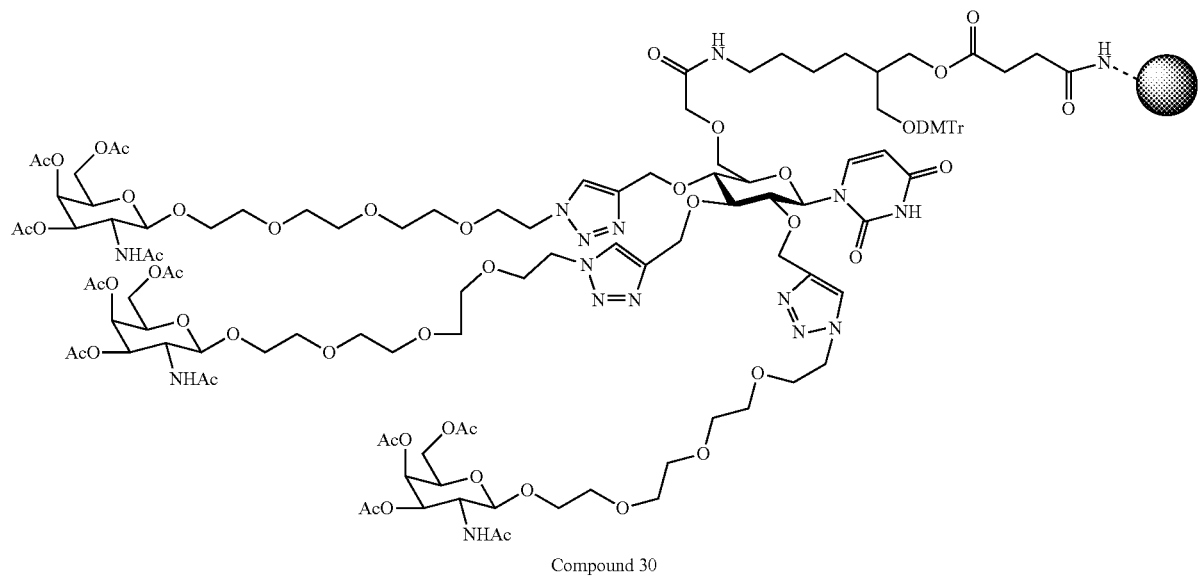
Compound 30
Compound 14 is first reacted with succinic anhydride to converted to the corresponding succinate analog Compound 29, then attached to a solid support with amino functionalities to form solid support bound Compound 30.
Example 8. Preparation of Trivalent GalNAc Analogs Compounds 31 and 33
Scheme 8A: Preparation of Compound 31
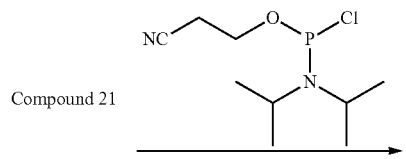

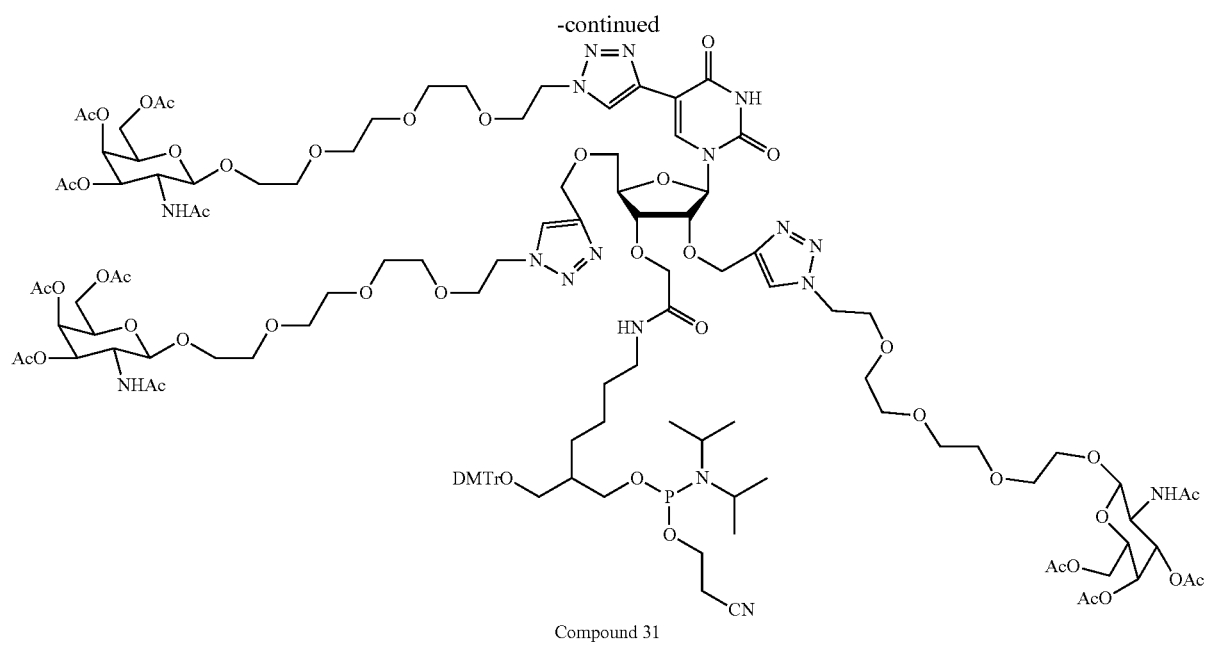
Compound 31
Compound 31 may be prepared from Compound 21 according to Scheme 8A.
Scheme 8B. Preparation of Compound 33 attached to a solid support
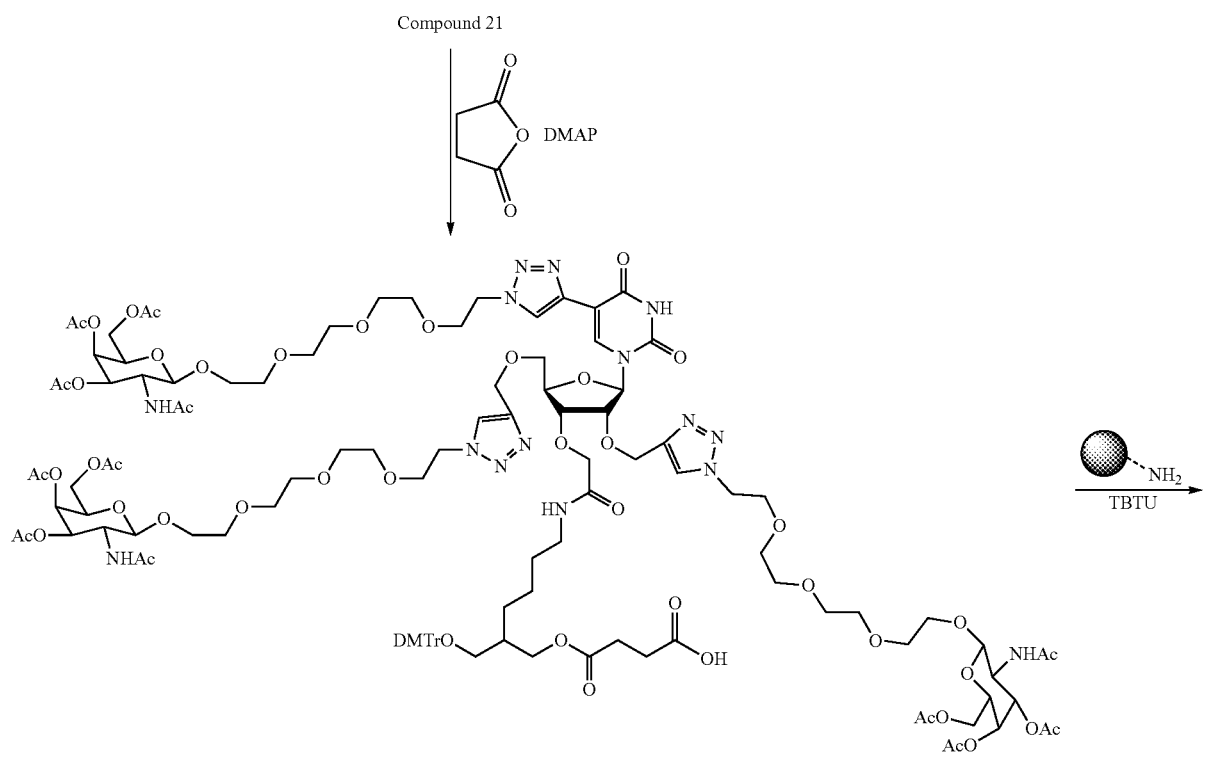
Compound 32

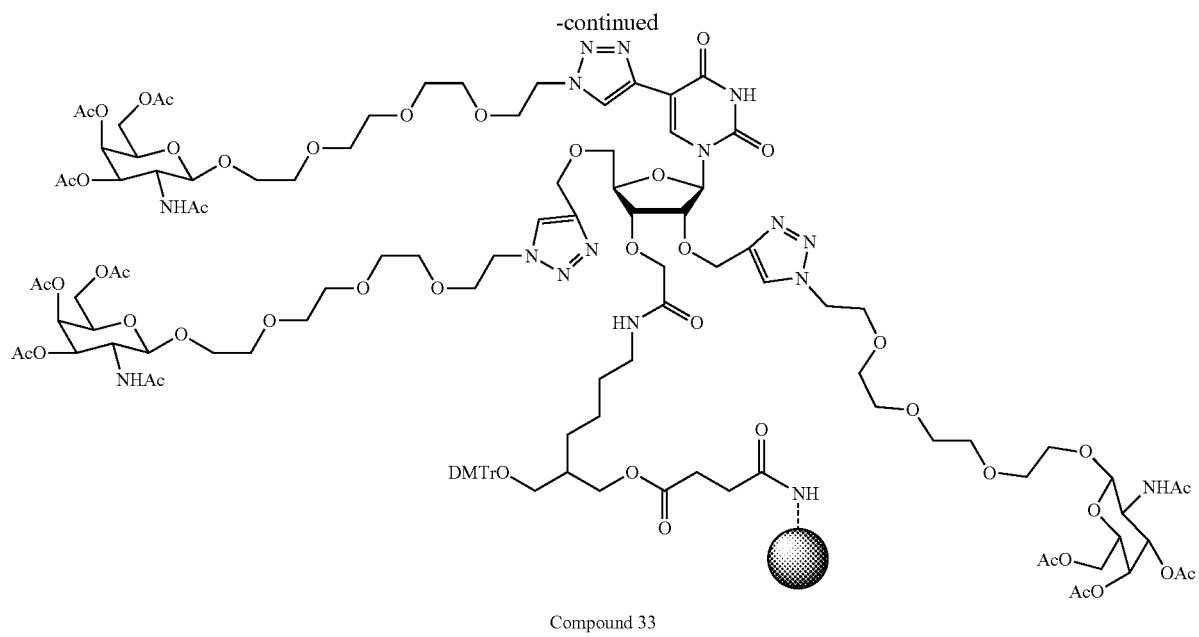
Compound 33
Compound 21 is first reacted with succinic anhydride to converted to the corresponding succinate analog Compound 32, then attached to a solid support with amino functionalities to form solid support bound Compound 33.
Example 9. Preparation of Trivalent GalNAc Analogs Compounds 34 and 36
Scheme 9A. Preparation of Compound 34
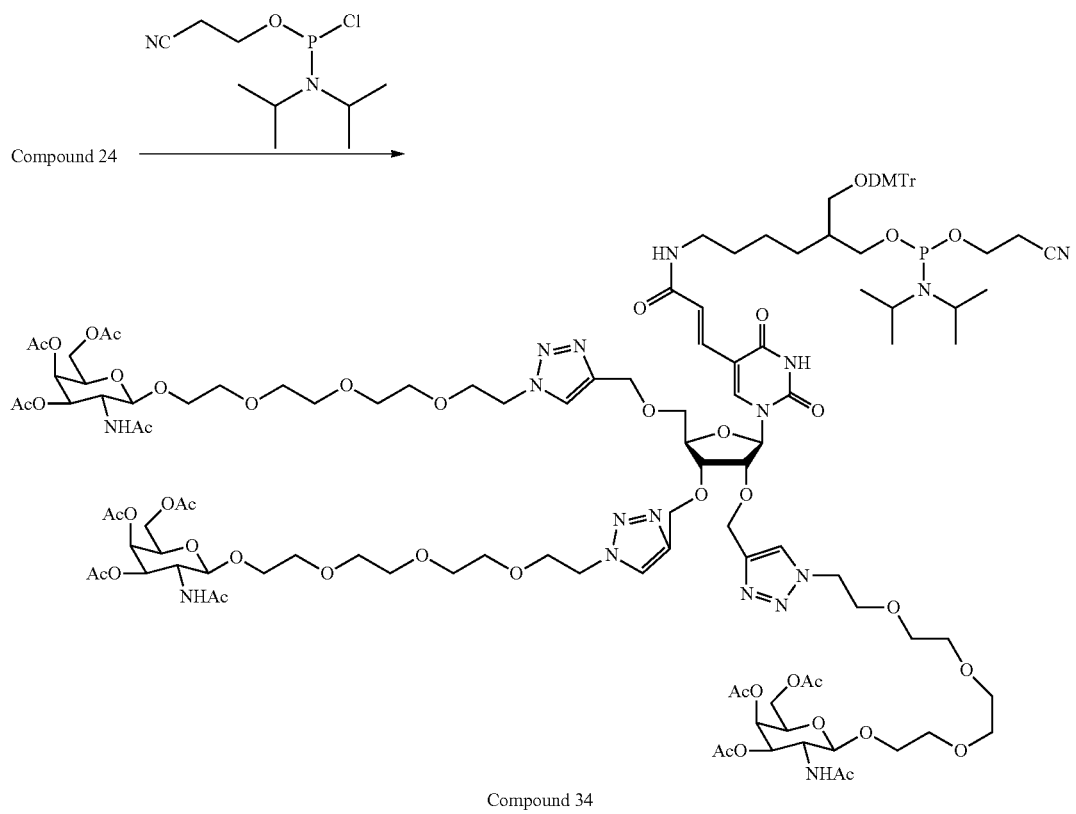
Compound 34

Compound 34 may be prepared from Compound 24 according to Scheme 9A.
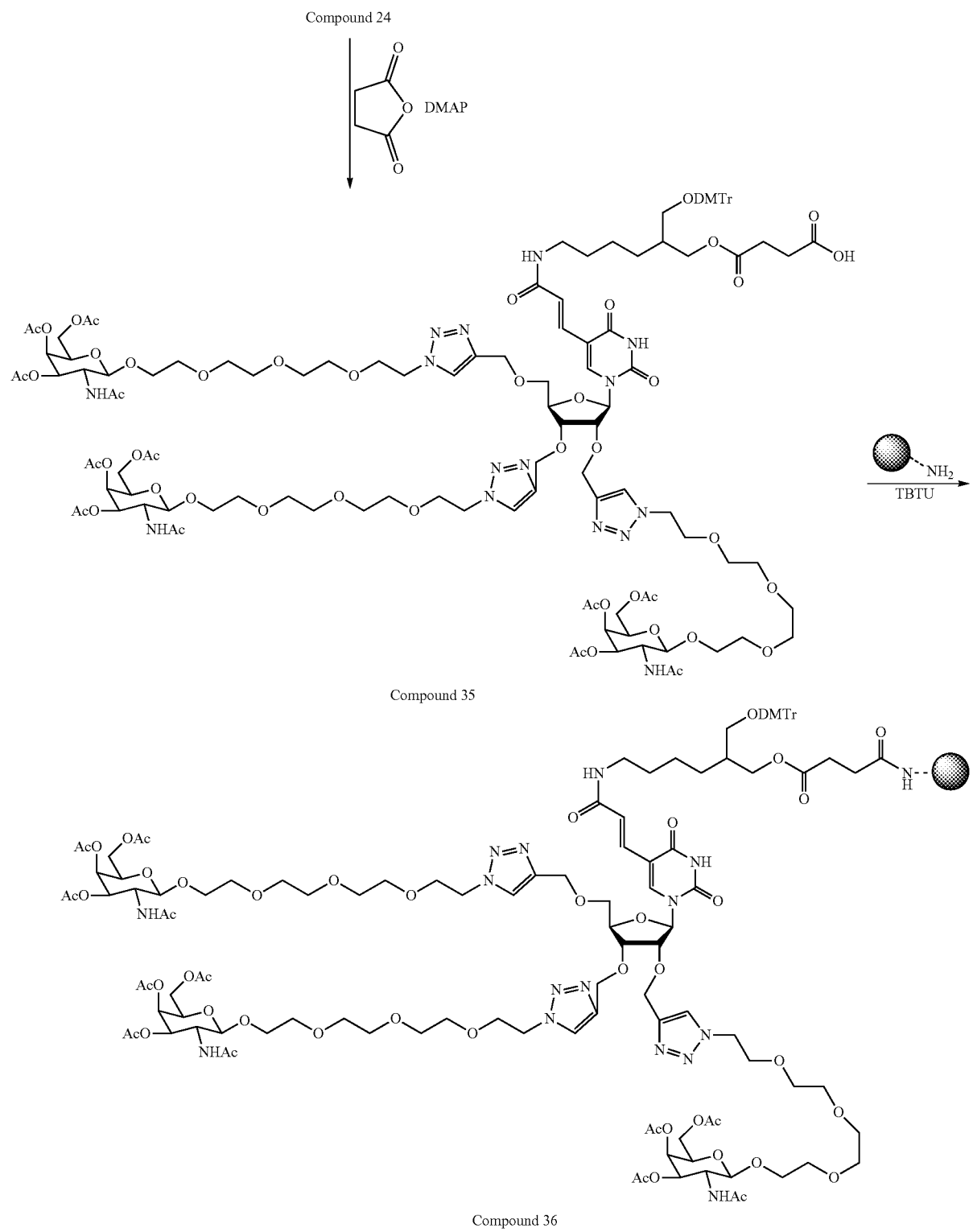
Scheme 9B. Preparation of Compound 36 attached to a solid support
Compound 24 is first reacted with succinic anhydride to converted to the corresponding succinate analog Compound 35, then attached to a solid support with amino functionalities to form solid support bound Compound 36.

Example 10. General Procedure for the Preparation of Trivalent GalNAc Analog

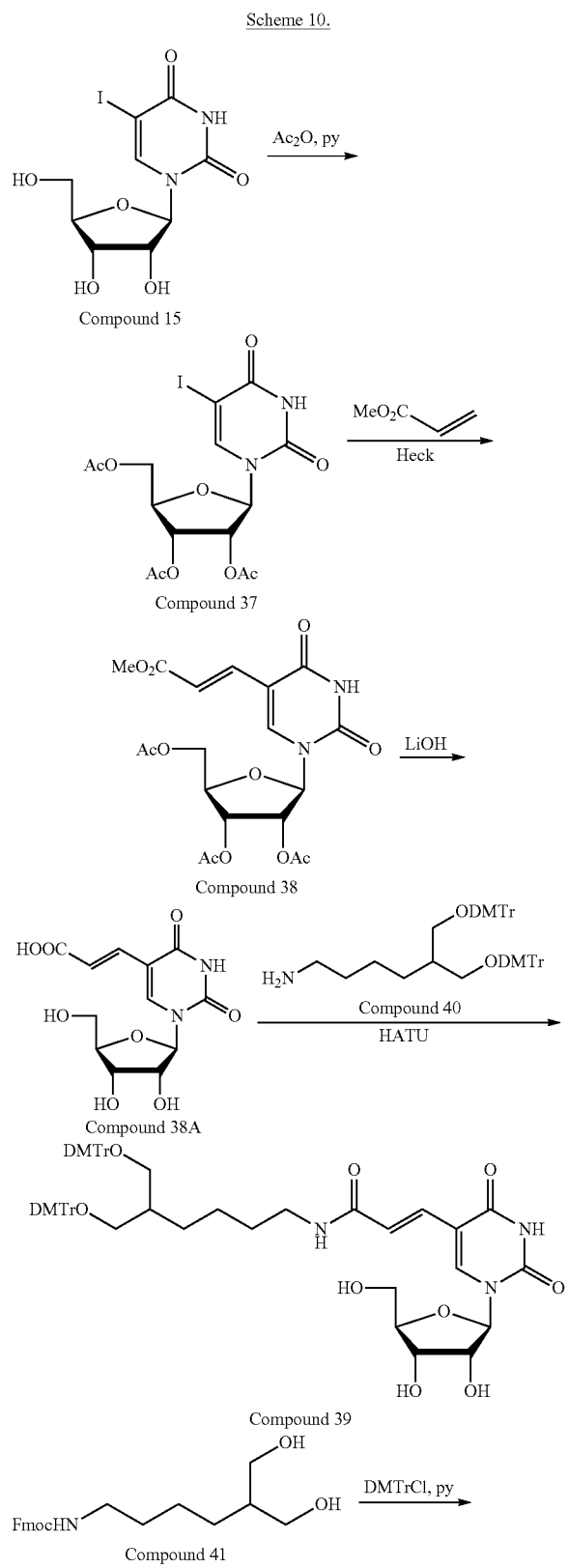

Scheme 10.

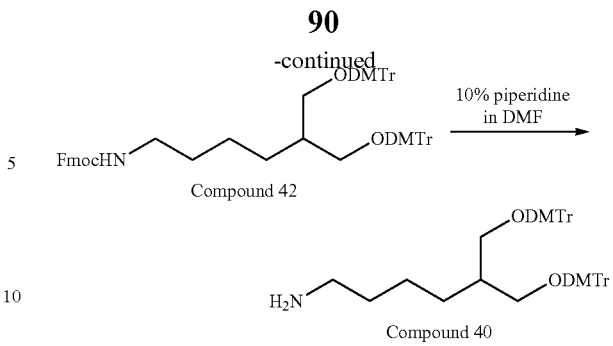

Preparation of Compound 37: Compound 15 (8.8 g, 23.8 mmol) was dissolved in pyridine (40 ml) at room temperature. Acetic anhydride (40 ml) was added, and the reaction was monitored by TLC. Upon completion, the solvents were removed and the residue was azeotroped with toluene to form Compound 37, (15.3 g) which was used directly for the next step without further purification. MS: [M−H]$^-$ calc: 495.00, found: 495.2.

Preparation of Compound 38: Crude Compound 37 (15.3 g), palladium acetate (1.6 g, 7.1 mmol), methyl acrylate (6.0 g, 71.4 mmol) and triethylamine (23.8 g, 238 mmol) were dissolved in DMF (125 ml). The mixture was purged with nitrogen before it was heated to 100° C. overnight. The reaction was monitored by TLC. Upon completion, the mixture was cooled to room temperature, concentrated under vacuum, and diluted with ethyl acetate (500 mL). The ethyl acetate mixture was then washed with water (3×500 mL) and brine (500 mL), dried over sodium sulfate, and concentrated. The residue was purified by flash chromatography using 0-20% MeOH/DCM to afford Compound 38 (10.0 g, 92% over 2 steps) as a red solid. MS: [M−H]$^-$ calc: 453.12, found: 453.2.

Preparation of Compound 38A: Compound 38 (10 g, 22 mmol) was dissolved in tetrahydrofuran/water (100 mL/100 mL). Lithium hydroxide monohydrate (7.7 g, 220 mmol) was added to the solution. The reaction was monitored by LCMS. Upon completion, the mixture was neutralized with 1 N HCl, and the solvents were removed to afford crude Compound 38A as a brown solid (15.0 g). MS: [M+AcO]$^-$ calc: 373.08, found: 373.1.

Preparation of Compound 42: Compound 41 (2.2 g, 6.0 mmol) was dissolved in pyridine (20 mL) at room temperature. Dimethoxy trityl chloride (6.6 g, 19.5) was added, and the reaction was monitored by TLC. Upon completion, the reaction was quenched by the addition of methanol (5 mL). The solvents were removed and the residue was azeotroped with toluene to form crude Compound 42 (15.3 g) which was used directly for the next step without further purification. MS: [M+NH$_4$]$^+$ calc: 991.46, found: 991.8.

Preparation of Compound 40: Piperidine (20 mL 10% DMF solution) was added to crude Compound 42 at room temperature. The reaction was monitored by TLC. Upon completion, the solvents were removed, the residue was redissolved in ethyl acetate (50 mL) and washed with sodium bicarbonate (2×50 mL) and brine (50 mL). The organic phase was dried, concentrated, and the residue was purified by flash column chromatography using 0-20% MeOH/DCM with 0.5% triethylamine to afford Compound 40 (2.5 g, 55% for 2 steps) as a white powder. MS: [M+H]$^+$ calc: 752.39, found: 752.6.

Preparation of Compound 39: Compound 38A (0.63 g, 2 mmol), Compound 40 (2.2 g, 3 mmol), HATU (1.37 g, 3.6 mmol), and triethylamine (1.0 g, 10 mmol) were dissolved in DMF/THF (10 mL/10 mL). The reaction was stirred at room temperature and monitored by TLC. Upon completion, the mixture was diluted with ethyl acetate (50 mL), washed with water (3×50 mL) and brine (50 mL), dried and concentrated to give Compound 39. MS: [M+AcO]⁻ calc: 1106.69, found: 1107.8.

Compound 24 may then be prepared from Compound 39 in a manner analogous to that described above in Scheme 5.

Example 11. General Procedure for the Preparation of Trivalent GalNAc Analog

Scheme 11.

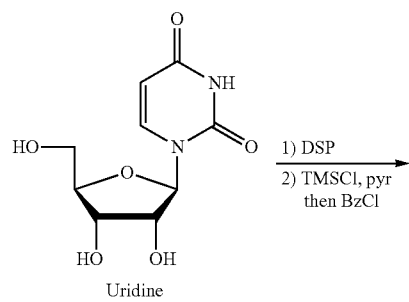
Uridine

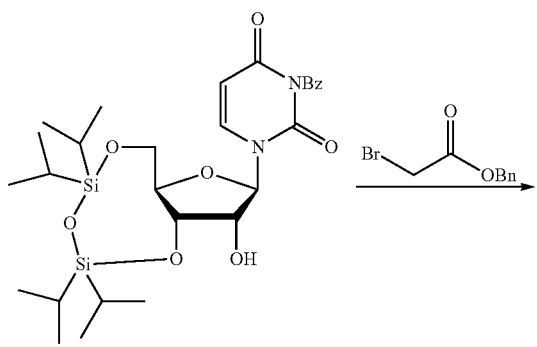
Compound 43

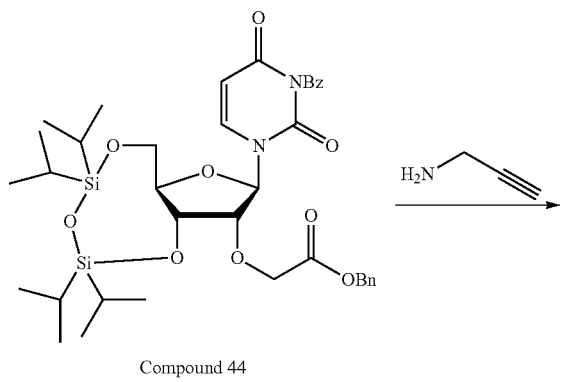
Compound 44

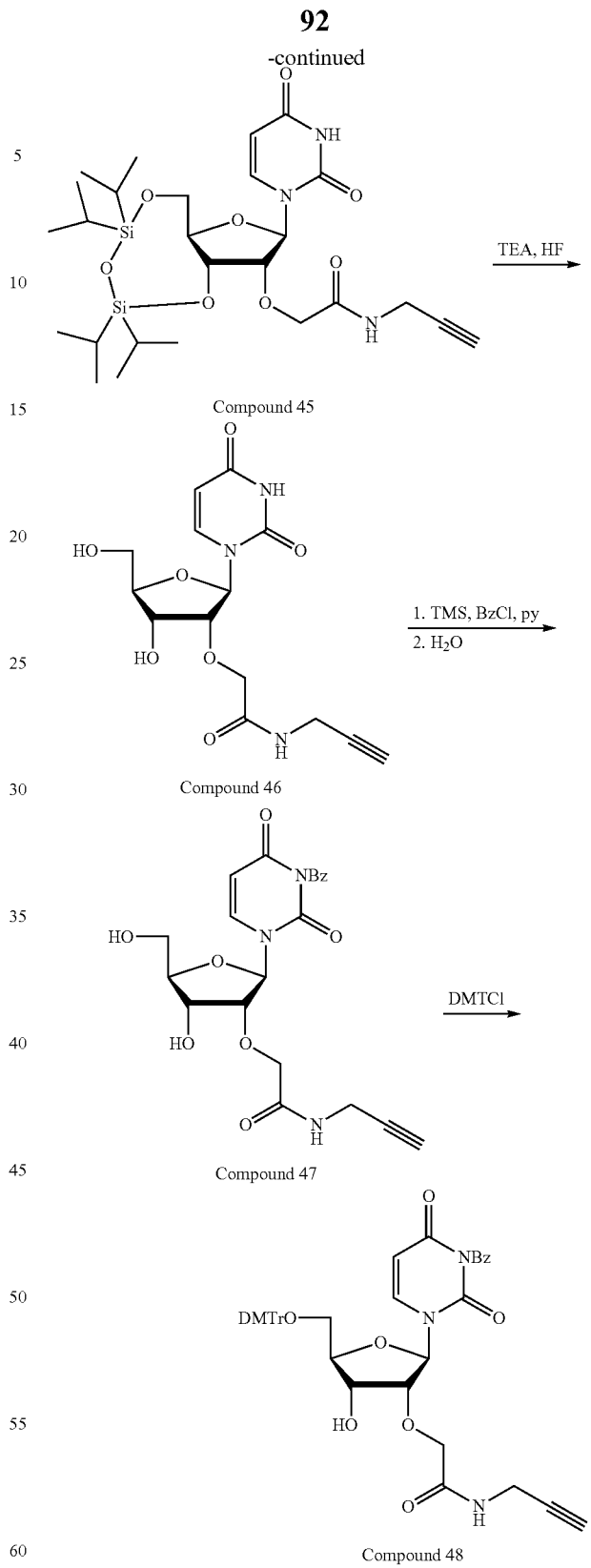

Preparation of Compound 43: Uridine (24.4 g) was dissolved in pyridine (250 mL). TIPSCl₂ was added dropwise at 0° C. The mixture was allowed to warm to room temperature. The reaction was monitored by TLC. Upon completion, the solvents were evaporated, the residue was redissolved in DCM (300 mL), and washed with water (3×300 mL) and brine (300 mL). The organic phase was dried to form crude Compound 43 (52 g), which was then redissolved in pyridine (300 mL). TMSCl (17 g, 157 mmol) was added at 0° C., then the reaction was stirred at room temperature for 30 minutes, until TLC showed indicated that the reaction had gone to completion. Once complete, the reaction mixture was cooled to 0° C., BzCl (16.4 g, 126 mmol) was added, and the mixture was allowed to warm to room temperature and stirred overnight. Water (2 volumes) was added to the mixture at room temperature and stirred for 4 hours. The reaction was monitored by TLC until the complete conversion of the intermediates was observed. The solvents were removed, and the residue was diluted with DCM (500 mL), washed with NaHCO$_3$ (500 mL), water (3×500 mL), and brine (500 mL). The organic phase was dried and concentrated, the residue was purified by flash column chromatography with DCM/MeOH=0-10% to afford Compound 43 (45 g, 76%) as a colorless oil. MS: [M+AcOH—H]$^-$ calc: 649.25, found: 649.6.

Preparation of Compound 44: Compound 43 (12 g, 20 mmol) was dissolved in dry DMF (120 mL) and NaH (2.4 g, 60% in mineral oil, 60 mmol) was added at 0° C. The mixture was stirred for 30 minutes before bromobenzyl acetate (9 g, 39 mmol) was added. The reaction was monitored by TLC. Upon completion, the reaction was quenched by pouring into aqueous ammonium chloride (500 mL). The mixture was extracted with ethyl acetate (500 mL), washed with water (3×500 ml) and brine (500 mL). The organic phase was dried and concentrated. The residual was purified by flash column chromatography with Ethyl Acetate/DCM=0-15% to afford Compound 44 (13 g, 87%) as a yellow solid. MS: [M+AcOH—H]$^-$ calc: 797.30, found: 797.7.

Preparation of Compound 45: Compound 44 (13 g, 17.3 mmol) was dissolved in DCM (30 ml). Propargyl amine (13 ml) was added and the mixture was stirred overnight at 40° C. Upon completion, the solvents were evaporated, and the crude residue was purified by flash column chromatography with MeOH/DCM=0-6% to afford Compound 45 (9 g, 90%) as a yellow solid. MS: [M+AcOH—H]$^-$ calc: 640.26, found: 640.5.

Preparation of Compound 46: Compound 45 (9 g, 15.5 mmol) was dissolved in THF (100 mL) and triethylamine hydrofluoride (4 mL, 24.5 mmol) was added at 0° C. The mixture was monitored by TLC. Upon completion, the solvents were evaporated and the crude residue was purified by flash column chromatography with MeOH/DCM=0-25% to afford Compound 46 (5.9 g, 113%) as an orange oil. MS: [M+AcOH—H]$^-$ calc: 398.11, found: 398.1.

Preparation of Compound 47: Compound 46 (5.9 g, 17.4 mmol) was dissolved in pyridine (60 ml). TMSCl (5.7 g, 52.4 mmol) was added at 0° C. and the reaction was stirred at room temperature for 30 minutes, until TLC showed that this step was complete. The mixture was cooled to 0° C. and BzCl (3.4 g, 26.2 mmol) was added. The mixture was stirred overnight. Water (2 volumes) was added to the mixture at room temperature and the mixture was stirred for 4 hours. The reaction was monitored by TLC until the complete conversion of the intermediates was observed. The solvents were removed, and the residue was diluted with ethyl acetate (200 mL), washed with NaHCO$_3$ (200 mL), water (3×200 mL), and brine (200 mL). The organic phase was dried and concentrated, and the residue was purified by flash column chromatography with MeOH/DCM=0-10% to afford Compound 47 (1.9 g, 25%) as a brown-red solid. MS: [M+NH$_4$]$^-$ calc: 461.13, found: 461.4.

Preparation of Compound 48: Compound 47 (1.9 g, 4.3 mmol) was dissolved in pyridine (20 ml), DMTrCl (1.7 g, 5.1 mmol) was added at 0° C., and the reaction was stirred at room temperature overnight. The reaction was monitored by TLC. Upon completion, the reaction was quenched by the addition of MeOH (5 mL). The solvents were removed, and the residue was purified by flash column chromatography with MeOH/DCM=0-10% to afford Compound 48 (1.18 g, 37%) as a white solid. MS: [M+NH$_4$]$^-$ calc: 763.26, found: 763.4.

Trivalent GalNAc Analog can then be prepared according to Scheme 12 below.

Scheme 12.

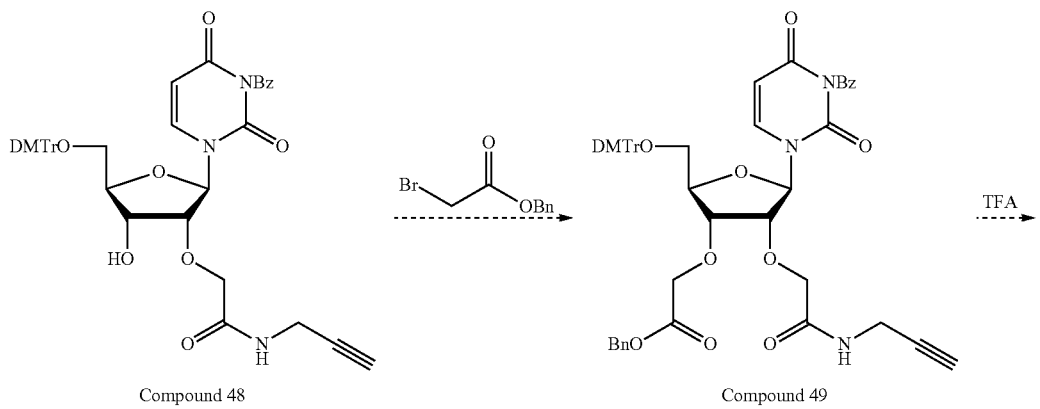

Compound 48　　　　　　　　　　Compound 49

-continued
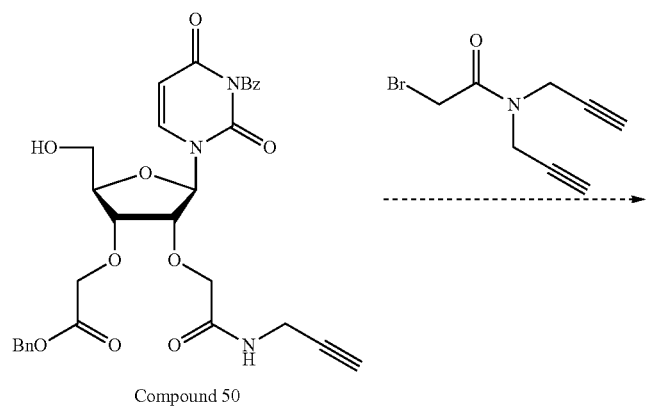
Compound 50
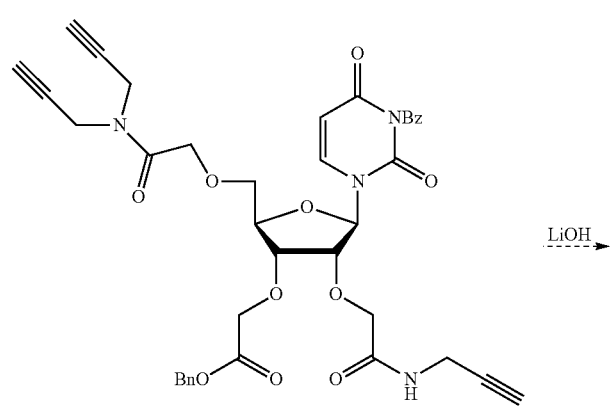
Compound 51
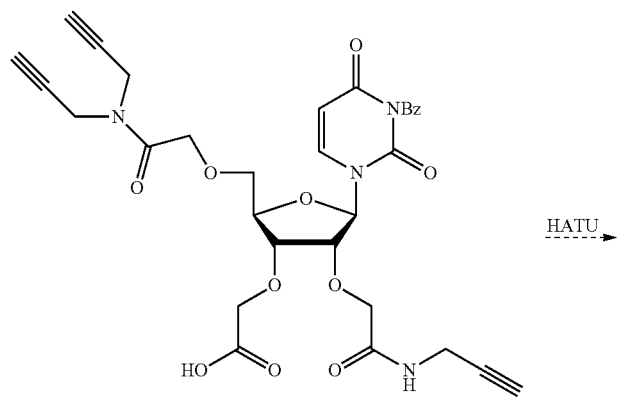
Compound 52

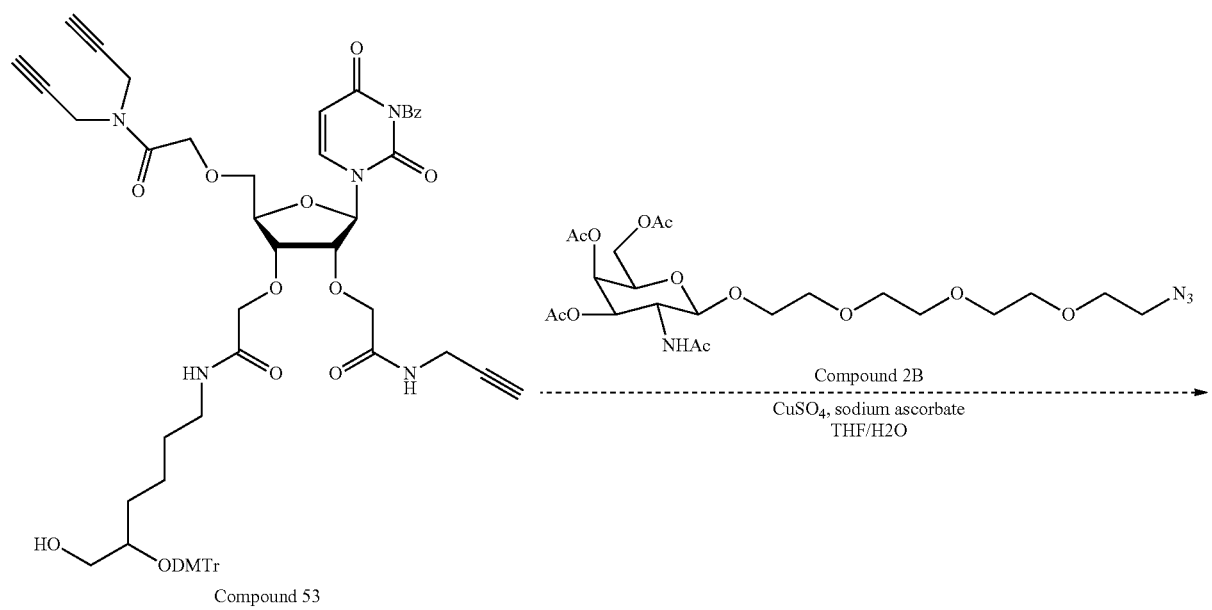
Compound 53
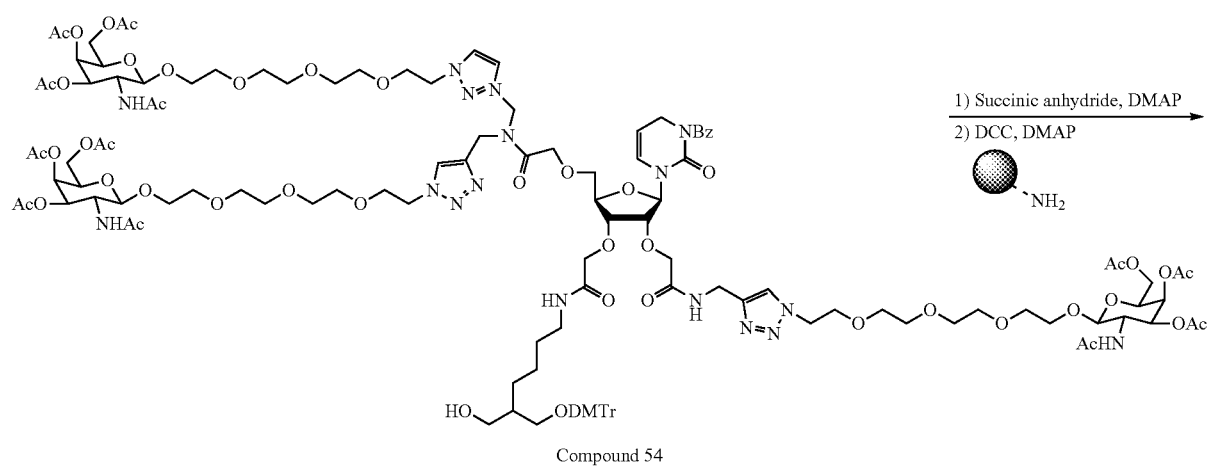
Compound 54
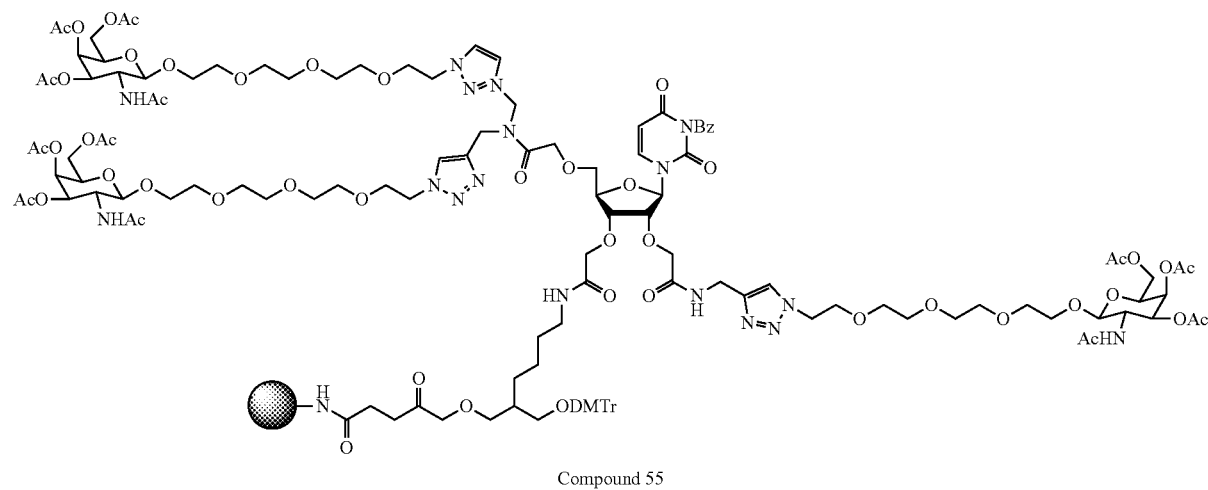
Compound 55

Example 12. General Procedure for the Preparation of Trivalent GalNAc Analog
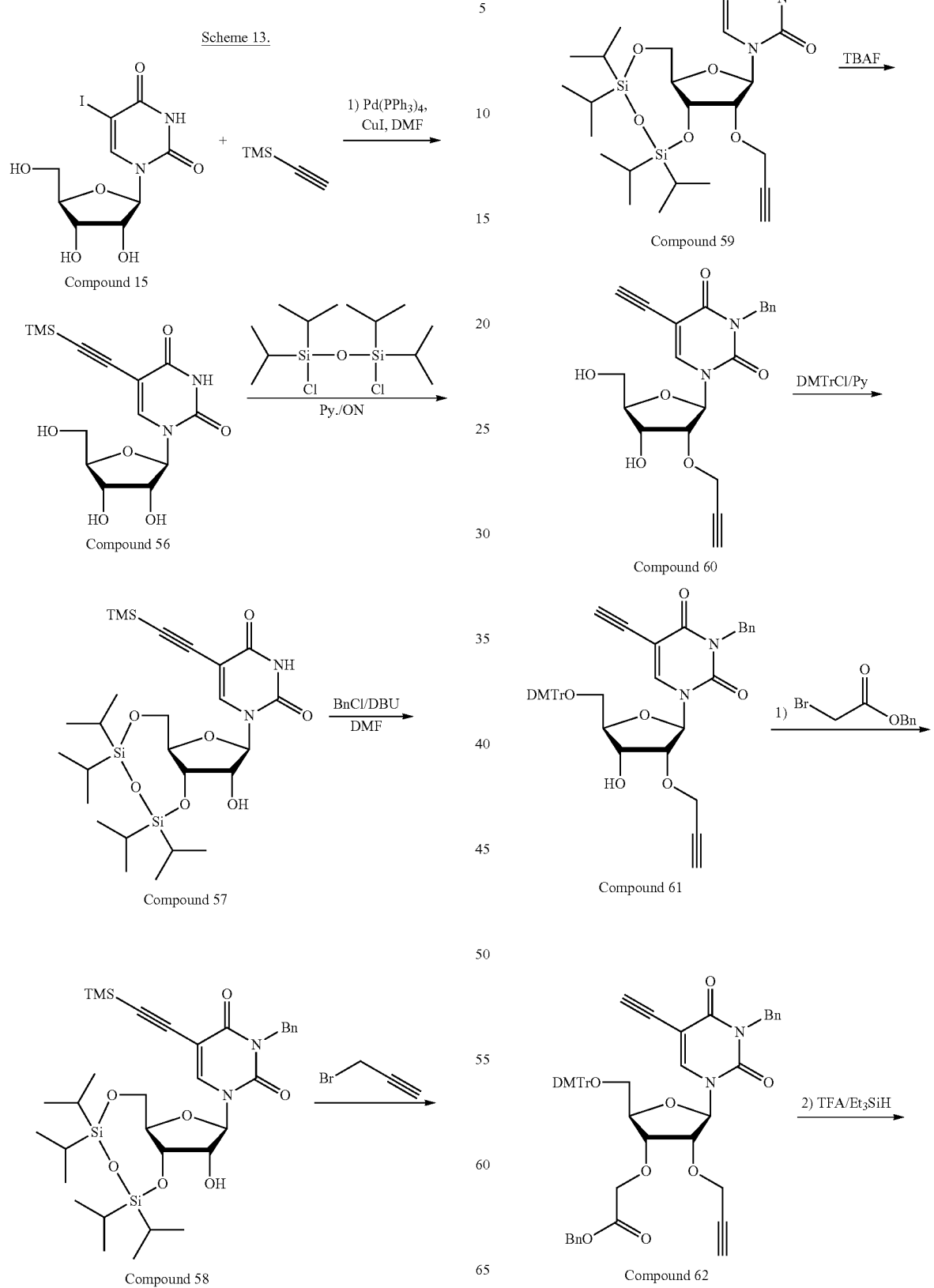

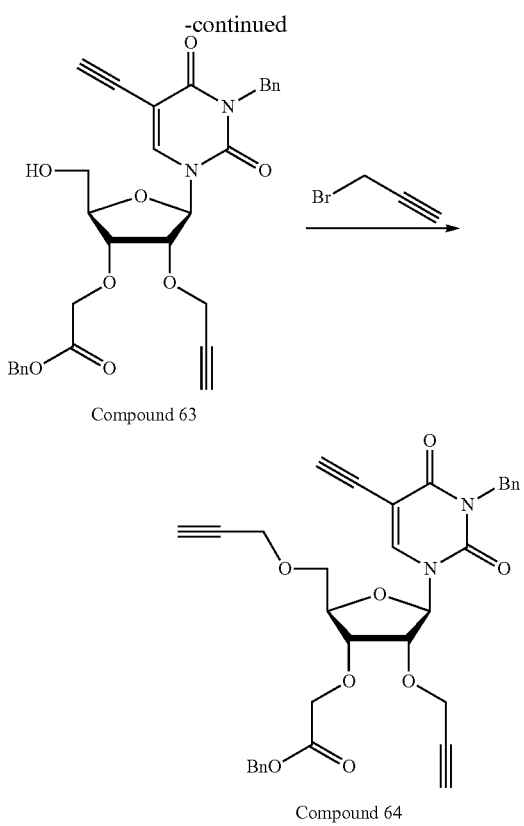

Compound 63

Compound 64

Preparation of Compound 56: To a solution of commercial starting material 5-iodouridine (Compound 15) (5.0 g, 13.5 mmol) in DMF (60 mL) was added Pd(PPh3)₄ (0.78 g, 0.67 mmol, 5%), CuI (0.26 g, 1.35 mmol, 10%), TMS-acetylene (2.39 g, 24.3 mmol, 1.8 eg) and triethylamine (3.76 mL, 27.0 mmol, 2 eq). The reaction mixture was purged with argon and stirred at room temperature overnight. HPLC analysis indicated the reaction was complete. The reaction mixture was concentrated in vacuo to a dark oil. The crude oil was diluted with ethyl acetate and washed with water. The organic layer was then washed with brine, dried over anhydrous sodium sulfate, filtered, and concentrated. The crude material was purified on a silica gel column with 70-100% ethyl acetate:hexane followed by 1-10% MeOH/DCM. All desired products were pooled to give Compound 56 (3.95 g, 11.6 mmol, 86%) as a tan solid. MS: found: [M+AcOH—H]⁻=399.2; calc: [M+AcOH—H]⁻= 399.2.

Preparation of Compound 57: To a solution of Compound 56 (6.42 g, 18.9 mmol) in anhydrous pyridine (60 mL) was slowly added 1,3-dichloro-1,1,3,3-tetraisopropyldisiloxane (7.24 mL, 22.6 mmol, 1.2 eq) at 0° C. The reaction mixture was slowly warmed to room temperature and stirred overnight. HPLC indicated the reaction was complete. The reaction mixture was concentrated to a brown solid which was diluted with ethyl acetate and water. After separation, the organic layer was washed with brine, dried over anhydrous sodium sulfate, filtered, and concentrated. The crude material was purified on a silica gel column (0-50% EA/Hex) to provide Compound 57 (7.79 g, 13.4 mmol, 71%) as a pale-yellow foam. MS: found: [M–H]=581.4; calc: [M–H]⁻=581.4.

Preparation of Compound 58: To a solution of Compound 57 (4.39 g, 7.53 mmol) in anhydrous DMF (20 mL) was added benzyl bromide (1.41 g, 0.98 mL, 8.25 mmol, 1.1 eq). DBU (1.25 g, 1.23 mL, 8.25 mmol, 1.1 eq) was then added slowly. Then the mixture was stirred at room temperature for 3 hours, until TLC indicated completion of the reaction. The mixture was concentrated in vacuo and the resulting crude material was diluted with ethyl acetate and water. After separation, the organic layer was washed with brine, dried over anhydrous sodium sulfate, filtered, and concentrated. The crude material was purified on a silica gel column (0-30% ethyl acetate/hexane) to give Compound 58 (4.94 g, 7.34 mmol, 97%) as a white foam. MS: found: [M+H]⁺= 673.6; calc: [M+H]⁺=673.6.

Preparation of Compound 59: To a solution of Compound 58 (2.1 g, 3.12 mmol) in anhydrous DMF (10 mL), propargyl bromide (816 mg, 0.63 mL, 6.86 mmol, 2.2 eq) was added one portion at room temperature. The mixture was cooled to 0° C. and NaH (137 mg, 60% in mineral oil, 3.43 mmol, 1.1 eq) was added in one portion. The reaction stirred at 0° C. for 30 min, after which the reaction was allowed to stir at room temperature overnight. TLC indicated the reaction was complete. The reaction mixture was then cooled to 0° C. and quenched with DI water and extracted with ethyl acetate. The organic layer was washed with brine, dried over Na₂SO₄, filtered, and concentrated. The residue was purified by column chromatography eluting with EA/Hex (0-20% ethyl acetate in hexane) to provide Compound 59 (1.74 g, 2.45 mmol, 78%) as a light-yellow foam. Direct mass analysis did not give the desired mass. However, upon silyl deprotection the desired mass was observed. MS: found: [M–H]⁻=395.7; calc: [M–H]⁻=395.7.

Preparation of Compound 60: To a solution of Compound 59 (1.74 g, 2.45 mmol) in THF (15 mL) was added TBAF (8.1 mL, 1 M solution in THF, 8.1 mmol, 3.3 eq) at 0° C. and the reaction mixture was allowed to warm to room temperature and stir overnight. TLC indicated all starting material was consumed. The reaction was then cooled to 0° C., quenched with DI water, and diluted with ethyl acetate. The organic layer was washed with brine, dried over anhydrous sodium sulfate, filtered, and concentrated. The crude material was purified on a silica gel column (0-80% ethyl acetate/hexane) to provide Compound 60 (0.72 g, 74%) as a white foam. MS: found: [M+H]⁺=397.1; calc: [M+H]= 397.1.

Preparation of Compound 61: To a solution of Compound 60 (1.68 g, 4.24 mmol) in anhydrous pyridine (30 mL) was added DMTrCl (1.87 g, 5.51 mmol, 1.3 eq, 4,4'-Dimethoxytriphenylmethyl chloride) at 0° C. The reaction was allowed to warm to room temperature and stir overnight. The reaction was quenched with MeOH and concentrated in vacuo. The residue was diluted with ethyl acetate and washed with aqueous saturated sodium bicarbonate solution. The organic layer was then washed with brine, dried over anhydrous sodium sulfate, filtered, and concentrated. The crude material was purified on a silica gel column (0-50% ethyl acetate/hexane, 0.5% triethylamine additive in hexane) to provide Compound 61 (2.82 g, 4.04 mmol, 95%) as a white foam. MS: found: [M+NH₄]⁺=716.4; calc: [M+NH₄]⁺= 716.4.

Preparation of Compound 62: To a solution of Compound 61 (2.82 g, 4.04 mmol) in anhydrous DMF (30 mL) was added benzyl bromoacetate (1.11 g, 4.84 mmol, 1.2 eq) at room temperature. The mixture was then cooled to 0° C. Potassium tert-butoxide (0.5 g, 4.44 mmol, 1.1 eq) was added in one portion. The reaction was stirred at the same temperature for 30 min, after which one more batch of benzyl bromoacetate and potassium tert-butoxide was added sequentially. The reaction was then allowed to slowly warm to room temperature and stir overnight. The reaction mixture was then cooled to 0° C., quenched with DI water, and neutralized with citric acid to pH=4. The reaction mixture was extracted with ethyl acetate. The organic layer was washed with DI water, brine, dried over anhydrous sodium sulfate, filtered and concentrated. The crude material was purified on a silica gel column (0-50% ethyl acetate/hexane, 0.5% triethylamine additive in hexane) to provide Compound 62 (1.5 g, 1.77 mmol, 44%) as a white foam. MS: found: $[M+NH_4]^+$=864.6; calc: $[M+NH_4]^+$=864.6.

Preparation of Compound 63: To a solution of Compound 62 (1.5 g, 1.77 mmol) in DCM (30 mL) was added TFA (0.45 g, 3.9 mmol, 2.2 eq) at 0° C., followed by triethylsilane (0.227 g, 1.95 mmol, 1.1 eq). The reaction was allowed to warm to room temperature slowly and stir for 1.5 hrs. HPLC indicated the reaction was complete. The reaction mixture was then cooled to 0° C. and quenched with saturated aqueous sodium bicarbonate and extracted with DCM. The organic layer was washed with brine, dried over anhydrous sodium sulfate, filtered, and concentrated. The crude material was purified on a silica gel column (0-50% ethyl acetate/hexane) to provide Compound 63 (0.78 g, 1.43 mmol, 81%) as a white foam. MS: found: $[M+NH_4]^+$=562.4; calc: $[M+NH_4]^+$=562.4.

Preparation of Compound 64: To a solution of Compound 63 (0.77 g, 1.43 mmol) in anhydrous DMF (10 mL) was added propargyl bromide (428 μL, 80% in toluene, 3.15 mmol, 2.2 eq) at room temperature. The mixture was then cooled to 0° C. Potassium tert-butoxide (0.18 g, 1.57 mmol, 1.1 eq) was then added in one portion. The reaction was stirred at 0° C. for 30 min, then additional propargyl bromide (428 μL, 80% in toluene, 3.15 mmol, 2.2 eq) and potassium tert-butoxide (0.18 g, 1.57 mmol, 1.1 eq) was added sequentially, and the reaction was allowed to slowly warm to room temperature and stir overnight. The reaction was cooled to 0° C., quenched with DI water, and neutralized with citric acid to pH=4. The reaction mixture was extracted with ethyl acetate. The organic layer was washed with DI water, brine, dried over anhydrous sodium sulfate, filtered, and concentrated. The crude material was purified on a silica gel column (0-50% ethyl acetate/hexane) to provide Compound 64 (0.14 g, 0.24 mmol, 17%) as a white foam. MS: found: $[M+NH_4]^+$= 600.3; calc: $[M+NH_4]^+$=600.3.

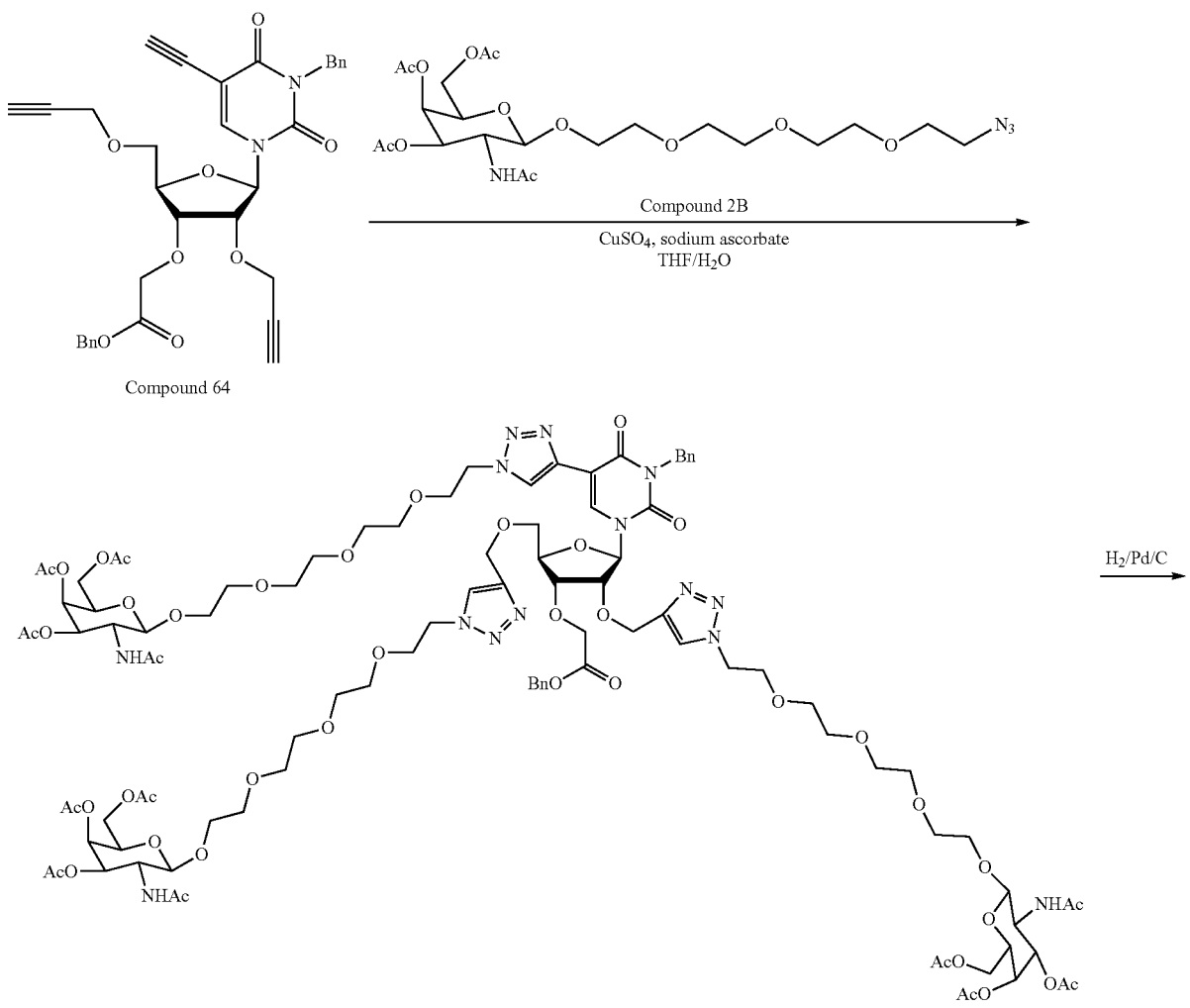

Scheme 14

Compound 65

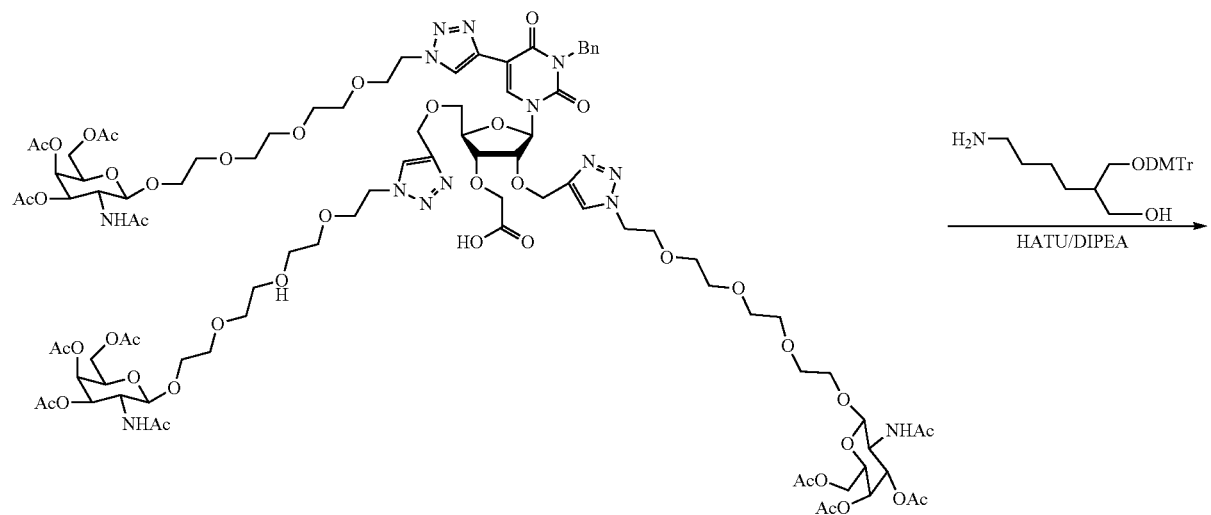
Compound 66
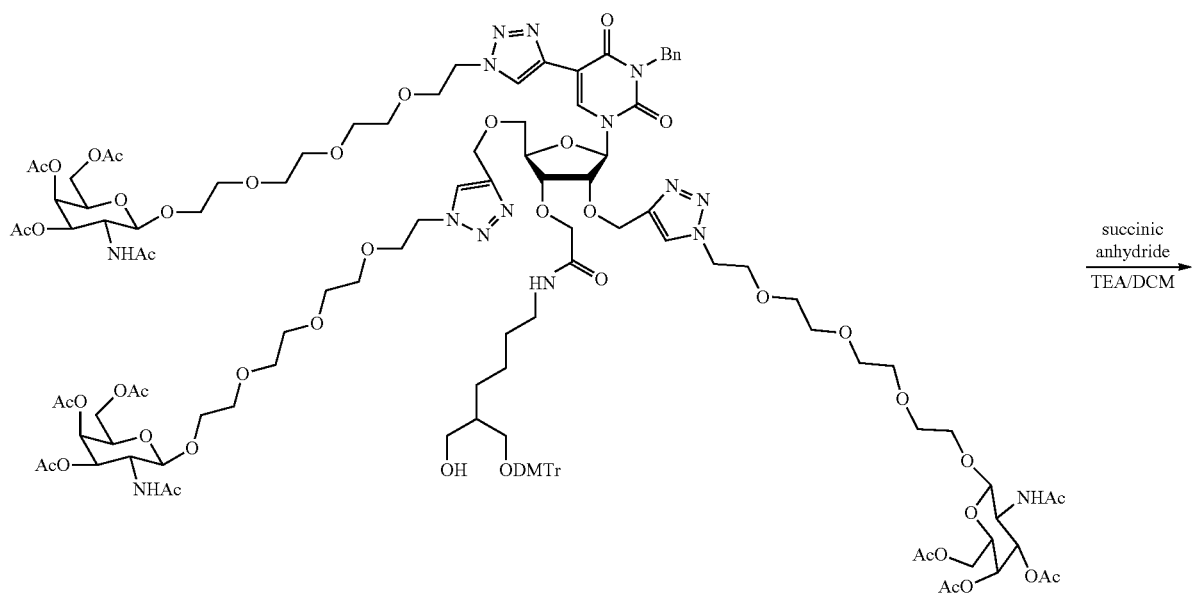
Compound 67

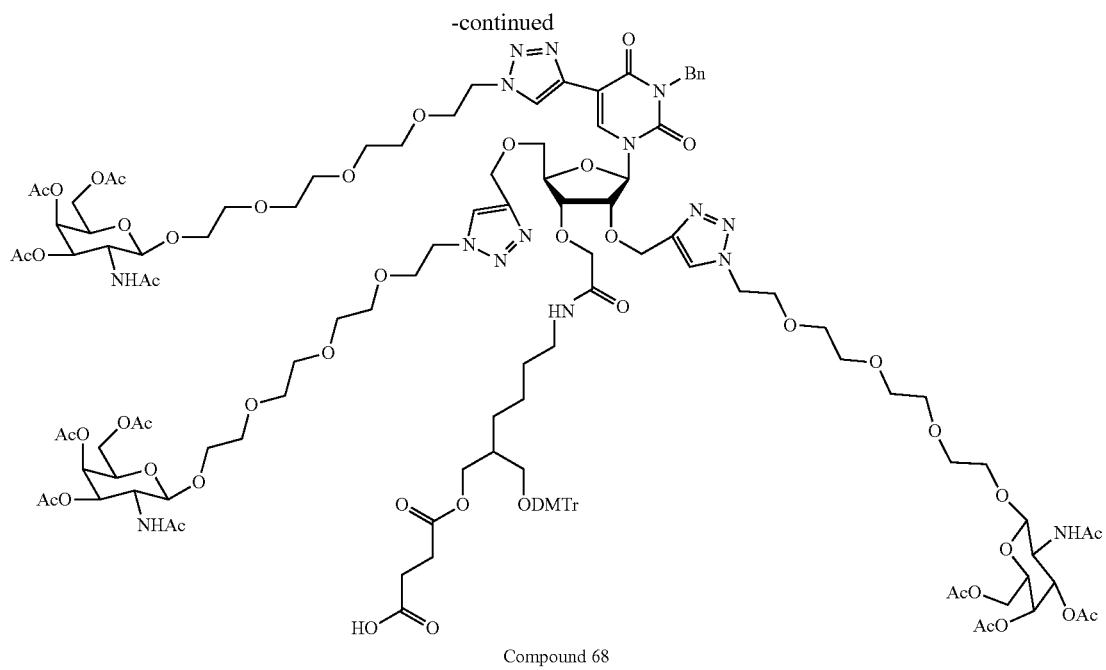

Compound 68

Synthesis of Compound 65: To a solution of Compound 64 (0.14 g, 0.24 mmol) in THF (4 mL) was added GalNAc azide (Compound 2B) (0.4 g, 0.73 mmol, 3.1 eq), and the mixture was cooled to 0° C. L-Asc sodium salt (0.16 g, 0.83 mmol, 3.5 eq) freshly made in DI water (1 mL) was added followed by freshly made $CuSO_4 \cdot 5H_2O$ (0.18 g, 0.71 mmol, 3 eq) in DI water (1 mL). The reaction mixture was allowed to warm to room temperature and stir overnight. HPLC indicated the reaction was complete. The reaction mixture was then cooled to 0° C. and quenched with saturated sodium bicarbonate solution and extracted with DCM three times. The combined organic layers were washed with brine, dried over anhydrous sodium sulfate, filtered, and concentrated. The crude material was purified on a silica gel column (0-15% MeOH/DCM) to provide Compound 65 (0.23 g, 0.11 mmol, 46%) as a white foam. MS: found: $[M/2+NH_4]^+$= 1132.2; calc: $[M/2+NH_4]^+$=1132.2.

Synthesis of Compound 66: To a solution of Compound 65 (0.23 g, 0.11 mmol) in MeOH (10 mL) was added wet Pd/C (0.23 g), the mixture was evacuated, a hydrogen balloon was applied, and the reaction mixture was stirred at room temperature overnight. HPLC indicated the reaction was complete. The reaction mixture was filtered through a Celite pad and rinsed with MeOH. The filtrate was concentrated and used without further purification to provide Compound 66 (0.157 g, 0.073 mmol, 68%) as a white foam. MS: found: $[M/2+NH_4]^+$=1087.1; calc: $[M/2+NH_4]^+$=1087.1.

Synthesis of Compound 67: To a solution of Compound 66 (0.157 g, 0.073 mmol) in anhydrous DMF (3 mL) was added HATU (0.0293 g, 0.077 mmol, 1.05 eq). The mixture was cooled to 0° C. and DIPEA (0.01 g, 0.077 mmol, 1.05 eq) was added. The mixture was allowed to stir at the same temperature for 10 min under argon atmosphere, 6-amino-2-((bis(4-methoxyphenyl)(phenyl)methoxy)methyl)hexan-1-ol (Compound 40) (0.035 g, 0.077 mmol, 1.05 eq) was added one portion followed by DIPEA (0.01 g, 0.077 mmol, 1.05 eq). The reaction was allowed to stir at room temperature overnight. HPLC indicated the reaction was complete. The reaction mixture was diluted with ethyl acetate and water. After separation, the organic layer was washed with brine, dried over anhydrous sodium sulfate, filtered, and concentrated. The crude material was purified on a C18 flash column (0-90% $CH_3CN/H_2O$) to give Compound 67 (0.113 g, 0.044 mmol, 60%) as a white foam. MS: found: $[M/2+NH_4]^+$=1303.2; calc: $[M/2+NH_4]^+$=1303.2.

Synthesis of Compound 68: To a solution of Compound 67 (0.107 g, 0.042 mmol) in anhydrous DCM (2 mL) was added succinic anhydride (0.032 g, 0.32 mmol, 7.6 eq) in one portion, followed by triethylamine (44 µL, 0.32 mmol, 7.6 eq). The reaction was stirred at room temperature for 2 hours until HPLC indicated the reaction was complete. The reaction was concentrated to a semi-solid and purified on a C18 flash column (0-70% $CH_3CN/H_2O$) to give Compound 68 (0.08 g, 0.03 mmol, 71%) as a white foam. MS: found: $[M+AcOH-2H/2]^{2-}$=1364.2; calc: $[M+AcOH-2H/2]^{2-}$=1364.2. Conjugation to solid support is provided in Scheme 15, below.

Scheme 15

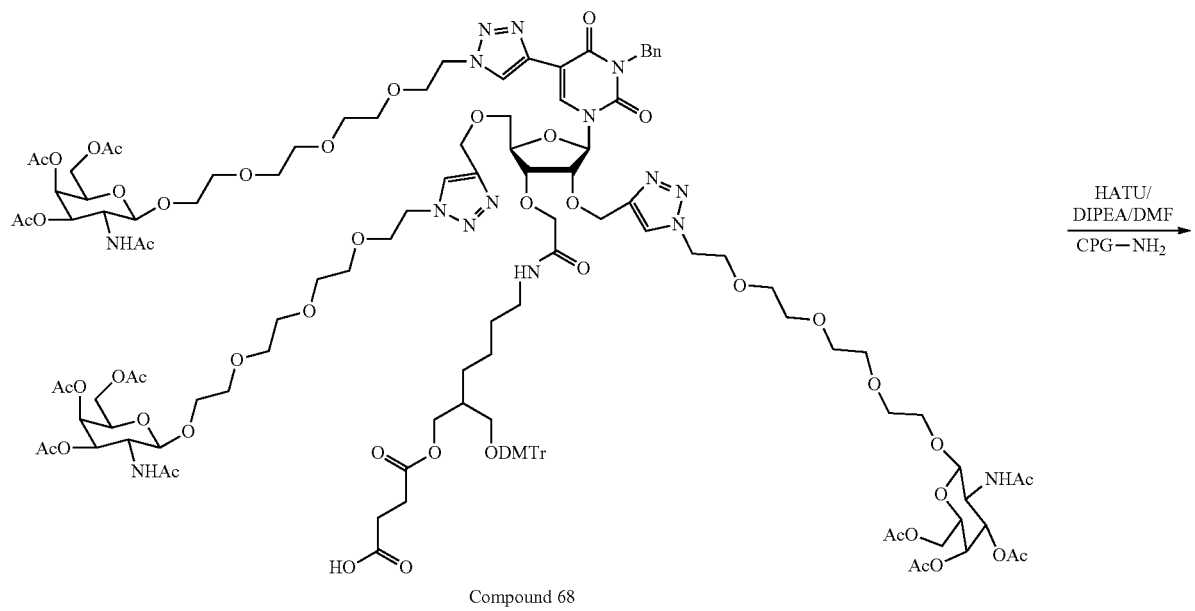

Compound 68

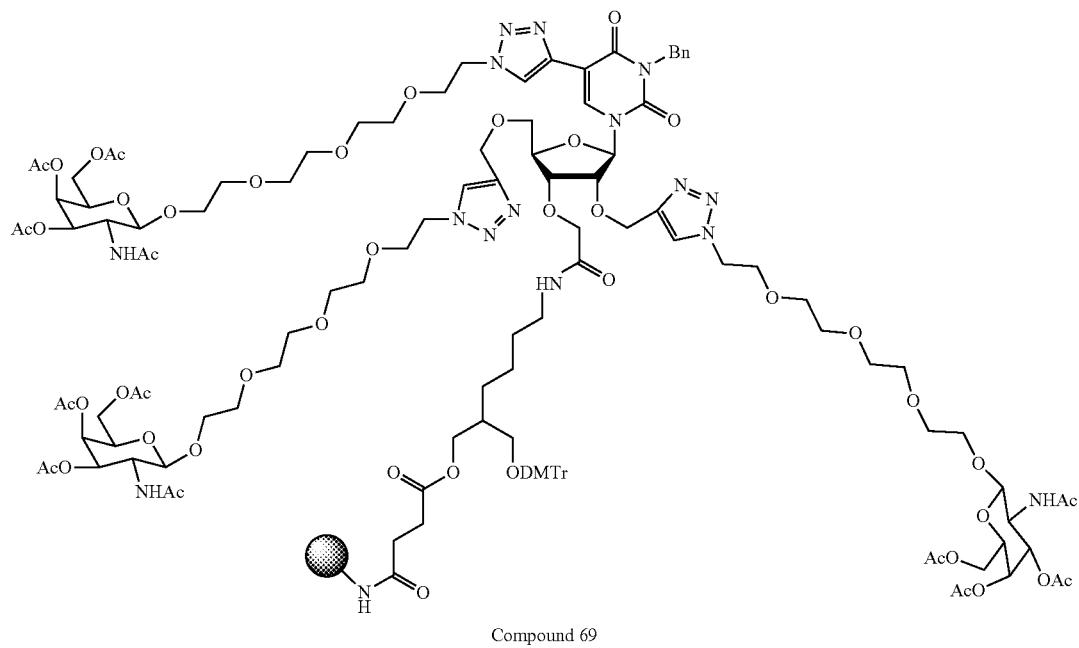

Compound 69

Synthesis of TriGalNAc CPG1 (Compound 69): To a solution of TriGalNAc succinate (Compound 68) (80 mg, 0.03 mmol) in anhydrous DMF (2 mL) was added HATU (11.4 mg, 0.03 mmol, 1 eq.) and diisopropylethylamine (6 mg, 8 µL, 0.045 mmol, 1.5 eq). The mixture was stirred at room temperature for 10 min. Pretreated LCAA CPG 500Å (0.40 g, loading: 75 µmol/g) was added followed by DIPEA (6 mg, 8 µL, 0.045 mmol, 1.5 eq). The resulting mixture was slowly agitated at 25° C. for 3 h. The mixture was then filtered, the CPG was washed with acetonitrile (1 mL×3), THF (1 mL×3) and MTBE (1 mL×2) successively. The CPG was dried under reduced pressure for 2 hrs.

To the CPG above was added a mixture of $Ac_2O$ (0.2 mL) and pyridine (0.2 mL) in anhydrous THF (1.6 mL). The resulting mixture was slowly agitated at 25° C. for 30 min. The mixture was then filtered, and this CPG was washed with THF (1 mL×1), 10% pyridine in MeOH (1 mL×2), MeOH (1 mL×2), acetonitrile (1 mL×2) and MTBE (1 mL×1) successively. The capped CPG was dried under reduced pressure for 2 hours to give the TriGalNAc CPG1 500A (Compound 69)(0.42 g, Loading was determined by standard DMTr assay by UV-Vis (498 nm) to be 40 µmol/g). Ninhydrin test: negative.

Example 13. General Procedure for the Preparation of Trivalent GalNAc Analog
Scheme 16.
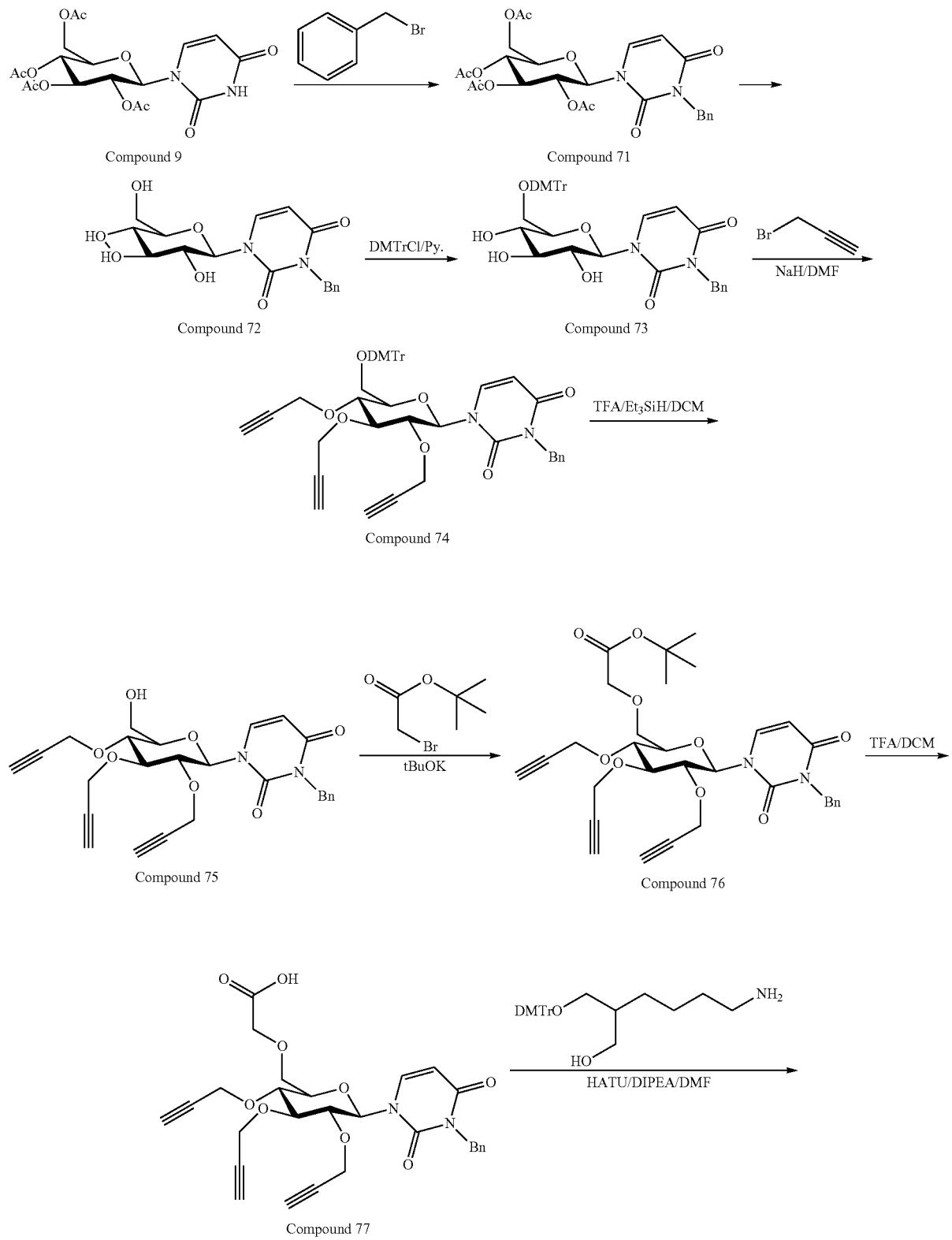

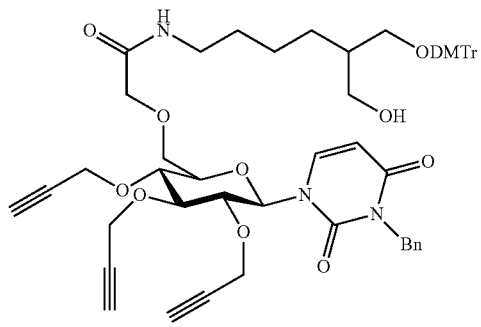

Compound 78

Synthesis of Compound 71: To a solution of Compound 9 (1.94 g, 4.38 mmol) in anhydrous DMF (20 mL) was added DBU (732 mg, 4.81 mmol, 1.1 eq) and benzyl bromide (822 mg, 4.81 mmol, 1.1 eq). The reaction mixture was stirred for 16 hours at room temperature. TLC indicated completion of the reaction. The mixture was diluted with ethyl acetate and water. The organic layer was washed with brine, dried over $Na_2SO_4$, filtered, and concentrated. The residue was purified by silica gel column chromatography (eluting with 0-60% ethyl acetate/hexane) to provide Compound 71 (2.15 g, 92%) as a white foam. MS: found: $[M+H]^+$=533.3; calc: $[M+H]^+$=533.3.

Synthesis of Compound 72: To a solution of Compound 71 (2 g, 3.7 mmol) in MeOH (20 mL) was added ammonia in methanol (2 M, 11.2 mL, 22.5 mmol, 6 eq) at 0° C. The icebath was removed after 5 min, and the reaction was allowed to stir at room temperature overnight. HPLC indicated the reaction was complete. The reaction was concentrated and co-evaporated with anhydrous toluene (×2) and used directly without further purification. The residue was Compound 72 (1.3 g, 96%) and was a white foam. MS: found: $[M+NH_4]^+$=382.1; calc: $[M+NH_4]^+$=382.1.

Synthesis of Compound 73: To a solution of Compound 72 (1.3 g, 3.6 mmol) in anhydrous pyridine (10 mL) was added DMTrCl (1.6 g, 4.7 mmol, 1.3 eq, 4,4'-Dimethoxytriphenylmethyl chloride) at 0° C. The reaction was allowed to stir at room temperature overnight. HPLC indicated the reaction was complete. The reaction was quenched with MeOH and concentrated in vacuo. The residue was diluted with ethyl acetate, washed with aqueous saturated sodium bicarbonate. The organic layer was then washed with brine, dried over anhydrous sodium sulfate, filtered, and concentrated. The crude material was purified on a silica gel column (50-100% ethyl acetate/hexane, 1% triethylamine additive in ethyl acetate and hexane, then 0-5% MeOH/DCM, 1% triethylamine in MeOH and DCM). The desired product was pooled and concentrated. The material contains triethylamine salt. The material was diluted with ethyl acetate and washed with saturated aqueous sodium bicarbonate. The organic layer was washed with brine and dried over anhydrous sodium sulfate, filtered and concentrated to provide Compound 73 (2.23 g, 3.34 mmol, 92%) as a white foam. MS: found: $[M+NH_4]^+$=684.7; calc: $[M+NH_4]^+$=684.7.

Synthesis of Compound 74: To a solution of Compound 73 (2.12 g, 3.18 mmol) in anhydrous DMF (10 mL) was propargyl bromide (80% in toluene, ~9.2 mol/L, 2.28 mL, 6.6 eq). The resulting reaction mixture was cooled to 0° C. and NaH (60% in mineral oil, 420 mg, 3.3 eq) was added in one portion. After stirring at 0° C. for a few minutes, the reaction was warmed to room temperature and stirred for 4 hours, at which point HPLC indicated the reaction was complete. The reaction was quenched with ice at 0° C. and diluted with ethyl acetate. The organic layer was washed with brine, dried over anhydrous sodium sulfate, filtered, and concentrated. The crude material was purified on a silica gel column (0-50% ethyl acetate/hexane, 1% triethylamine in hexane) to give Compound 74 (1.79 g, 2.29 mmol, 72%) as a white foam. MS: found $[M+NH_4]^+$=798.6; calc: $[M+NH_4]^+$=798.6.

Synthesis of Compound 75: To a solution of Compound 74 (1.79 g, 2.29 mmol) in DCM (10 mL) was added triethylsilane (0.88 g, 7.56 mmol, 3.3 eq) and the mixture was cooled to 0° C. TFA (0.57 g, 5.04 mmol, 2.2 eq) was added slowly in one portion. The reaction was stirred at room temperature for 1 hour. HPLC indicated the reaction was complete. The reaction mixture was concentrated and the crude material was purified on a silica gel column (0-100% ethyl acetate/hexane) to provide Compound 75 (0.956 g, 2.0 mmol, 87%) as a white foam. MS: found: $[M+NH_4]^+$=496.4; calc: $[M+NH_4]^+$=496.4.

Synthesis of Compound 76: To a solution of Compound 75 (0.956 g, 2.0 mmol) in anhydrous DMF (10 mL) was added tert-butyl bromoacetate (2.58 g, 13.2 mmol, 6.6 eq) in three portions at room temperature. The mixture was then cooled to 0° C. Potassium tert-butoxide (0.741 g, 6.6 mmol, 3.3 eq) was added in three portions. The reaction was stirred at the same temperature for a total of 3 hours. The reaction was allowed to slowly warm to room temperature and stir for an additional hour. The reaction was cooled to 0° C., quenched with DI water, and neutralized with citric acid to pH=4. The reaction mixture was extracted with ethyl acetate. The organic layer was washed with DI water, brine, dried over anhydrous sodium sulfate, filtered, and concentrated. The crude material was purified on a silica gel column (0-50%-100% ethyl acetate/hexane) to provide Compound 76 (0.92 g, 1.55 mmol, 77%) as a white foam. MS: found: $[M+NH_4]^+$=610.3; calc: $[M+NH_4]^+$=610.3.

Synthesis of Compound 77: To a solution of Compound 76 (0.92 g, 1.55 mmol) in DCM (7 mL) was added triethylsilane (0.541 g, 4.65 mmol, 3 eq), followed by TFA (7.45 g, 5 mL, 65 mmol, 42 eq) adding slowly in 5 portions. The reaction was stirred at room temperature for 1 hour. HPLC indicated the reaction was complete. The reaction mixture was concentrated. The crude material was purified on a silica gel column (0-10% MeOH/DCM) to provide Compound 77 (0.81 g, 1.51 mmol, 97%) as a white foam. MS: found: $[M-H]^-$=535.3; calc: $[M-H]^-$=535.3.

Synthesis of Compound 78: To a solution of Compound 77 (0.81 g, 1.51 mmol) in anhydrous DMF (3 mL) was added HATU (0.662 g, 1.74 mmol, 1.05 eq) and DIPEA (0.205 g, 1.74 mmol, 1.05 eq). The mixture was allowed to stir at the same temperature for 10 min under argon atmosphere, 6-amino-2-((bis(4-methoxyphenyl)(phenyl)methoxy)methyl)hexan-1-ol (Compound 40) (0.781 g, 1.74 mmol, 1.05 eq) was added in 5 portions followed by DIPEA (0.205 g, 1.74 mmol, 1.05 eq). The reaction was allowed to stir at room temperature overnight. HPLC indicated the reaction was complete. The reaction mixture was diluted with ethyl acetate and water. After separation, the organic layer was washed with brine, dried over anhydrous sodium sulfate, filtered and concentrated. The crude material was purified on a silica gel flash column (0-10% MeOH/DCM) to give Compound 78 (1.16 g, 1.2 mmol, 79%) as a white foam. MS: found: $[M+NH_4]^+$=985.7; calc: $[M+NH_4]^+$=985.7.

Scheme 17

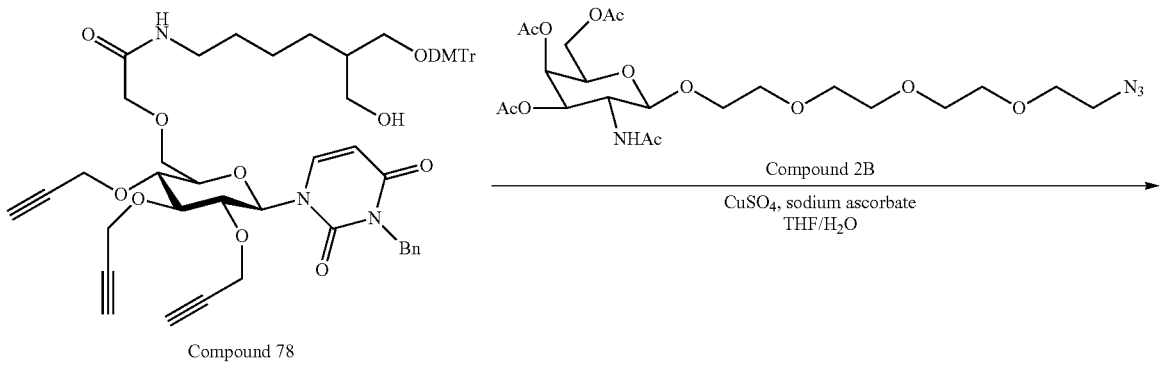

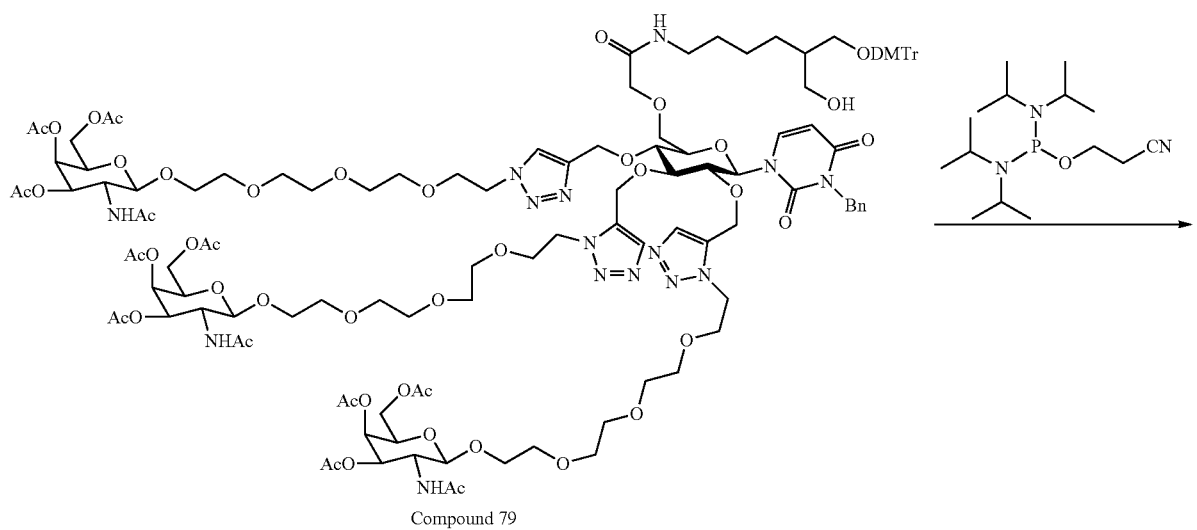

-continued

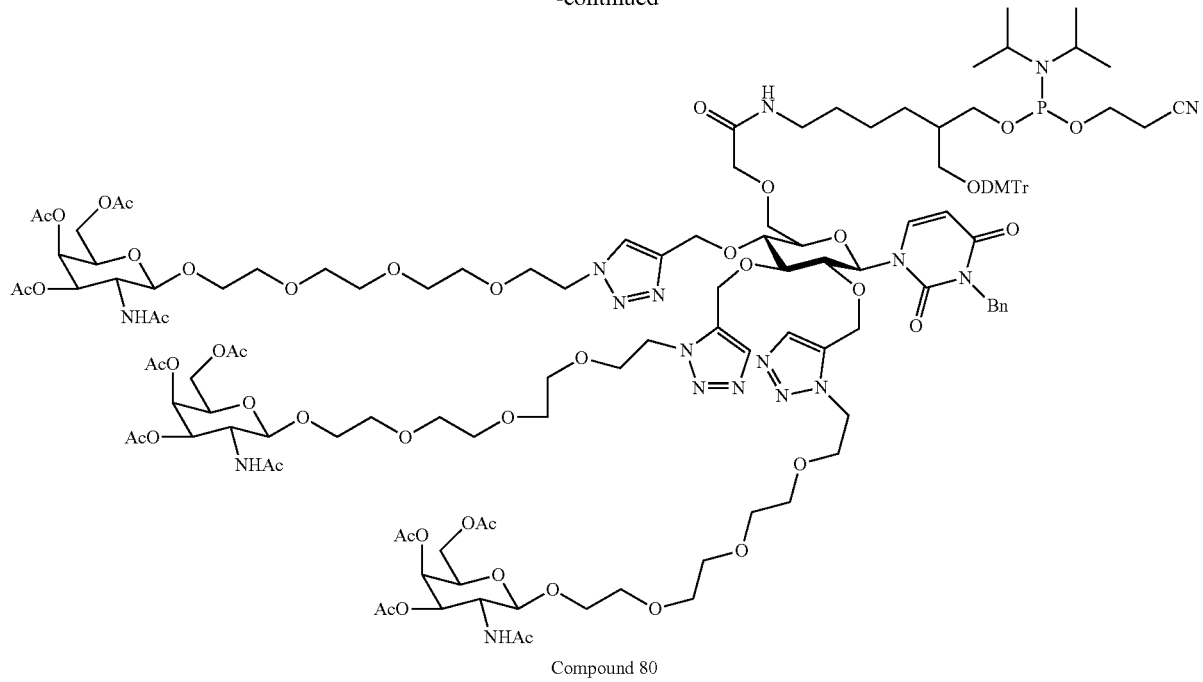

Compound 80

Synthesis of Compound 79: To a solution of Compound 78 (1.16 g, 1.2 mmol) in THF (10 mL) was added GalNac azide (Compound 2B)(2.2 g, 3.96 mmol, 3.3 eq), the mixture was cooled to 0° C., L-Asc sodium salt (0.83 g, 4.2 mmol, 3.5 eq) freshly made solution in DI water (5 mL) was added followed by freshly made solution of CuSO$_4$·5H$_2$O (0.90 g, 3.6 mmol, 3 eq) in DI water (5 mL). The reaction mixture was allowed to stir at 0° C. for 10 min then the reaction mixture was stirred at room temperature for 1 hour. HPLC indicated the reaction was complete. The reaction mixture was then cooled to 0° C. and quenched with saturated sodium bicarbonate solution and extracted with DCM×3. The combined organic layers were washed with brine, dried over anhydrous sodium sulfate, filtered and concentrated. The crude material was purified on a silica gel column (0-15% MeOH/DCM, 1% TEA in DCM) to provide Compound 79 (1.97 g, 0.75 mmol, 62%) as a white foam. MS: found: $[M+2NH_4/2]^{2+}=1324.2$; calc: $[M+2NH_4/2]^{2+}=1324.2$.

Synthesis of Compound 80: To a solution of Compound 79 (0.86 g, 0.33 mmol) in anhydrous DCM (20 mL) was added diisopropylammonium tetrazolide (11 mg, 0.066 mmol) and Bis(diisopropylamino)(2-cyanoethoxy)phosphine (258 mg, 0.856 mmol, 2.6 eq) in 2 portions under argon. The reaction mixture was stirred at room temperature overnight. HPLC indicated completion of the reaction. The mixture was diluted with saturated NaHCO$_3$/DCM (10 mL/10 mL). The aqueous layer was extracted with DCM (10 mL×2). The combined organic layer was washed with saturated NaHCO$_3$ (10 mL×2), dried over Na$_2$SO$_4$, filtered and concentrated. The residue was dissolved in CH$_3$CN (35 mL) and washed with hexane (10 mL×2). The CH$_3$CN phase was concentrated and the residue was purified by column chromatography (eluting with 0-5% MeOH in DCM, 1% triethylamine in MeOH and DCM) to provide the TriGalNAc amidite with triethylamine salt. The white foam was diluted with DCM and washed with water, saturated NaHCO$_3$, brine and dried over anhy. sodium sulfate, filtered and concentrated, then further dried on a lyophilizer to provide the desired amidite 11 (608 mg, 66%) as a white foam. MS: found: $[M+2H/2]^{2+}=1407.7$; calc: $[M+2H/2]^{2+}=1407.7$. $^{31}$PNMR (mixture of diastereomers, CDCl$_3$): δ 146.99, 146.78 ppm.

Example 14. General Procedure for the Preparation of Trivalent GalNAc Analog

Scheme 18.

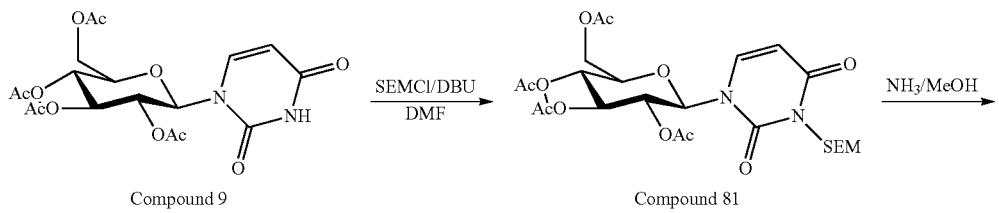

119    120
-continued
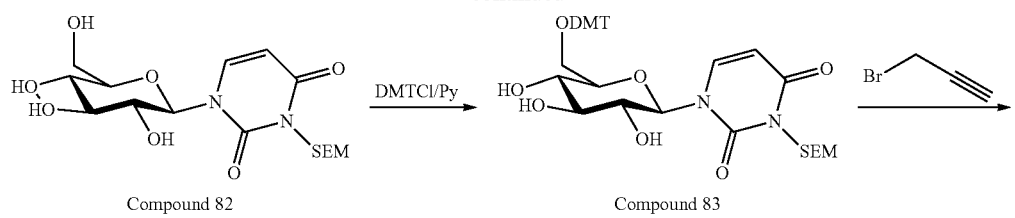
Compound 82 → Compound 83
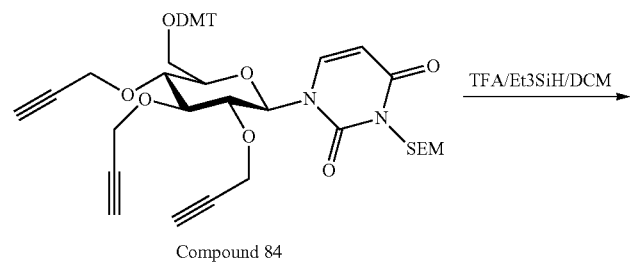
Compound 84
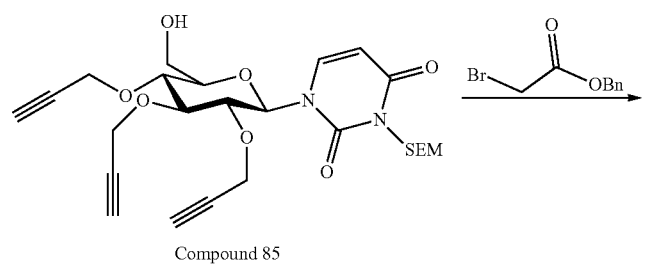
Compound 85
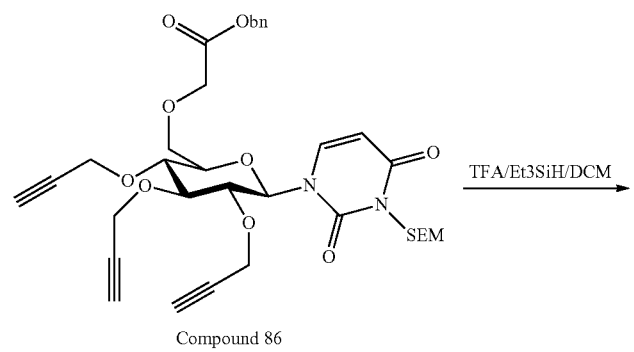
Compound 86
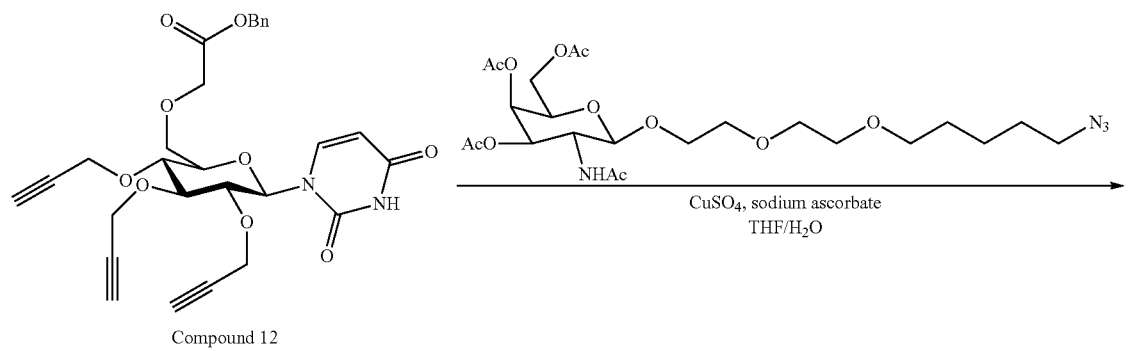
Compound 12

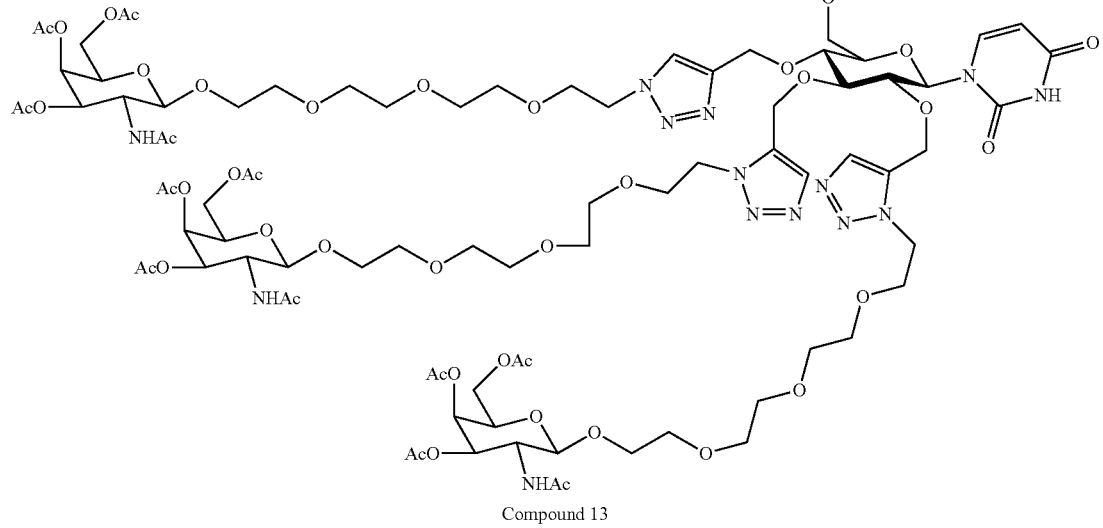

Compound 13

Synthesis of Compound 81: To a solution of Compound 9 (10.0 g, 22.6 mmol) in anhydrous DMF (50 mL) was added 2-(Trimethylsilyl)ethoxymethyl chloride (SEMCl) (4.35 g, 4.62 mL, 24.8 mmol, 1.1 eq). DBU (3.78 g, 3.7 mL, 24.8 mmol, 1.1 eq) was then added slowly and the mixture was stirred at room temperature for 3 hours. TLC indicated completion of the reaction. The mixture was concentrated in vacuo. The resulting crude material was diluted with ethyl acetate and water. After separation, the organic layer was washed with brine, dried over anhydrous sodium sulfate, filtered, and concentrated. The crude material was purified on a silica gel column (0-100% ethyl acetate/hexane) to give Compound 81 (10.0 g, 17.4 mmol, 77%) as a white foam. MS: found: $[M+H]^+$=573.4; calc: $[M+H]^+$=573.4.

Synthesis of Compound 82: To a solution of Compound 81 (10.0 g, 17.4 mmol) in MeOH (20 mL) was added ammonia in methanol (2 M, 48 mL, 96 mmol, 5.5 eq) at 0° C. After 5 min, the reaction was allowed to warm to room temperature and was stirred overnight. HPLC indicated the reaction was complete. The reaction was concentrated and co-evaporated with anhydrous toluene two times and used directly without further purification. The residue was Compound 82 (7.0 g, 100%) and was a white foam. MS: found: $[M+AcOH-H]^-$=463.3; calc: $[M+HOAc-H]^-$=463.2.

Synthesis of Compound 83: To a solution of Compound 82 (7.0 g, 17.3 mmol) in anhydrous pyridine (50 mL) was added DMTrCl (7.62 g, 22.5 mmol, 1.3 eq, 4,4'-Dimethoxytriphenylmethyl chloride) at 0° C. The reaction was allowed to stir at room temperature overnight. The reaction was quenched with MeOH and concentrated in vacuo. The residue was diluted with ethyl acetate and washed with saturated sodium bicarbonate solution. The organic layer was then washed with brine, dried over anhydrous sodium sulfate, filtered and concentrated. The crude material was purified on a silica gel column (50-100% ethyl acetate/hexane, 1% triethylamine additive in hexane) to provide Compound 83 (10.22 g, 14.5 mmol, 83%) as a white foam. MS: found: $[M+NH_4]^+$=724.6; calc: $[M+NH_4]^+$=724.6.

Synthesis of Compound 84: To a solution of Compound 83 (1.77 g, 2.5 mmol) in anhydrous DMF (10 mL) was added propargyl bromide (80% in toluene, ~9.2 mol/L, 1.86 mL, 17.7 mmol, 7.1 eq). The resulting reaction mixture was cooled to 0° C. and NaH (60% in mineral oil, 350 mg, 3.55 eq) was added in one portion. After stirring at 0° C. for a few minutes, the reaction was warmed to room temperature and stirred for 16 hours. HPLC indicated the reaction was complete. The reaction was quenched with ice at 0° C. and diluted with ethyl acetate. The organic layer was washed with brine, dried over anhydrous sodium sulfate, filtered and concentrated. The crude material was purified on a silica gel column (0-50% ethyl acetate/hexane, 0.5% triethylamine in hexane) to give Compound 84 (1.59 g, 1.93 mmol, 77%) as an off-white foam. Direct mass analysis did not provide the desired mass. However, Compound 84 (89 mg) was treated with TFA in DCM, and after complete removal of DMT and SEM, gave the desired mass. MS: found $[M+NH_4]^+$=406.4; calc: $[M+NH_4]^+$=406.4.

Synthesis of Compound 85: To a solution of Compound 84 (1.5 g, 1.83 mmol) in DCM (50 mL) was added triethylsilane (0.234 g, 2.01 mmol, 1.1 eq). The reaction mixture was cooled to 0° C. and TFA (0.918 g, 0.616 mL, 8.06 mmol, 4.4 eq) was added one portion. The reaction was stirred at 0° C. for 5 hours. HPLC indicated the reaction was complete. The reaction mixture was quenched with saturated sodium bicarbonate and extracted with DCM (3x). The combined DCM layers were washed with brine, dried over anhydrous sodium sulfate, filtered and concentrated. The crude material was purified on a silica gel column (0-100% ethyl acetate/hexane) to provide Compound 85 (0.8 g, 1.54 mmol, 84%) as a white foam. MS: found: $[M+H]^+$=519.5; calc: $[M+H]^+$=519.5.

Synthesis of Compound 86: To a solution of Compound 85 (0.85 g, 1.64 mmol) in anhydrous DMF (10 mL) was added benzyl bromoacetate (1.66 g, 7.22 mmol, 4.4 eq) in 2 portions at room temperature. The mixture was then cooled to 0° C. Potassium tert-butoxide (0.4 g, 3.6 mmol, 2.2 eq) was added in 2 portions. The reaction was stirred at 0° C. for a total of 2 hrs, and the reaction was allowed to slowly warm to room temperature and stirred overnight. The reaction was cooled to 0° C., quenched with DI water, and neutralized with citric acid to pH=4. The reaction mixture was extracted with ethyl acetate. The organic layer was washed with DI water, brine, dried over anhydrous sodium sulfate, filtered and concentrated. The crude material was purified on a silica gel column (0-50% ethyl acetate/hexane) to provide Compound 86 (0.43 g, 0.645 mmol, 39%) as a white foam. MS: found: $[M+NH_4]^+$=684.7; calc: $[M+NH_4]^+$=684.7.

Synthesis of Compound 12: To a solution of Compound 86 (0.43 g, 0.64 mmol) in DCM (10 mL) was added triethylsilane (0.245 g, 2.11 mmol, 3.3 eq). The reaction mixture was cooled to 0° C. and TFA (0.73 g, 0.49 mL, 6.4 mmol, 10 eq) was added slowly. The reaction was stirred at 0° C. for 10 min before the ice bath was removed. The reaction was allowed to stir at room temperature for 16 hrs. HPLC indicated the reaction was complete. The reaction mixture was concentrated, and the crude material was purified on a silica gel column (0-30% ethyl acetate/hexane) to provide Compound 12 (0.2 g, 0.372 mmol, 58%) as a white foam. MS: found: $[M-H]^-$=535.4; calc: $[M-H]^-$=535.4.

Synthesis of Compound 13: To a solution of Compound 12 (0.2 g, 0.32 mmol) in THF (3 mL) was added GalNac azide (Compound 2B)(0.574 g, 1.05 mmol, 3.3 eq). The mixture was cooled to 0° C., and L-Asc sodium salt (0.222 g, 1.12 mmol, 3.5 eq) freshly made in DI water (1 mL) was added followed by a freshly made solution of $CuSO_4 \cdot 5H_2O$ (0.24 g, 0.96 mmol, 3 eq) in DI water (1 mL). The reaction mixture was allowed to stir at room temperature for 16 hrs. HPLC indicated the reaction was complete. The reaction mixture was then cooled to 0° C., quenched with saturated aqueous sodium bicarbonate, and extracted with DCM×3. The combined organic layers were washed with brine, dried over anhydrous sodium sulfate, filtered, and concentrated. The crude material was purified on a silica gel column (0-10% MeOH/DCM) to provide Compound 13 (0.22 g, 0.1 mmol, 32%) as a white foam. MS: found: $[M/2+NH_4]^+$=1109.2; calc: $[M/2+NH_4]^+$=1109.2.

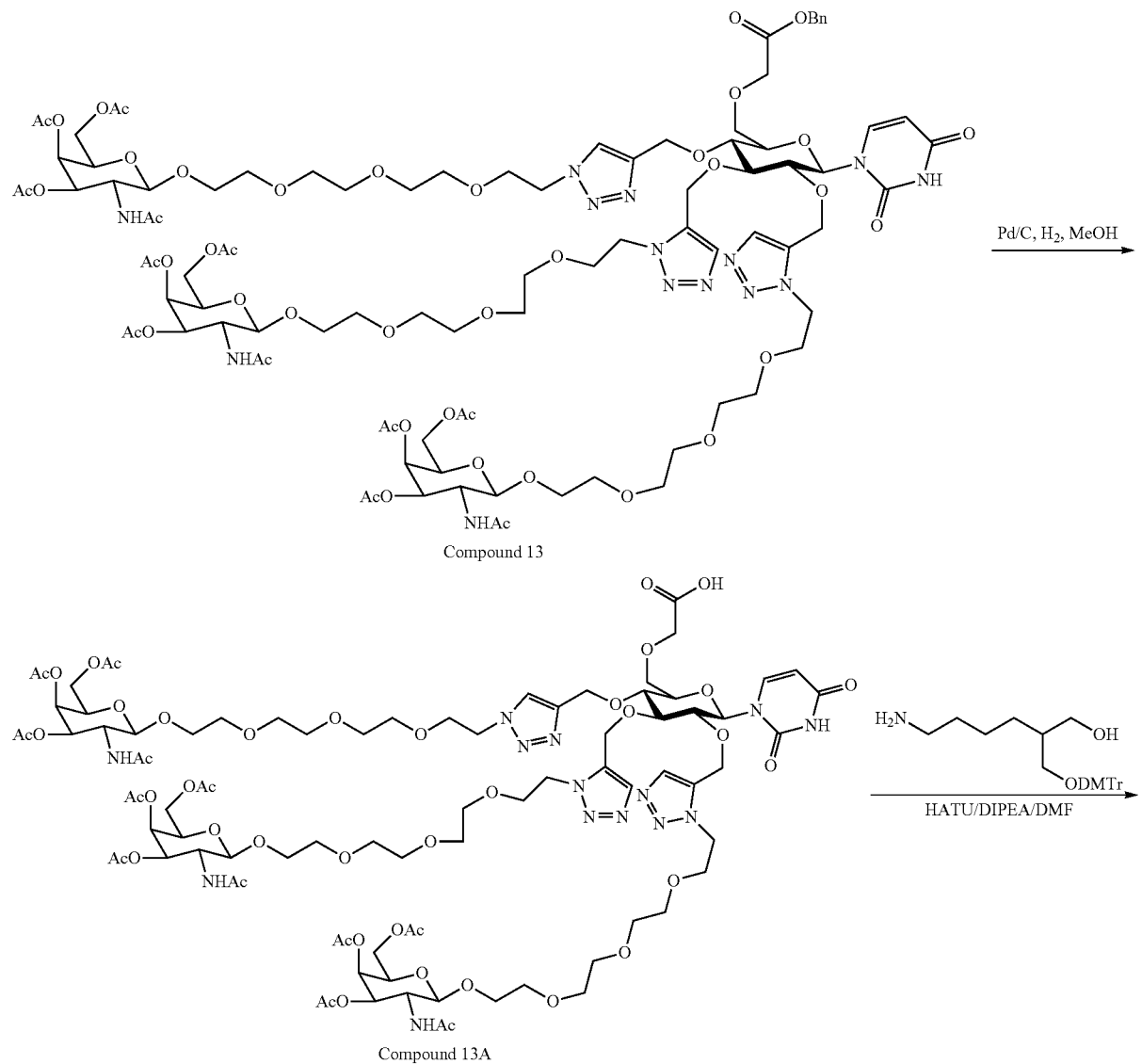

Scheme 19

-continued
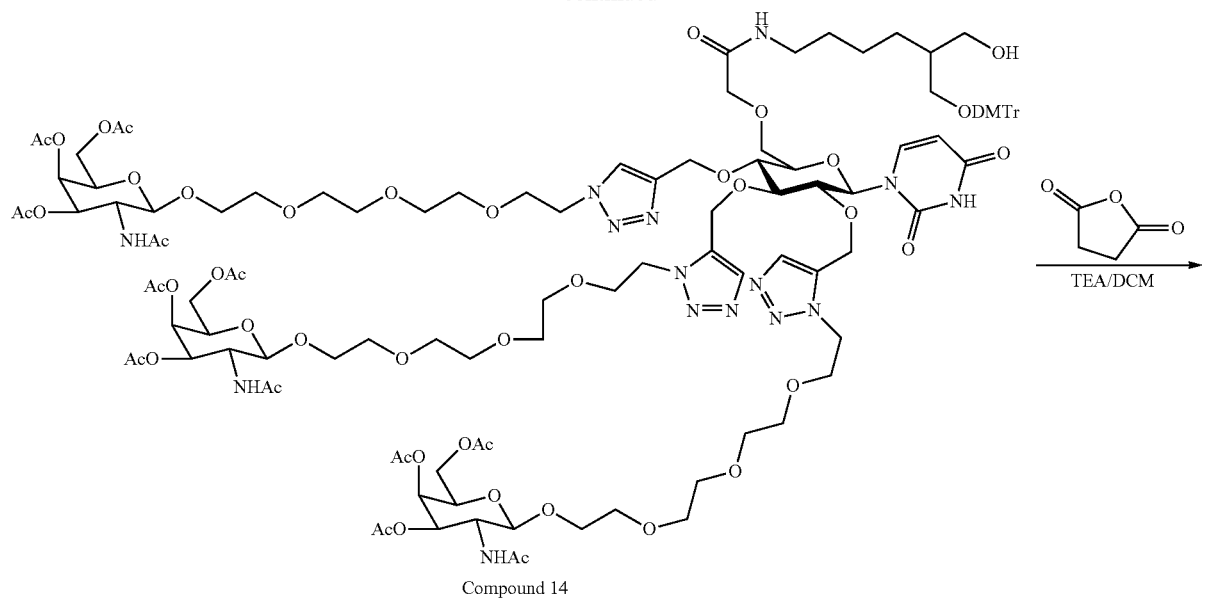
Compound 14
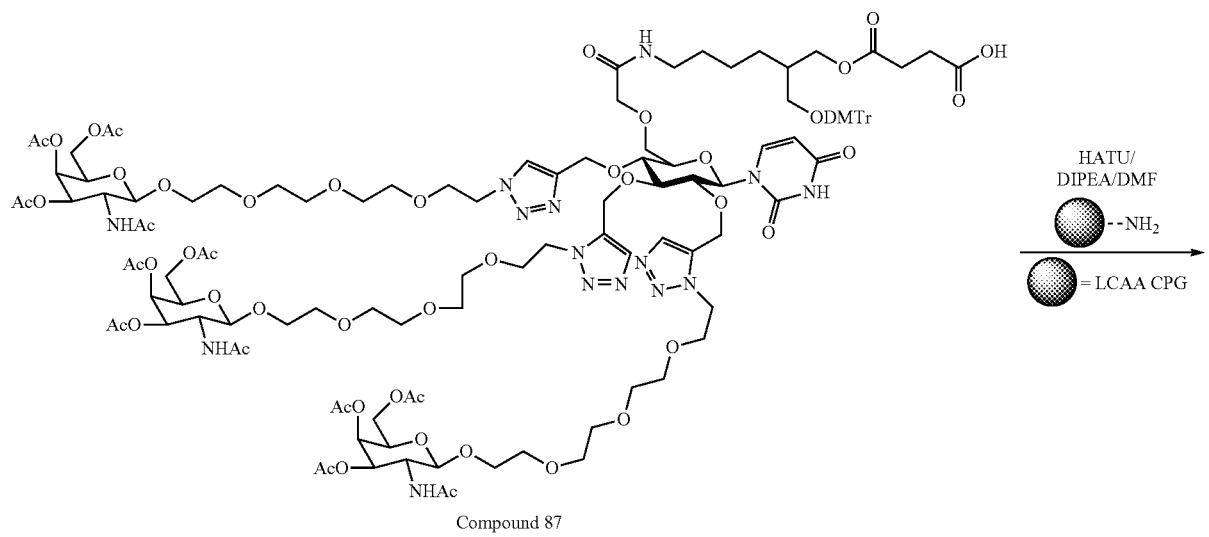
Compound 87

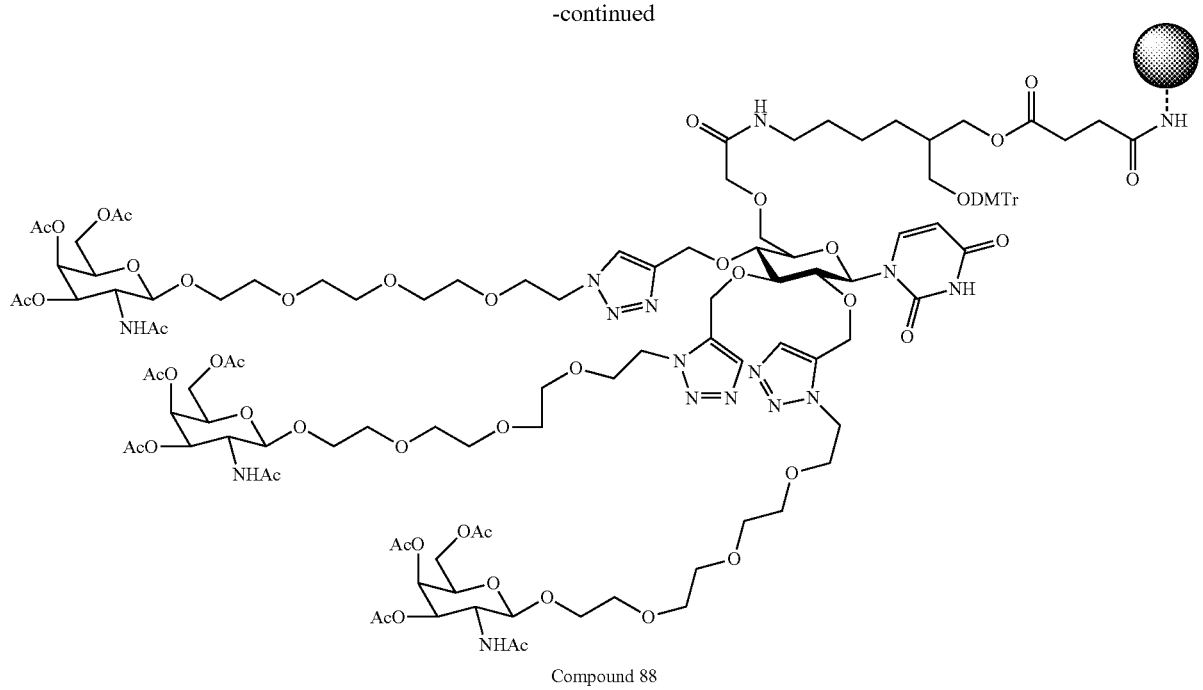

Compound 88

Synthesis of Compound 13A: To a solution of Compound 13 (0.22 g, 0.1 mmol) in MeOH (10 mL) was added wet Pd/C (0.22 g). The mixture was evacuated and a hydrogen balloon was applied while stirring at room temperature for 3 days. HPLC indicated the reaction was complete. The reaction mixture was filtered through a Celite pad and rinsed with MeOH. The filtrate was concentrated to provide Compound 89 (0.205 g, 0.098 mmol, 98%) as a white solid. MS: found: [M−2H/2]⁻=1045.1; calc: [M−2H/2]⁻=1045.1. Compound 13A was used in the next step without further purification.

Synthesis of Compound 14: To a solution of Compound 13A (0.205 g, 0.098 mmol) in anhydrous DMF (2 mL) was added HATU (0.039 g, 0.103 mmol, 1.05 eq) and diisopropylethyl amine (0.0133 g, 0.103 mmol, 1.05 eq). The mixture was allowed to stir at the same temperature for 10 min under argon atmosphere, 6-amino-2-((bis(4-methoxyphenyl)(phenyl)methoxy)methyl)hexan-1-ol (Compound 40) (0.046 g, 0.103 mmol, 1.05 eq) was added, followed by DIPEA (0.0133 g, 0.103 mmol, 1.05 eq). The reaction was allowed to stir at room temperature overnight. HPLC indicated the reaction was complete. The reaction mixture was diluted with ethyl acetate and water. After separation, the organic layer was washed with brine, dried over anhydrous sodium sulfate, filtered and concentrated. The crude material was purified on a silica gel flash column (0-10% MeOH/DCM, 0.5% triethylamine/DCM) and fractions that contains desired product were repurified on a C18 flash column (0-90% ACN/H₂O) to give Compound 14 (0.036 g, 0.014 mmol, 14%) as a white foam. MS: found: [M+AcOH—H/2]⁻=1291.2; calc: [M+AcOH—H/2]⁻=1291.2.

Synthesis of Compound 87: To a solution of Compound 14 (0.036 g, 0.014 mmol) in anhydrous DCM (2 mL) was added succinic anhydride (0.043 g, 0.043 mmol, 3 eq) in one portion, followed by triethylamine (6 μL, 0.043 mmol, 3 eq). The reaction was stirred at room temperature for 3 hours. HPLC indicated the reaction was complete. The reaction was concentrated to a semi-solid and purified on a C18 flash column (0-90% CH₃CN/H₂O) to give Compound 87 (0.024 g, 0.0091 mmol, 65%) as a white foam. MS: found: [M−2H/2]²⁻=1311.2; calc: [M−2H/2]²⁻=1311.2.

Synthesis of TriGalNAc CPG1 (Compound 88): To a solution of TriGalNAc succinate 87 (24 mg, 0.0091 mmol) in anhydrous ACN (2 mL) was added HATU (3.5 mg, 0.0091 mmol, 1 eq) and DIPEA (1.8 mg, 0.14 mmol, 1.5 eq). The mixture was stirred at room temperature for 10 min. Pretreated LCAA CPG 500Å (0.12 g, loading: 75 μmol/g) was added followed by DIPEA (1.8 mg, 0.14 mmol, 1.5 eq). The resulting mixture was slowly agitated at 25° C. for 3 hours. The mixture was then filtered, and the CPG was washed with acetonitrile (1 mL×3), THF (1 mL×3), and MTBE (1 mL×2) successively. The CPG was dried under reduced pressure overnight.

To the CPG was added a mixture of Ac₂O (0.1 mL) and pyridine (0.1 mL) in anhydrous THF (0.8 mL). The resulting mixture was slowly agitated at 25° C. for 30 min. The mixture was then filtered, and this CPG was washed with THF (1 mL×1), 10% pyridine in MeOH (1 mL×2), MeOH (1 mL×2), acetonitrile (1 mL×2) and MTBE (1 mL×1) successively. The capped CPG was dried under reduced pressure for 48 hrs to give the TriGalNAc CPG1 500A (Compound 88)(0.13 g, Loading was determined by standard DMTr assay by UV-Vis (498 nm) to be 47 μmol/g). Ninhydrin test: negative.

Example 15: Use of GalNAc-conjugated Solid Supports in Oligonucleotide Synthesis To demonstrate the usage of novel GalNAc-conjugated solid supports in oligonucleotide synthesis, a sequence was designed for trails: 5'-TTTTTTTTTT (SEQ ID NO:1)-Y-3', where Y represents GalNAc-conjugated solid supports. Two compounds were generated: compound T10-Y1 and compound T10-Y2, wherein Y1 is Compound 69 and wherein Y2 is Compound 88.

Oligonucleotides T10-Y1 and T10-Y2 were synthesized by solid phase phosphoramidite method. A novel DMT-GalNAc conjugated solid support (Y) was packed in an empty column and put into the MerMade 6 synthesizer. The synthetic scale was 0.5-1 µmol. The oligonucleotide synthesis cycle included the following steps: (1) detritylation with 3% trichloroacetic acid in dichloromethane for 45 seconds two times, followed by acetonitrile washing; (2) coupling with 0.1 M DMT-dT-CE-Phosphoramidite (5'-O-(4,4'-Dimethoxytrityl)-thymidine-3'-cyanoethyl Phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 second, followed by acetonitrile washing; and (4) capping with a mixture of acetic anhydride, pyridine, and THE for 45 second, followed by acetonitrile washing. Steps (1)-(4) were repeated 10 times for synthesizing a T10 elongated from the GalNAc conjugated solid support and finished by the final detritylation with acetonitrile washing.

After synthesis, the oligonucleotide-bounded solid supports were treated with a 1:1 mixture of aqueous ammonia hydroxide and methylamine at 55° C. for 2 hours for cleavage and deprotection. Upon completion, the liquid phase was collected, and heat dried in a vacuum concentrator. The dried residue was dissolved in water and analyzed by reverse-phase HPLC (Agilent 1260) and LC-MS (Applied Biosystems 4000 Q-Trap). The HPLC gradient was 5-20% D in 20 minutes, with Buffer A: 50 mM triethylammonium acetate in water and Buffer D: ACN. The retention time (RT), mass calculated, mass observed, and full-length product purity (FLP) for each sequence were listed below.

TABLE 1

Oligo functional test results for novel triGalNAc-click linker solid support.

| Compound | Formula Weight of Y | Calculated Oligo Mass | FLP Retention Time (min) | FLP Purity (%) | Observed Mass |
|---|---|---|---|---|---|
| T10-(Y1) | 1950.96 | 4931.96 | 21.116 | 47.67 | 4932.5 |
| T10-(Y2) | 1904.88 | 4885.88 | 13.331 | 74.85 | 4886.5 |

Example 16: Use of GalNAc-Phosphoramidite in Oligonucleotide Synthesis

To demonstrate the usage of novel click-linker designs for triGalNAc-conjugated phosphoramidites in oligonucleotide synthesis, two sequences were designed for trials. An oligonucleotide sequence (5'-TTTTTTTTTT-3'; SEQ ID. NO: 1), coupled with a triGalNac click linker conjugated phosphoramidite "X" was prepared to form 5'-X-TTTTTTTTTT-3'. In addition, an oligonucleotide sequence (5'-TTTTT-3') was first coupled with a triGalNac click linker conjugated phosphoramidite "X" and subsequently continued to add additional five T to form 5'-TTTTT-X-TTTTT-3'. Two oligonucleotide sequences were generated: Compound T10-X3 and Compound T5-X3-T5, wherein X3 is Compound 80.

Oligonucleotides (Compound T10-X3 and Compound T5-X3-T3) were synthesized by a solid-phase phosphoramidite method from a MerMade 6 synthesizer (LGC, Biosearch Technologies). A DMT-dT solid support was packed in an empty column and the column was placed into the synthesizer. The synthetic scale was 0.5-1 µmol. The oligonucleotide synthesis cycle included the following steps: (1) detritylation with 3% trichloroacetic acid in dichloromethane for 45 seconds two times, followed by acetonitrile washing; (2) coupling with 0.1 M DMT-dT-CE-Phosphoramidite (5'-O-(4,4'-dimethoxytrityl)-thymidine-3'-cyanoethyl Phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 seconds, followed by acetonitrile washing; and (4) capping with a mixture of acetic anhydride, pyridine, and THE for 45 seconds, followed by acetonitrile washing. Steps (1)-(4) were repeated for synthesizing each "T" elongated from the solid support. For the cycle to couple the novel triGalNAc click linker-conjugated phosphoramidites, it included the sample detritylation, coupling, oxidation, and capping step; while the coupling used a mixture of 0.12 M phosphoramidites in acetonitrile and 0.5 M activator for 10 minutes two times, followed by acetonitrile washing.

After synthesis, the oligonucleotide-bounded solid supports were treated with a 1:1 mixture of aqueous ammonia hydroxide and methylamine at 55° C. for 2 hours for cleavage and deprotection. Upon completion, the liquid phase was collected and heat dried in a vacuum concentrator. The dried residue was dissolved in water and analyzed by reverse-phase HPLC (Agilent 1260) and LC-MS (Applied Biosystems 4000 Q-Trap). The IPLC gradient was 5-20% D in 20 minutes, with Buffer A: 50 mM triethylammonium acetate in water and Buffer D: ACN. The retention time (RT), mass calculated, mass observed, and full-length product purity (FLP) for each sequence were listed below.

TABLE 2

Oligo functional test results for novel triGalNAc-click linker phosphoramdite

| Compound | Formula Weight of X | Calculated Oligo M.W. | FLP Retention Time (min) | FLP Purity (%) | Observed Mass |
|---|---|---|---|---|---|
| (X3)-T10 | 1995.01 | 4976.01 | 18.604 | 55.80 | 4977.2 |
| T5-(X3)-T5 | 1995.01 | 4976.01 | 18.398 | 23.10 | 4978.3 |

While the present application has been described with reference to the specific embodiments thereof, it should be understood by those skilled in the art that various changes may be made and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

What is claimed is:

1. A compound of Formula (I):

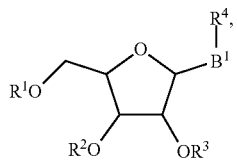

wherein:
each of $R^1$, $R^2$, and $R^3$ is independently $-L^{1a}$-Z-$L^2$-G, $-L^{1b}$-C(=O)$NR^A R^B$, or $-L^{1c}$-C(=O)$NR^5 R^6$;
each of $R^A$ and $R^B$ is independently hydrogen, optionally substituted $C_{1-6}$ alkyl, or $-L^3$-Z-$L^4$-G, and at least one of $R^A$ and $R^B$ is $-L^3$-Z-$L^4$-G;
$R^4$ is hydrogen, —Z-$L^5$-G, or $-L^{1c}$-C(=O)$NR^5 R^6$;
provided that one of $R^1$, $R^2$, $R^3$, and $R^4$ is $-L^{1c}$-C(=O)$NR^5 R^6$ and the others of $R^1$, $R^2$, $R^3$, and $R^4$ are not $-L^{1c}$-C(=O)$NR^5 R^6$;
each $R^5$ is independently

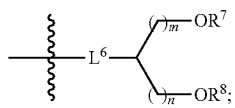

each of m and n is independently 0, 1, 2 or 3;
$R^6$ is H or $C_1$-$C_6$ alkyl;
$R^7$ is a hydroxy protecting group;
$R^8$ is hydrogen, a phosphoramidite moiety, —C(=O)$CH_2 CH_2 C$(=O)$R^{8A}$, or —P(O$R^{8B}$)$NR^{8C} R^{8D}$;
$R^{8A}$ is —OH, —O$R^9$ or —$NR^{10} R^{11}$;
each of $R^{8B}$, $R^{8C}$ and $R^{8D}$ is independently H, $C_{1-6}$ haloalkyl, or unsubstituted or substituted $C_{1-6}$ alkyl;
$R^9$ is unsubstituted or substituted $C_{1-6}$ alkyl, or a hydroxy protecting group;
each of $R^{10}$ and $R^{11}$ is independently H, unsubstituted or substituted $C_{1-6}$ alkyl, or an amino protecting group;
$L^6$ is $C_{1-10}$ alkylene, or 2 to 15 membered heteroalkylene where one or more carbon atoms are replaced with C(=O), S, O or N;
each of $L^{1a}$, $L^{1b}$, and $L^{1c}$ is independently $C_{1-10}$ alkylene, —CH=CH—, —$CH_2 CH$=CH—, or 2 to 10 membered heteroalkylene where one to three carbon atoms are replaced with C(=O), O, S or N;
$L^3$ is $C_{1-10}$ alkylene;
each Z is a triazole ring, or a bi-, tri-, or tetracyclic ring system having a fused triazole ring;
each of $L^2$, $L^4$, and $L^5$ is independently $C_{1-10}$ alkylene, or 2 to 15 membered heteroalkylene wherein one to five carbon atoms are replaced with C(=O), O, S or N; or $C_1$-$C_{10}$ alkylene or 2 to 15 membered heteroalkylene each independently interrupted by a ring or ring system selected from the group consisting of $C_6$-$C_{10}$ arylene, $C_3$-$C_{10}$ cycloalkylene, five to ten membered heteroarylene, and three to ten membered heterocyclylene;

$B^1$ is

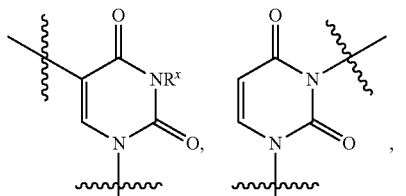

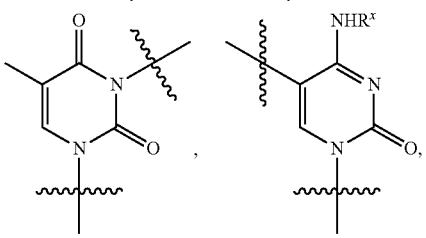

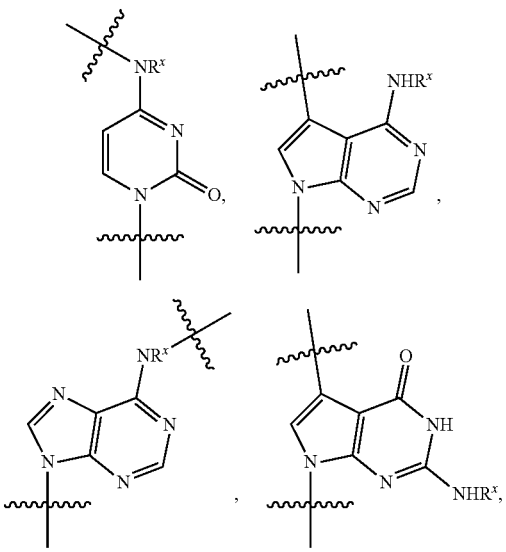

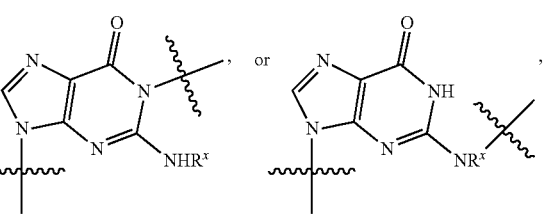

is hydrogen or an amino protecting group, or the hydrogen in —$NHR^x$ is absent and $R^x$ is a divalent amino protecting group;

G is

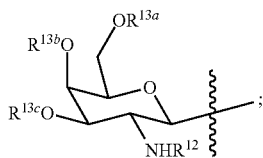

$R^{12}$ is —C(=O)$C_{1-6}$ alkyl, —C(=O)$C_{1-6}$ haloalkyl, or —C(=O)phenyl; and each of $R^{13a}$, $R^{13b}$ and $R^{13c}$ is independently hydrogen, benzyl (Bn), or —C(=O)$R^{13A}$, wherein $R^{13A}$ is $C_{1-6}$ alkyl, $C_{1-6}$ haloalkyl, or optionally substituted phenyl;

provided that the compound has three or more G groups.

2. The compound of claim 1, wherein each of $R^1$, $R^2$ and $R^3$ is independently -$L^{1a}$-Z-$L^2$-G, and $R^4$ is -$L^{1c}$-C(=O)NR$^5$R$^6$.

3. The compound of claim 1, wherein $R^1$ is -$L^{1b}$-C(=O)NR$^A$R$^B$, $R^2$ is -$L^{1c}$-C(=O)NR$^5$R$^6$, $R^3$ is -$L^{1a}$-Z-$L^2$-G, and $R^4$ is H.

4. The compound of claim 1, wherein each of $R^1$ and $R^3$ is independently -$L^{1a}$-Z-$L^2$-G, $R^2$ is -$L^{1c}$-C(=O)NR$^5$R$^6$, and $R^4$ is —Z-$L^5$-G.

5. The compound of claim 1, wherein each Z is independently

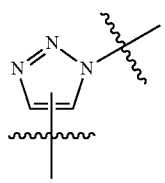

or

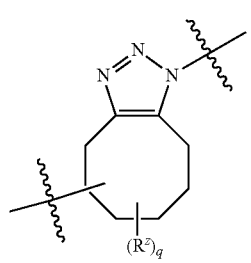

q is an integer from 0 to 6; each $R^z$ is independently halo or $C_{1-6}$ haloalkyl, or any two adjacent $R^z$ taken together with the atoms to which they are attached form an optionally substituted $C_{6-10}$ aryl, optionally substituted 5-10 membered heteroaryl, optionally substituted $C_{3-7}$ cycloalkyl, or optionally substituted 3 to 10 membered heterocyclyl.

6. The compound of claim 1, wherein the compound of Formula (I) has the Formula (Ia) or (Ia'):

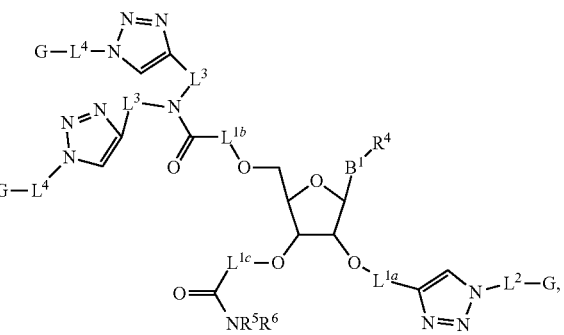

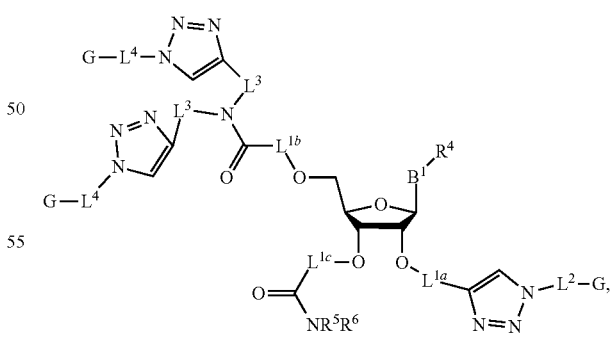

$R^4$ is H.

7. The compound of claim 1, wherein the compound of Formula (I) has the Formula (Ib) or (Ib'):

(Ib)

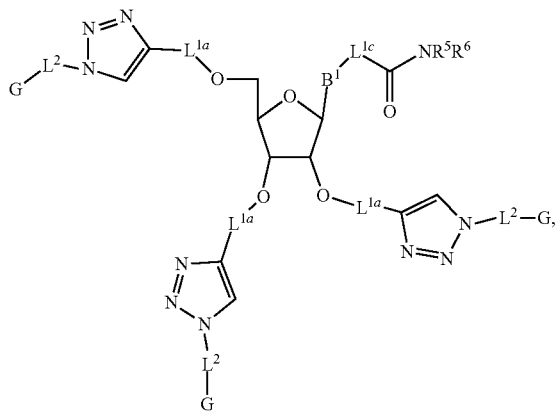

(Ib')

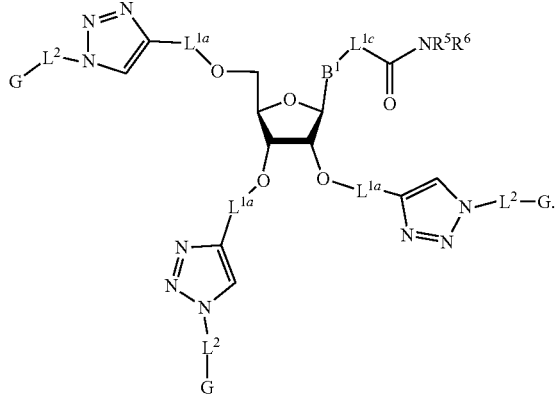

8. The compound of claim 1, wherein the compound of Formula (I) has the Formula (Ic) or (Ic'):

(Ic)

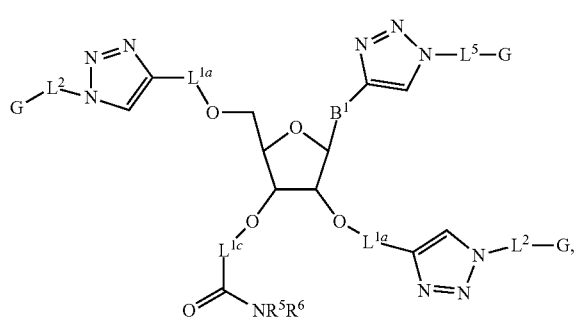

(Ic')

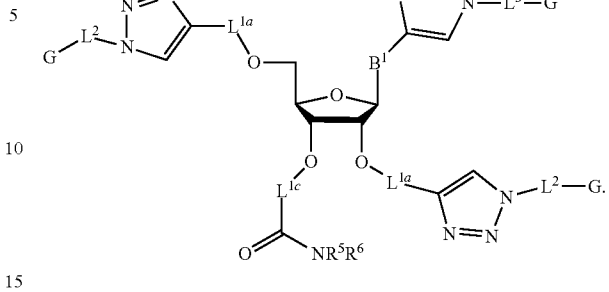

9. The compound of claim 1, wherein each of $L^2$, $L^4$ and $L^5$ is independently —(CH$_2$CH$_2$O)$_j$—, wherein j is 2, 3, 4, or 5.

10. The compound of claim 1, wherein each of $R^{13a}$, $R^{13b}$ and $R^{13c}$ is —C(=O)CH$_3$.

11. The compound of claim 1, wherein $R^{12}$ is —C(=O)CH$_3$ or —C(=O)CF$_3$.

12. The compound of claim 1, wherein $L^6$ is a $C_{1-6}$ alkylene.

13. The compound of claim 1, wherein m is 0 and n is 1, or m is 1 and n is 0.

14. The compound of claim 1, wherein both m and n are 0, or both m and n are 1.

15. The compound of claim 1, wherein $R^7$ is a trityl type of hydroxy protecting group selected from (4-methoxyphenyl)diphenylmethyl, bis(4-methoxyphenyl)phenylmethyl (DMTr), tris(4-methoxyphenyl)methyl, 9-phenylxanthen-9-yl, or 9-(4-methoxyphenyl)xanthen-9-yl.

16. The compound of claim 1, wherein $R^8$ is —C(=O)CH$_2$CH$_2$C(=O)OH.

17. The compound of claim 1, wherein $R^8$ is

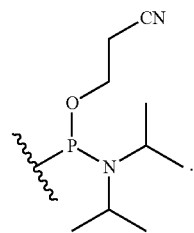

18. The compound of claim 1, wherein $R^x$ is —C(=O)C$_{1-6}$ alkyl, —CH$_2$-phenyl, or —C(=O)phenyl, or the hydrogen in —NHR$^x$ is absent and $R^x$ is

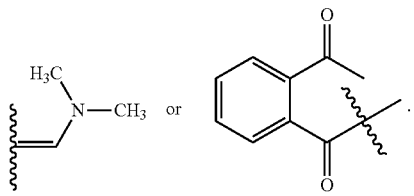

19. The compound of claim 1, having the structure:
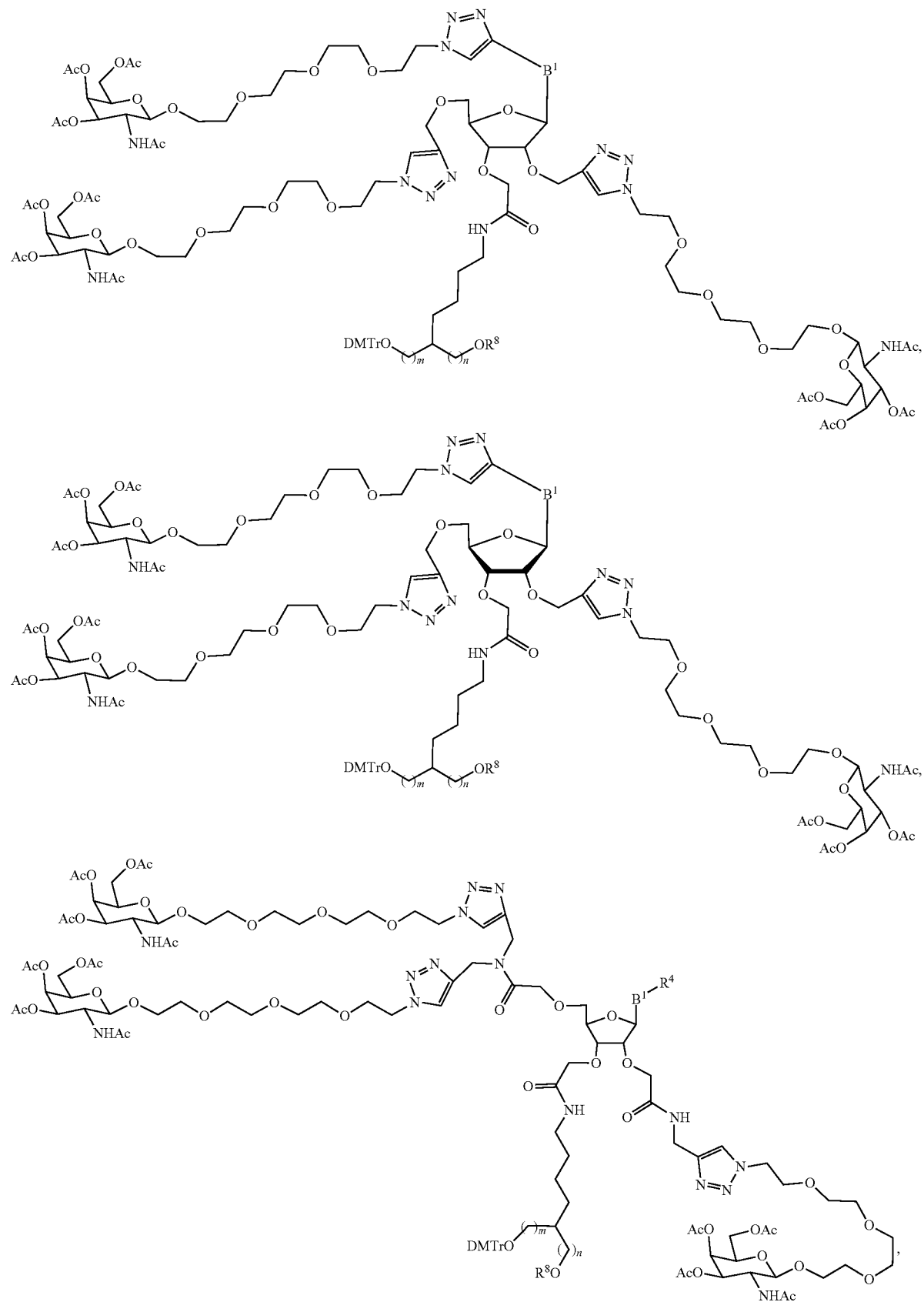

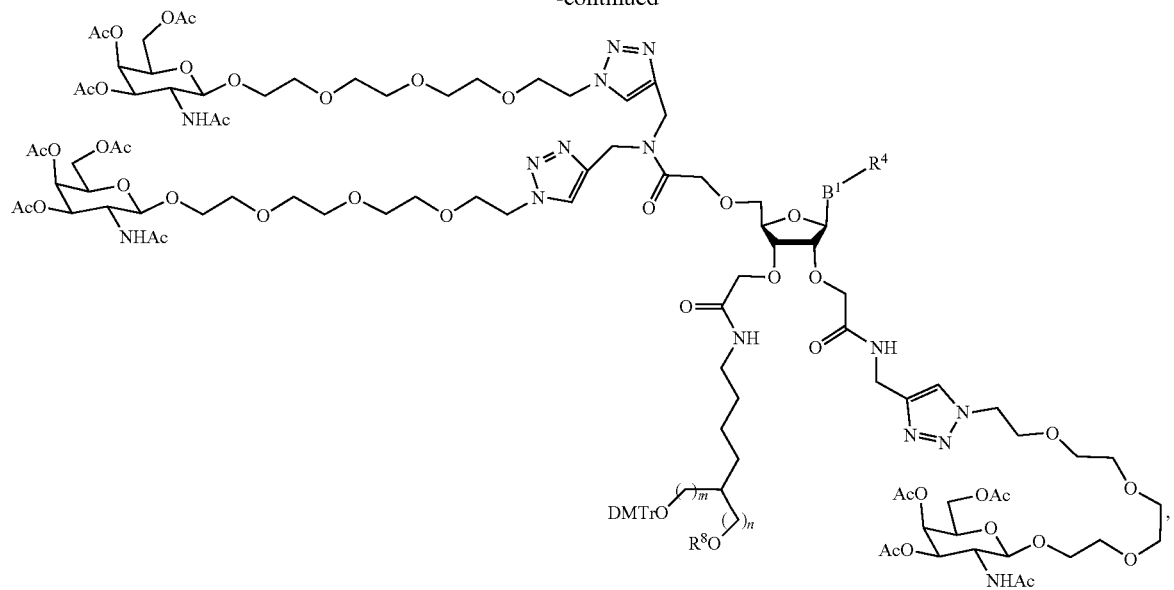
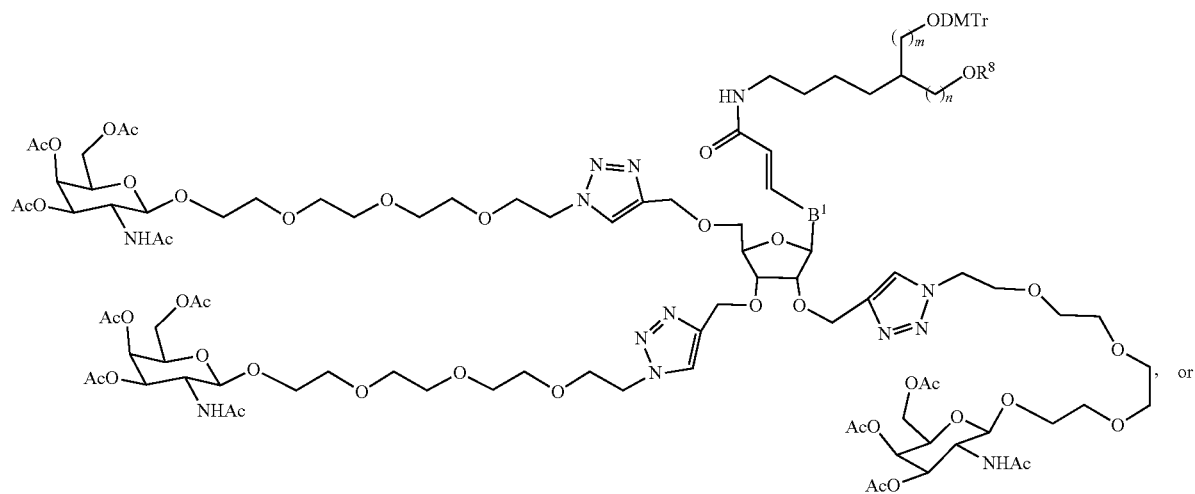
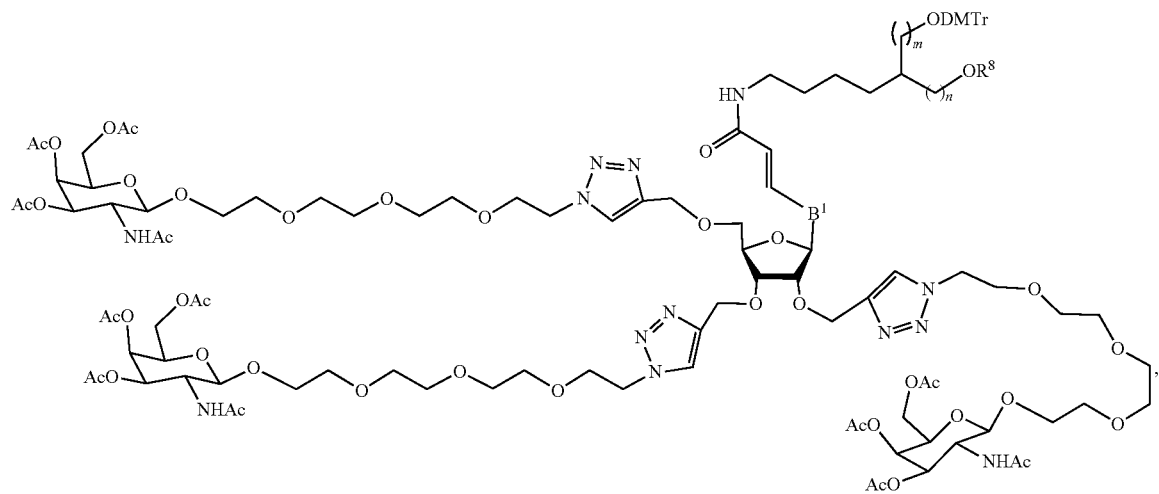

wherein $R^4$ is H;
each of m and m is independently 0, 1 or 2.
20. The compound of claim 19, having the structure:
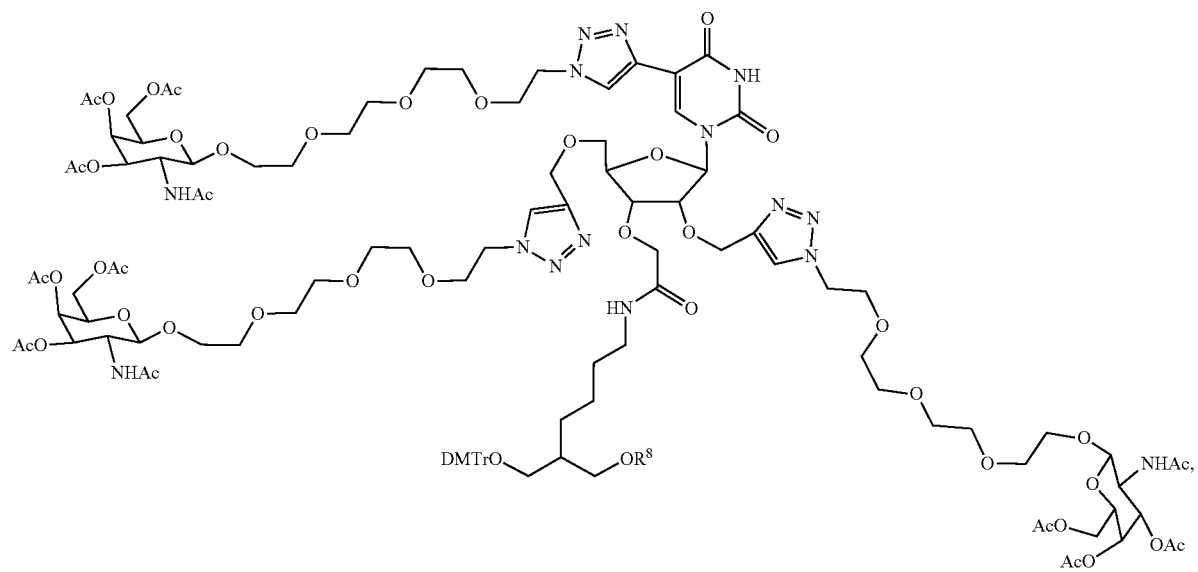
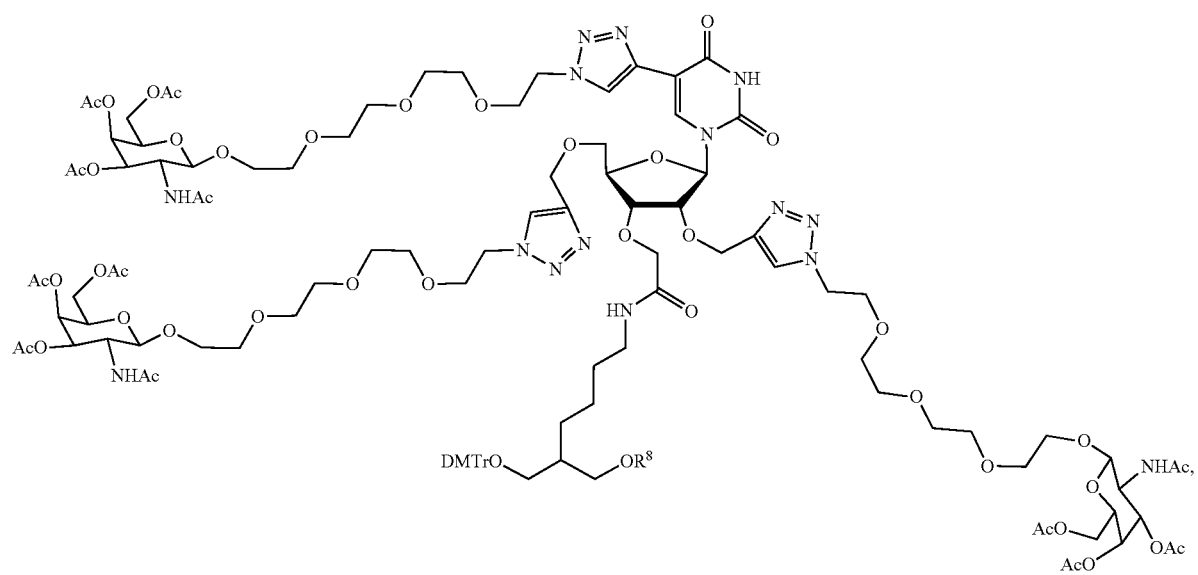

-continued
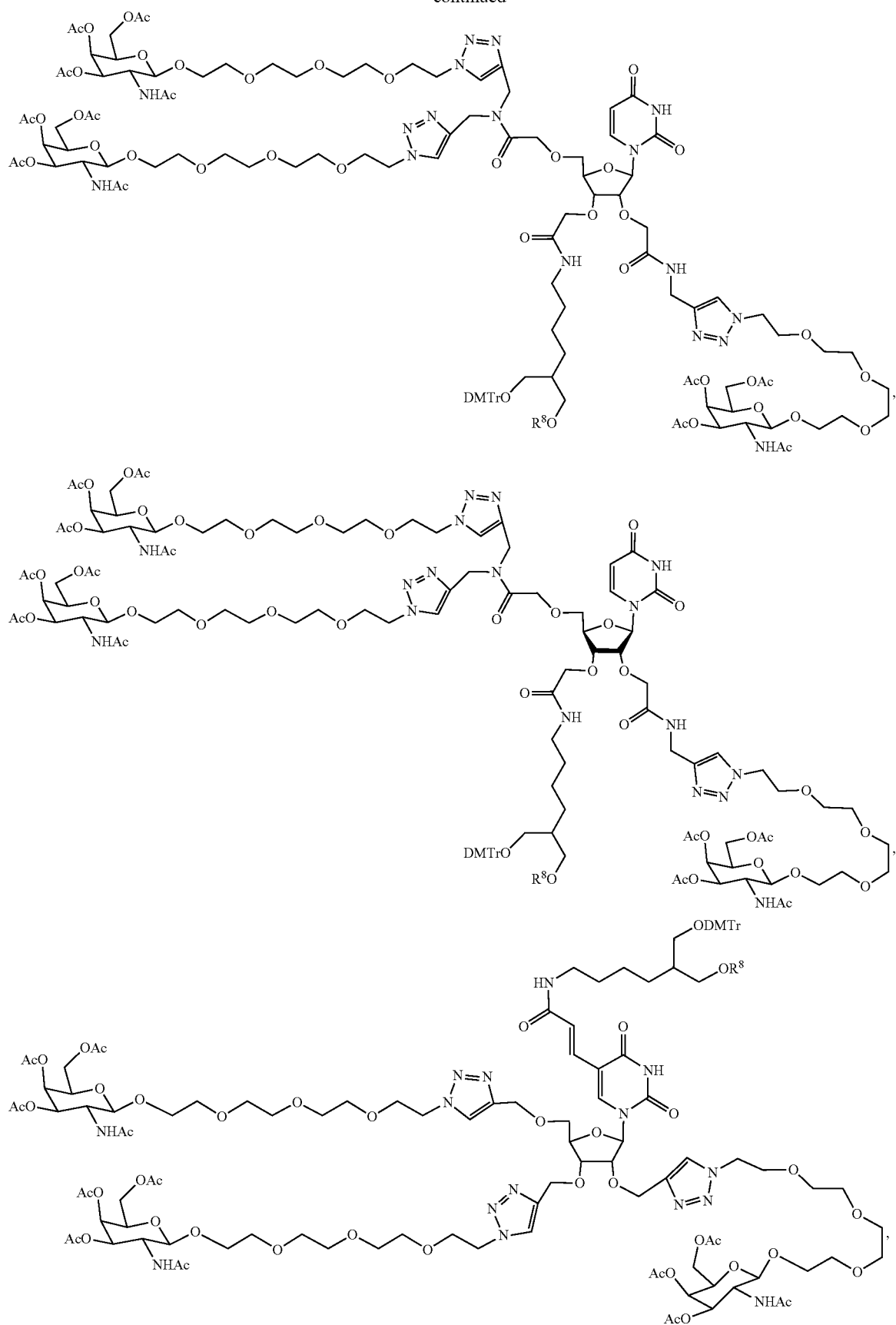

145
146
-continued
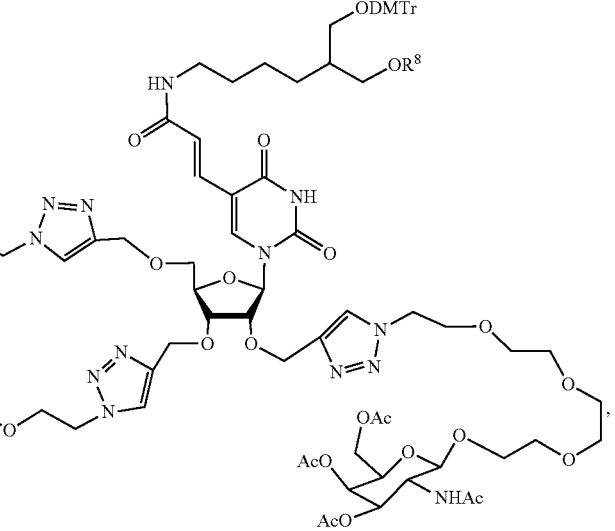

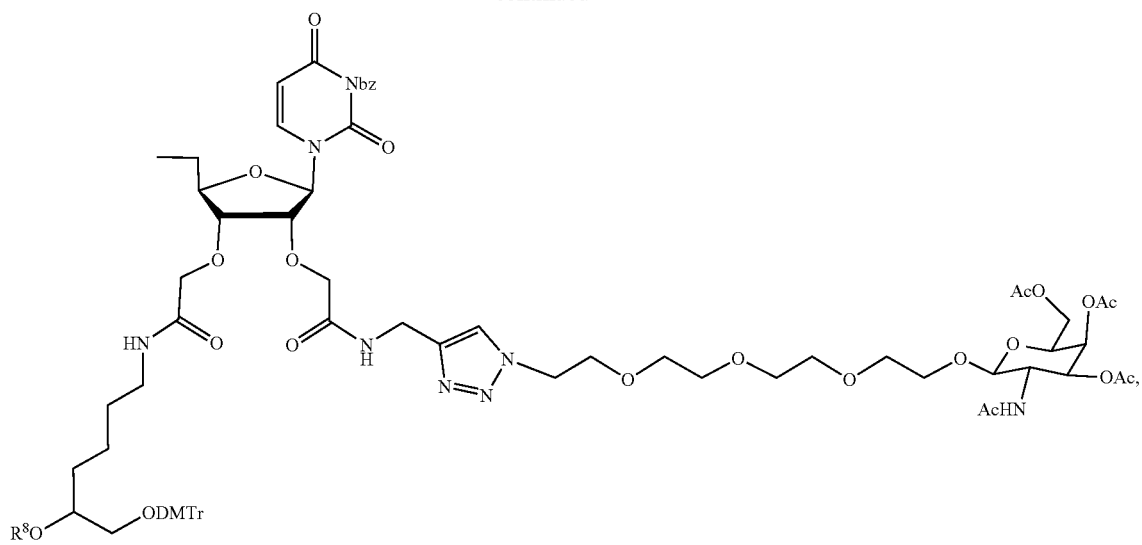
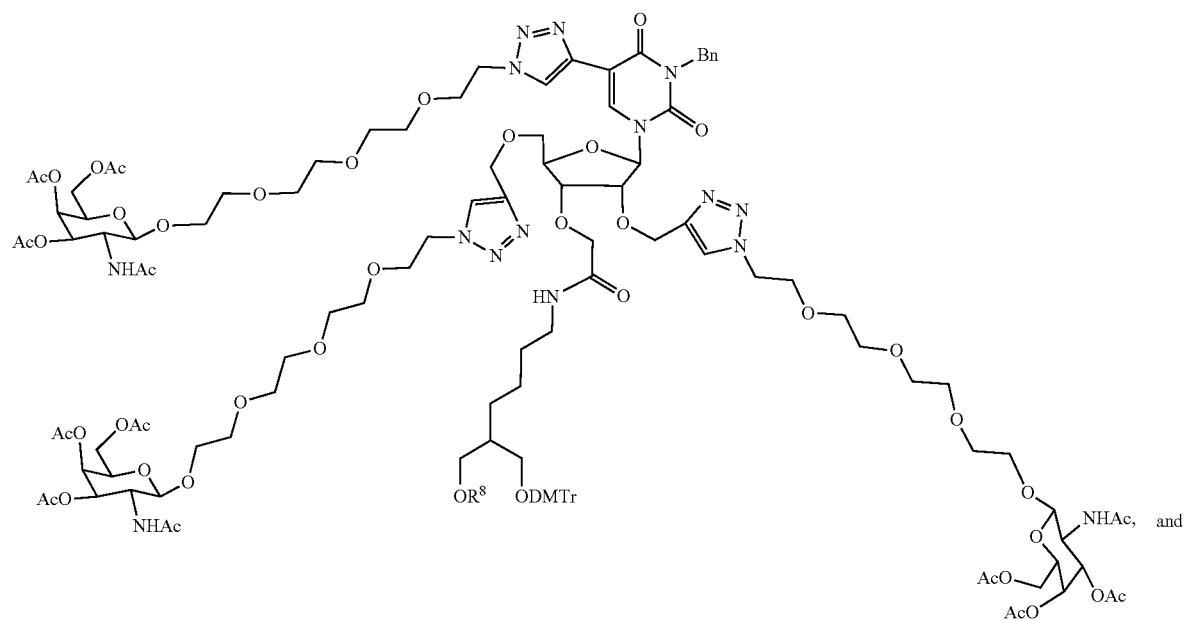

-continued

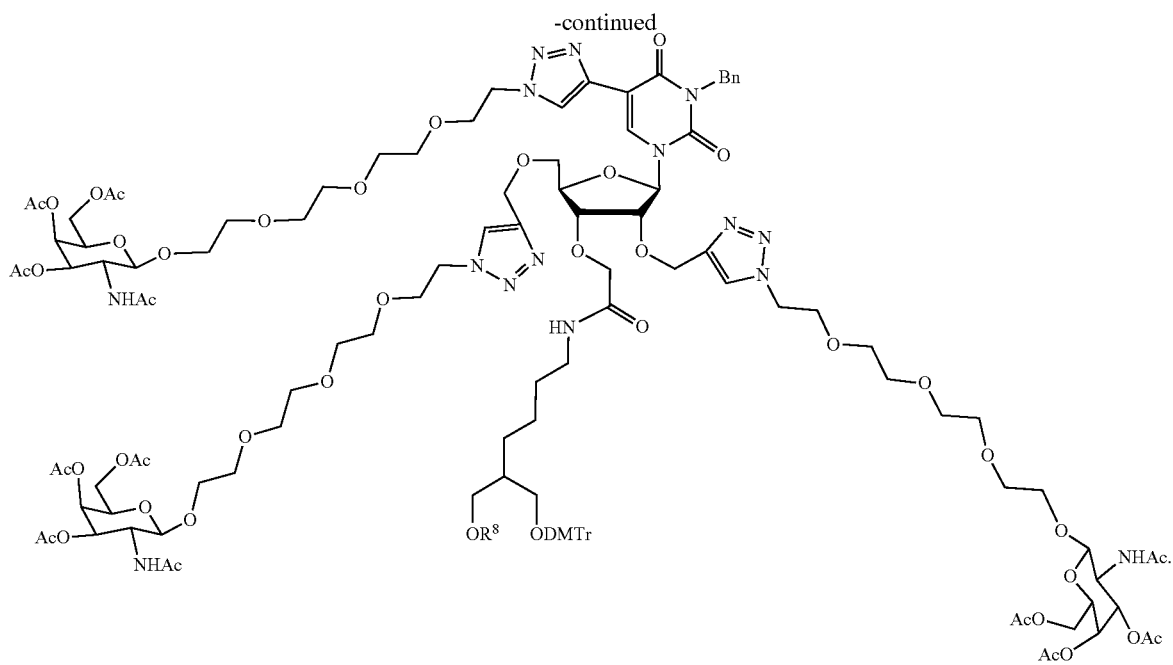

21. The compound of claim 19, wherein $R^8$ is —C(=O)CH$_2$CH$_2$C(=O)OH or

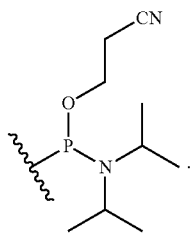 [SMILES: *P(OCCC#N)N(C(C)C)C(C)C ; "."]

.

22. A solid support comprising the compound of claim 1 covalently attached thereto via $R^8$ of the compound of Formula (I).

23. A method of preparing a synthetic oligonucleotide, comprising reacting a compound of claim 1, with an oligonucleotide.

24. A compound of Formula (II):

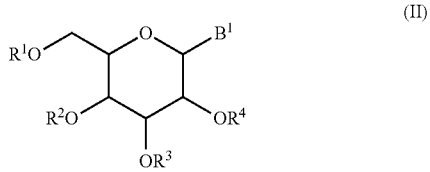

wherein:

each of $R^1$, $R^2$, $R^3$ and $R^4$ is independently -L$^{1a}$-Z-L$^2$-G, or -L$^{1b}$-C(=O)NR$^5$R$^6$;

wherein one of $R^1$, $R^2$, $R^3$, and $R^4$ is -L$^{1b}$-C(=O)NR$^5$R$^6$ and the others of $R^1$, $R^2$, $R^3$, and $R^4$ are not -L$^{1b}$-C(=O)NR$^5$R$^6$;

each $R^5$ is independently

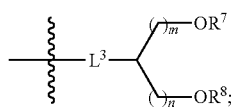

;

each of m and n is independently 0, 1, 2 or 3;

$R^6$ is H or $C_1$-$C_6$ alkyl;

$R^7$ is a hydroxy protecting group;

$R^8$ is hydrogen, a hydroxy protecting group, a phosphoramidite moiety, —C(=O)CH$_2$CH$_2$C(=O)R$^{8A}$, or —P(OR$^{8B}$)NR$^{8C}$R$^{8D}$;

$R^{8A}$ is —OH, —OR$^9$ or —NR$^{10}$R$^{11}$;

each of $R^{8B}$, $R^{8C}$ and $R^{8D}$ is independently H, $C_{1-6}$ haloalkyl, or unsubstituted or substituted $C_{1-6}$ alkyl;

$R^9$ is unsubstituted or substituted $C_{1-6}$ alkyl, or a hydroxy protecting group;

each of $R^{10}$ and $R^{11}$ is independently H, unsubstituted or substituted $C_{1-6}$ alkyl, or an amino protecting group;

each of $L^{1a}$ and $L^{1b}$ is independently $C_{1-10}$ alkylene, —CH=CH—, —CH$_2$CH=CH—, or 2 to 10 membered heteroalkylene, where one to three carbon atoms are replaced with C(=O), O, S or N;

each $L^2$ is independently $C_{1-10}$ alkylene, or 2 to 15 membered heteroalkylene wherein one to five carbon atoms are replaced with C(=O), O, S or N; or $C_1$-$C_{10}$ alkylene or 2 to 15 membered heteroalkylene each independently interrupted by a ring or ring system selected from the group consisting of $C_6$-$C_{10}$ arylene, $C_3$-$C_{10}$ cycloalkylene, five to ten membered heteroarylene, and three to ten membered heterocyclylene;

$L^3$ is $C_{1-10}$ alkylene;

each Z is a triazole ring, or a bi-, tri-, or tetracyclic ring system having a fused triazole ring;

$B^1$ is H, hydroxy, a protected hydroxy,

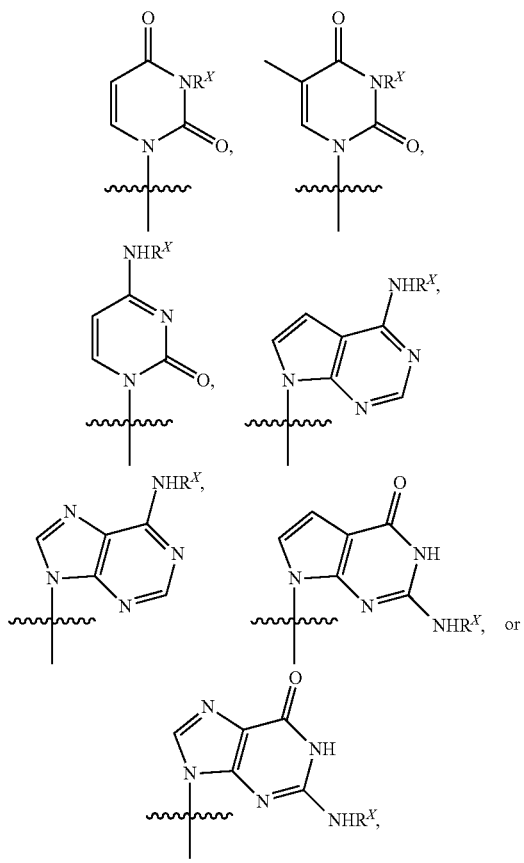

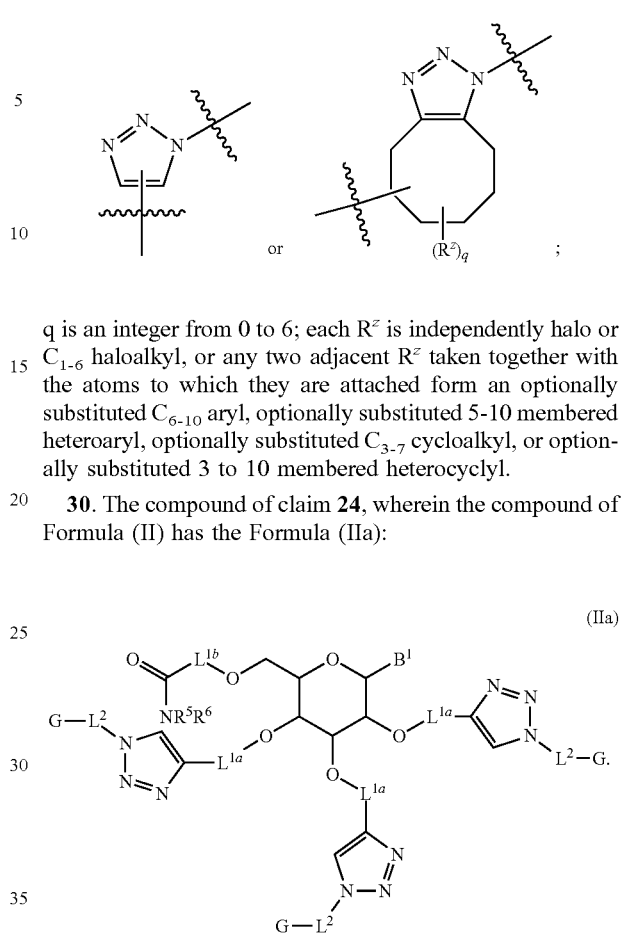

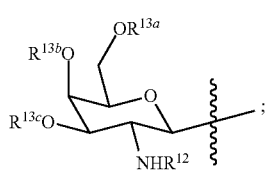

amino protecting group, or the hydrogen in —NHR$^x$ is absent and R$^x$ is a divalent amino protecting group;

G is

R$^{12}$ is —C(=O)C$_{1-6}$ alkyl, —C(=O)C$_{1-6}$ haloalkyl, or —C(=O)phenyl; and each of R$^{13a}$, R$^{13b}$ and R$^{13c}$ is independently hydrogen, benzyl (Bn), or —C(=O)R$^{13A}$ wherein R$^{13A}$ is C$_{1-6}$ alkyl, C$_{1-6}$ haloalkyl, or optionally substituted phenyl;

provided that the compound has three G groups.

25. The compound of claim 24, wherein R$^1$ is -L$^{1b}$-C(=O)NR$^5$R$^6$, and each of R$^2$, R$^3$ and R$^4$ is -L$^{1a}$-Z-L$^2$-G.

26. The compound of claim 24, wherein R$^2$ is -L$^{1b}$-C(=O)NR$^5$R$^6$, and each of R$^1$, R$^3$ and R$^4$ is -L$^{1a}$-Z-L$^2$-G.

27. The compound of claim 24, wherein R$^3$ is -L$^{1b}$-C(=O)NR$^5$R$^6$, and each of R$^1$, R$^2$ and R$^4$ is -L$^{1a}$-Z-L$^2$-G.

28. The compound of claim 24, wherein R$^4$ is -L$^{1b}$-C(=O)NR$^5$R$^6$, and each of R$^1$, R$^2$ and R$^3$ is -L$^{1a}$-Z-L$^2$-G.

29. The compound of claim 24, wherein each Z is independently q is an integer from 0 to 6; each R$^z$ is independently halo or C$_{1-6}$ haloalkyl, or any two adjacent R$^z$ taken together with the atoms to which they are attached form an optionally substituted C$_{6-10}$ aryl, optionally substituted 5-10 membered heteroaryl, optionally substituted C$_{3-7}$ cycloalkyl, or optionally substituted 3 to 10 membered heterocyclyl.

30. The compound of claim 24, wherein the compound of Formula (II) has the Formula (IIa):

31. The compound of claim 30, wherein each L$^{1a}$ and L$^{1b}$ is independently C$_{1-10}$ alkylene.

32. The compound of claim 31, wherein each L$^{1a}$ and L$^{1b}$ is —CH$_2$—.

33. The compound of claim 30, wherein each of L$^2$ is independently —(CH$_2$CH$_2$O)$_j$—, wherein j is 2, 3, 4, or 5.

34. The compound of claim 24, wherein each of R$^{13a}$, R$^{13b}$, and R$^{13c}$ is —C(=O)CH$_3$.

35. The compound of claim 24, wherein R$^{12}$ is —C(=O)CH$_3$ or —C(=O)CF$_3$.

36. The compound of claim 24, wherein L$^3$ is —CH$_2$— or —(CH$_2$)$_4$—.

37. The compound of claim 24, wherein m is 0 and n is 1, or m is 1 and n is 0.

38. The compound of claim 24, wherein both m and n are 0, or both m and n are 1.

39. The compound of claim 24, wherein R$^7$ is a trityl type of hydroxy protecting group selected from (4-methoxyphenyl)diphenylmethyl, bis(4-methoxyphenyl)phenylmethyl (DMTr), tris(4-methoxyphenyl)methyl, 9-phenylxanthen-9-yl, or 9-(4-methoxyphenyl)xanthen-9-yl.

40. The compound of claim 24, wherein R$^8$ is —C(=O)CH$_2$CH$_2$C(=O)OH.

41. The compound of claim 24, wherein $R^8$ is
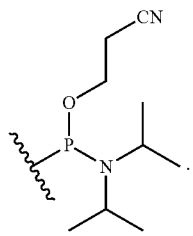
42. The compound of claim 24, wherein $B^1$ is:
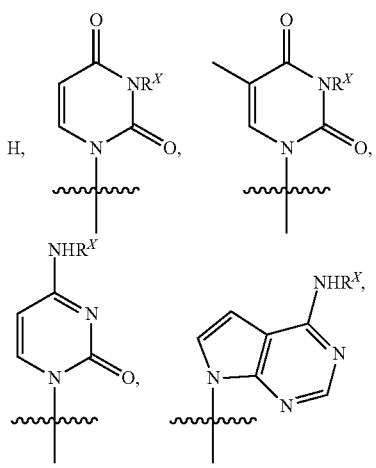
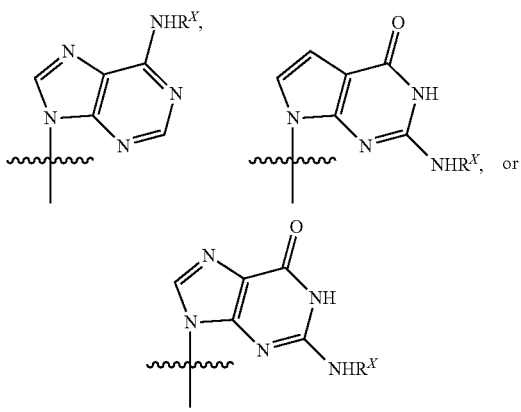
43. The compound of claim 42, wherein $R^x$ is —C(=O) $C_{1-6}$ alkyl, —CH$_2$-phenyl, or —C(=O)phenyl, or the hydrogen in —NHR$^x$ is absent and $R^x$ is
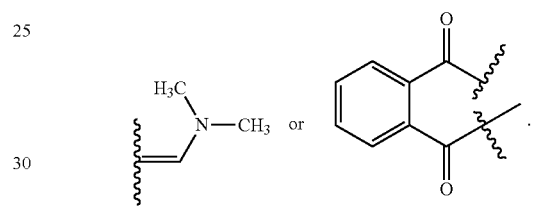
44. The compound of claim 24, having the structure:
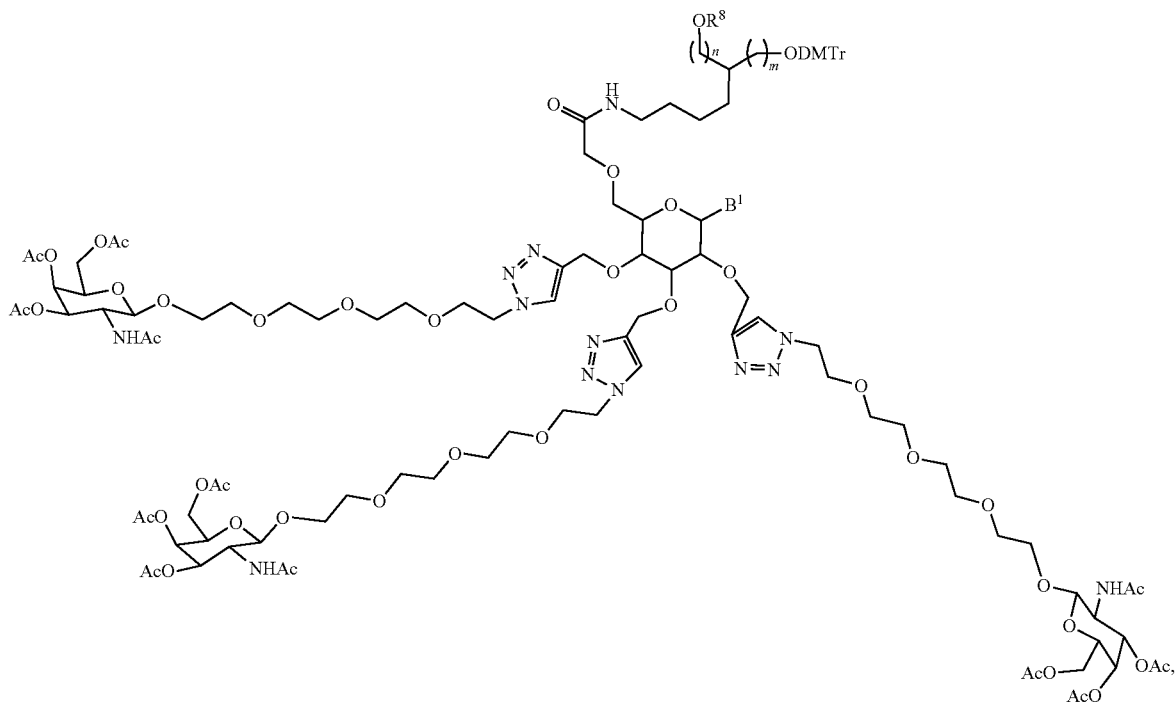

-continued
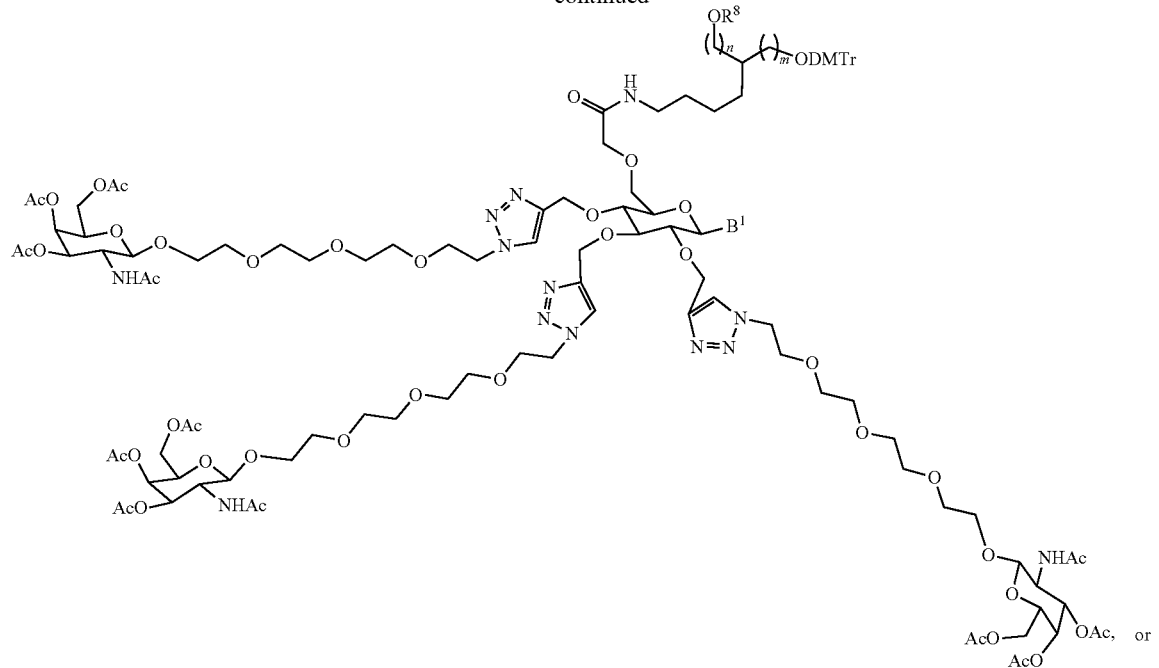
or
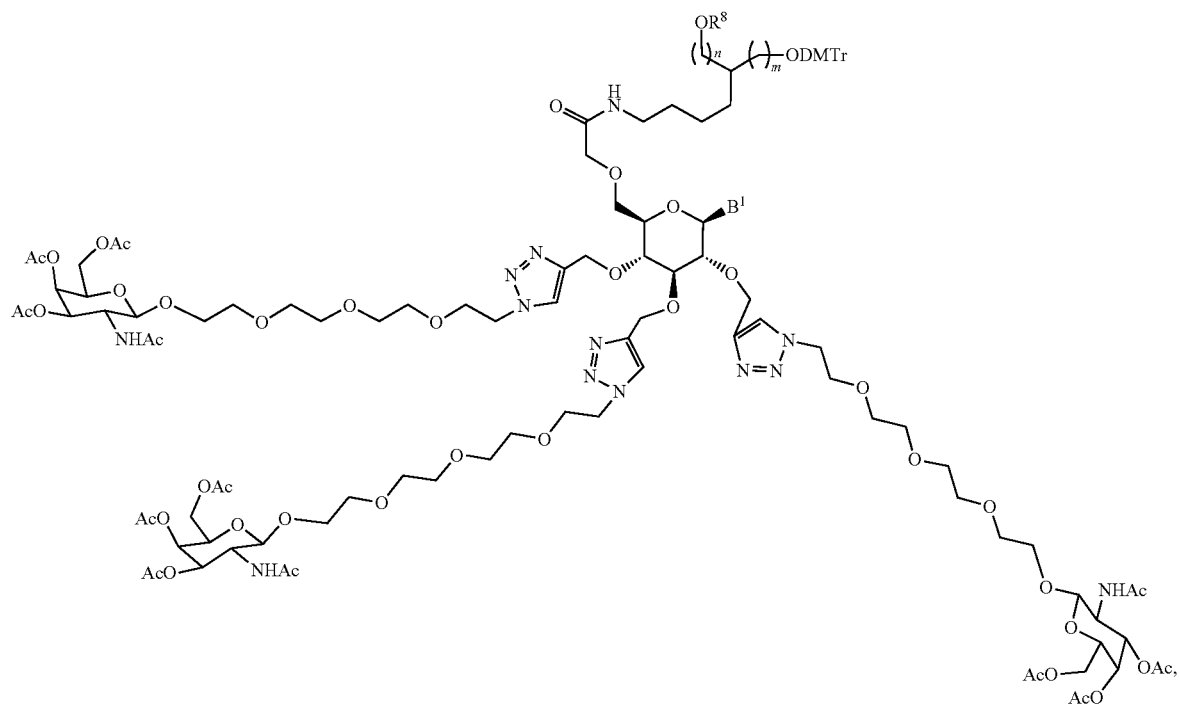
wherein each m and n is independently 0, 1 or 2.

45. The compound of claim 44, having the structure:
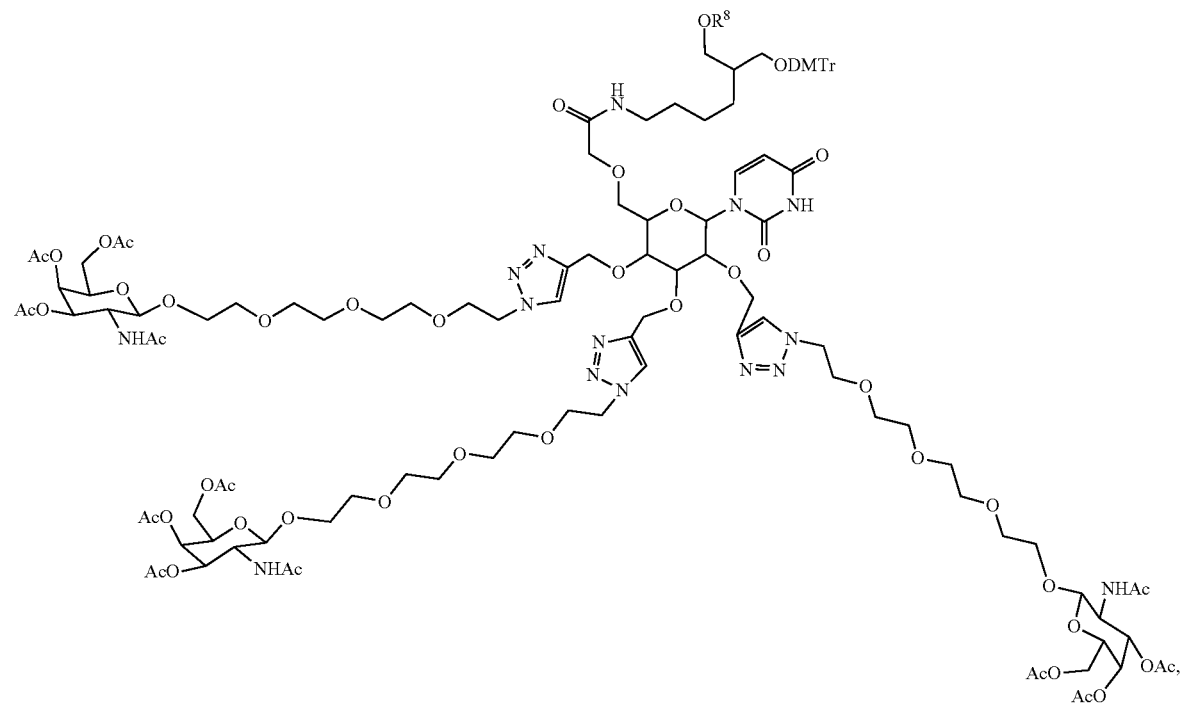
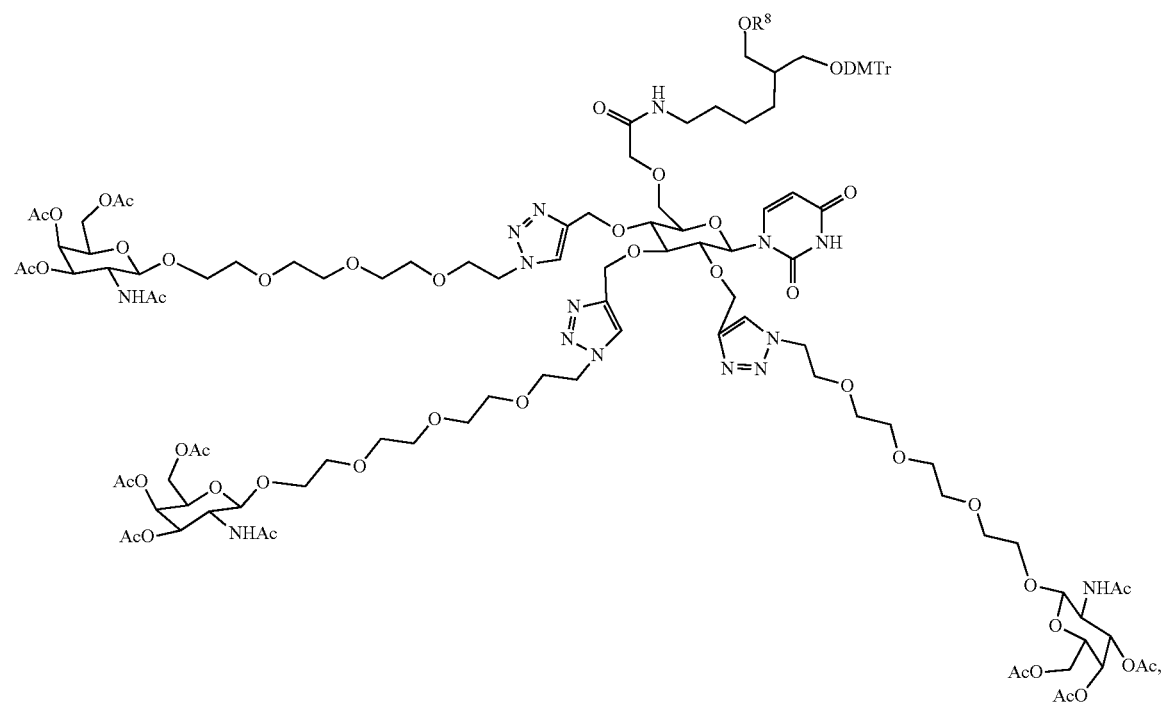

-continued
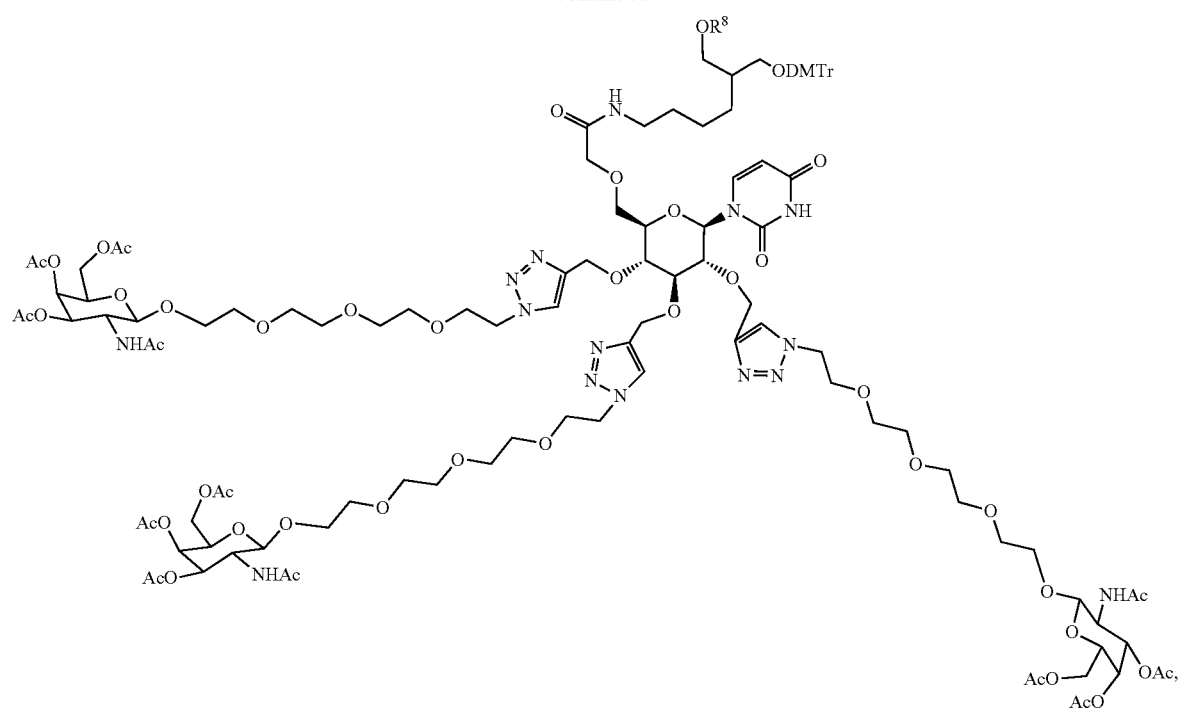
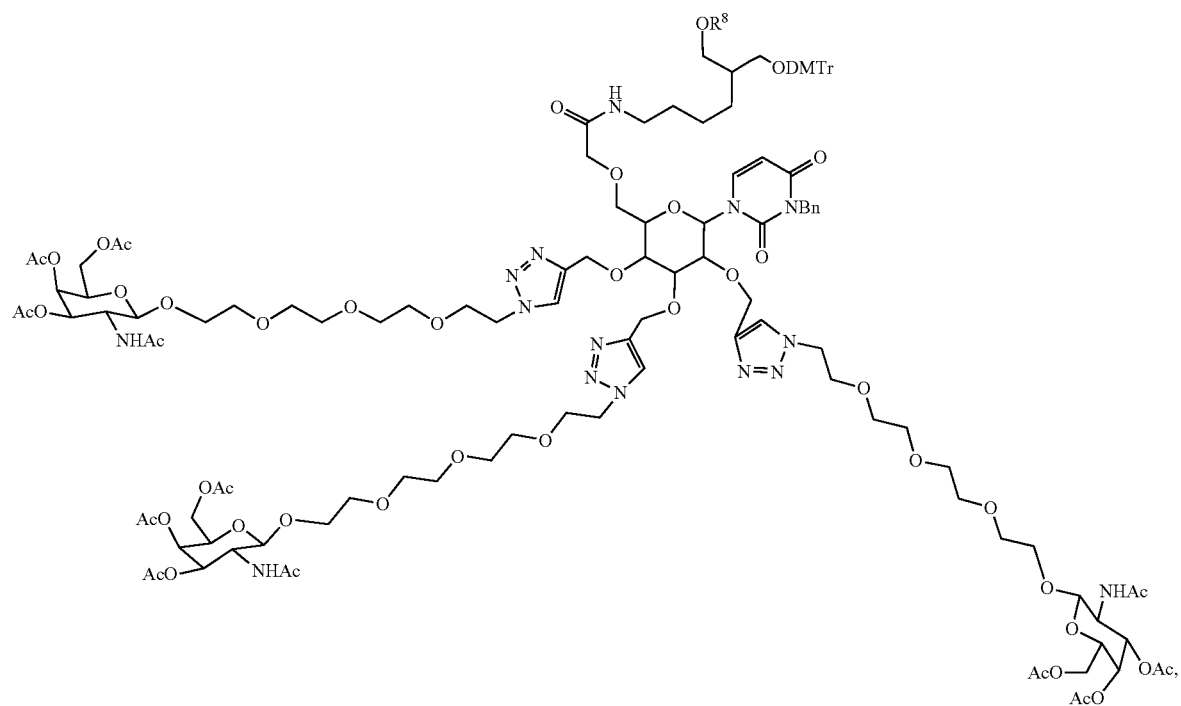

-continued
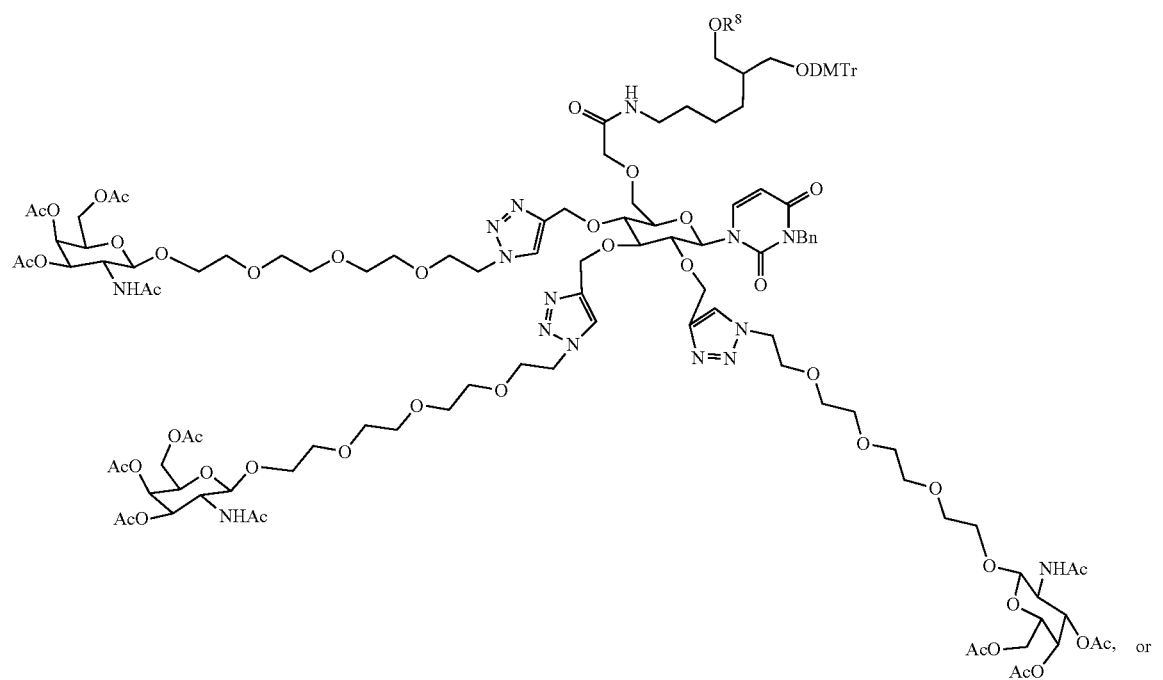
, or
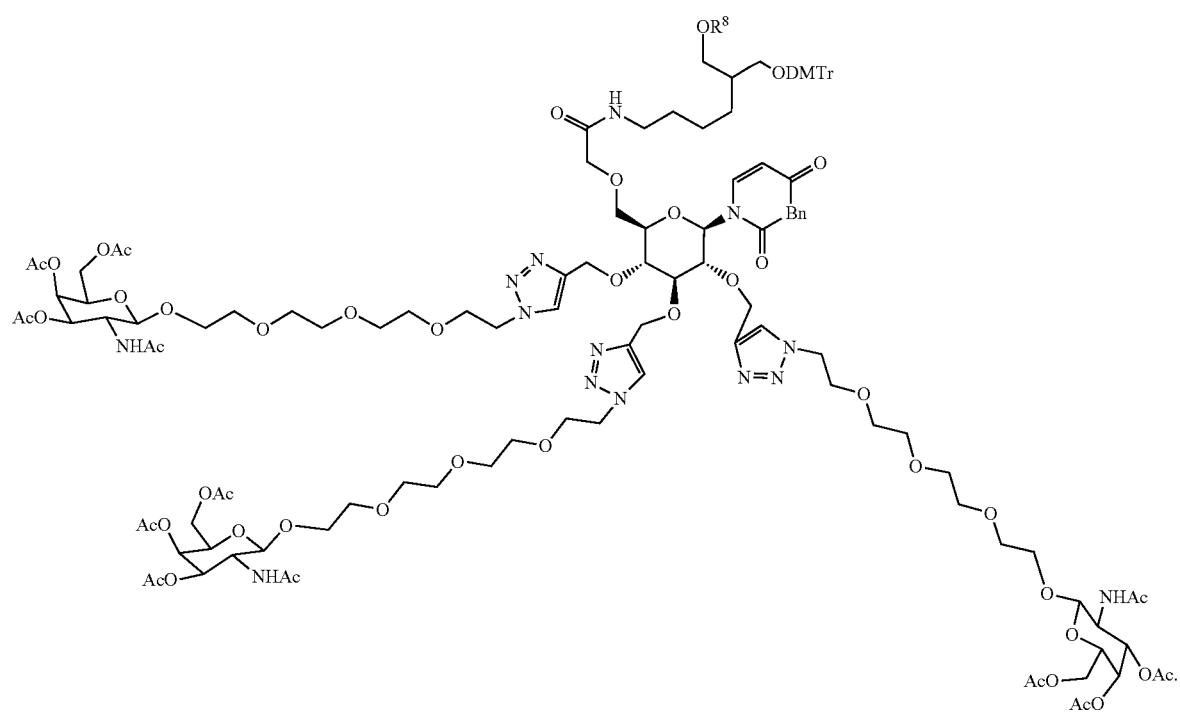
.

46. The compound of claim 44, wherein $R^8$ is —C(=O)CH$_2$CH$_2$C(=O)OH.
47. The compound of claim 44, wherein $R^8$ is
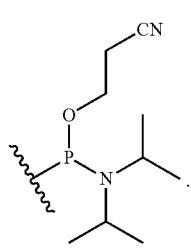 [SMILES: *P(OCCC#N)N(C(C)C)C(C)C]
48. A solid support comprising the compound of claim 24 covalently attached thereto via $R^8$ of the compound of Formula (II).
49. A method of preparing a synthetic oligonucleotide, comprising reacting a compound of claim 24, with an oligonucleotide.
* * * * *

SEQUENCE LISTING

Sequence total quantity: 1
SEQ ID NO: 1         moltype = DNA  length = 10
FEATURE              Location/Qualifiers

```
source          1..10
                mol_type = other DNA
                organism = synthetic construct
SEQUENCE: 1
tttttttttt                                              10
```